US011426417B2

(12) United States Patent
Reddy

(10) Patent No.: US 11,426,417 B2
(45) Date of Patent: Aug. 30, 2022

(54) NEUROACTIVE STEROID FORMULATIONS AND METHODS OF TREATING CNS DISORDERS

(71) Applicant: Sage Therapeutics, Inc., Cambridge, MA (US)

(72) Inventor: Kiran Reddy, Boston, MA (US)

(73) Assignee: Sage Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/396,065

(22) Filed: Apr. 26, 2019

(65) Prior Publication Data
US 2019/0247402 A1    Aug. 15, 2019

Related U.S. Application Data

(60) Division of application No. 15/649,583, filed on Jul. 13, 2017, now Pat. No. 10,322,139, which is a continuation of application No. 14/374,080, filed as application No. PCT/US2013/022772 on Jan. 23, 2013, now abandoned.

(60) Provisional application No. 61/589,740, filed on Jan. 23, 2012.

(51) Int. Cl.
*A61K 9/00*     (2006.01)
*B82Y 5/00*     (2011.01)
*A61K 31/57*    (2006.01)
*A61K 47/54*    (2017.01)
*A61K 47/61*    (2017.01)
*A61K 47/69*    (2017.01)

(52) U.S. Cl.
CPC .......... *A61K 31/57* (2013.01); *A61K 47/549* (2017.08); *A61K 47/61* (2017.08); *A61K 47/6951* (2017.08); *B82Y 5/00* (2013.01); *A61K 9/0019* (2013.01)

(58) Field of Classification Search
CPC .. A61K 31/57; A61K 47/549; A61K 47/6951; A61K 47/61; A61K 9/0019; B82Y 5/00
See application file for complete search history.

(56) References Cited

U.S. PATENT DOCUMENTS

| | | |
|---|---|---|
| 3,117,142 A | 1/1964 | Candido et al. |
| 3,169,134 A | 2/1965 | Klimstra et al. |
| 3,580,937 A | 5/1971 | Campbell et al. |
| 3,865,939 A | 2/1975 | Jandacek |
| 3,943,124 A | 3/1976 | Phillipps et al. |
| 3,983,111 A | 9/1976 | Phillipps et al. |
| 4,071,625 A | 1/1978 | Grunwell et al. |
| 4,192,871 A | 3/1980 | Phillipps et al. |
| 5,719,197 A | 2/1998 | Kanios et al. |
| 5,925,630 A | 7/1999 | Upasani et al. |
| 5,939,545 A | 8/1999 | Upasani et al. |
| 6,143,736 A | 11/2000 | Upasani et al. |
| 6,245,757 B1 | 6/2001 | Chopp et al. |
| 6,277,838 B1 | 8/2001 | Upasani et al. |
| 6,376,531 B1 | 4/2002 | Bell |
| 6,455,516 B1 | 9/2002 | Backstrom et al. |
| 6,603,008 B1 | 8/2003 | Ando et al. |
| 6,780,853 B1 | 8/2004 | Upasani et al. |
| 7,060,255 B2 | 6/2006 | Rabinowitz et al. |
| 7,064,116 B2 | 6/2006 | Calogeropoulou et al. |
| 7,090,830 B2 | 8/2006 | Hale et al. |
| 7,630,757 B2 | 12/2009 | Dorfmeister et al. |
| 7,816,074 B2 | 10/2010 | Smith et al. |
| 7,858,609 B2 | 12/2010 | Shaw et al. |
| 7,998,971 B2 | 8/2011 | Barlow et al. |
| 8,012,958 B2 | 9/2011 | Sabnani et al. |
| 8,618,087 B2 | 12/2013 | Shaw et al. |
| 8,697,678 B2 * | 4/2014 | Goodchild ............. A61K 31/56 514/178 |
| 8,969,329 B2 | 3/2015 | Brinton et al. |
| 9,056,116 B2 | 6/2015 | Shaw et al. |
| 9,084,797 B2 | 7/2015 | Caufriez et al. |
| 9,339,508 B2 | 5/2016 | Baulieu et al. |
| 9,365,611 B2 | 6/2016 | Martinez Botella et al. |
| 9,512,165 B2 | 12/2016 | Martinez Botella et al. |
| 9,630,986 B2 | 4/2017 | Covey et al. |
| 9,676,812 B2 | 6/2017 | Covey et al. |
| 9,765,110 B2 | 9/2017 | Covey |
| 2002/0072509 A1 | 6/2002 | Stein et al. |
| 2002/0183293 A1 | 12/2002 | Banerjee et al. |
| 2002/0198174 A1 | 12/2002 | Lyons |
| 2003/0032638 A1 | 2/2003 | Kim et al. |
| 2005/0201888 A1 | 9/2005 | Amar et al. |

(Continued)

FOREIGN PATENT DOCUMENTS

CA    2443266 A1     8/2002
CA    2443466    *  12/2002

(Continued)

OTHER PUBLICATIONS

Zhu et. al, British Journal of Anaesthesia 86 (3): 403-413 (2001).*
Martini et al., "Nasal and pulmonary drug delivery systems", Exp. Opin. Ther. Patents, (2000), 10(3):315-323.
Marx et al., "Neuroactive steroids are altered in schizophrenia and bipolar disorder: relevance to pathophysiology and therapeutics", Neuropsychopharmacology (2006) 31, 1249-1263.
Matsumoto et al., "GAGAâreceptor neutrotransmission dysfunction in a mouse model of social isolation-induced stress: Possible insights into a non-serotonergic mechanism of action of SSRIs in mood and anxiety disorders", Stress, Mar. 2007; 10(1): 3-12.
Mayer et al., "Refractory Status Epilepticus Frequency, Risk Factors, and Impact on Outcome", Archives of Neurology (2002), vol. 59, pp. 205-210.

(Continued)

Primary Examiner — Shirley V Gembeh
(74) Attorney, Agent, or Firm — Honigman LLP; Harold H. Fox; Jonathan P. O'Brien

(57) ABSTRACT

Formulations of comprising a neuroactive steroid, e.g., allopregnanolone; and optionally a cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®; and methods of use in treating CNS disorders.

6 Claims, 8 Drawing Sheets

(56) References Cited

U.S. PATENT DOCUMENTS

| | | |
|---|---|---|
| 2006/0063707 A1 | 3/2006 | Baudry et al. |
| 2006/0198896 A1 | 9/2006 | Liversidge et al. |
| 2007/0014719 A1 | 1/2007 | Reading et al. |
| 2007/0020299 A1 | 1/2007 | Pipkin et al. |
| 2007/0081948 A1 | 4/2007 | Morton et al. |
| 2007/0287931 A1 | 12/2007 | Dilorenzo |
| 2008/0195160 A1 | 8/2008 | Wingeier et al. |
| 2008/0269183 A1 | 10/2008 | Mellon et al. |
| 2009/0074677 A1 | 3/2009 | Marx et al. |
| 2009/0130216 A1 | 5/2009 | Cartt et al. |
| 2009/0162441 A1 | 6/2009 | Bartus et al. |
| 2009/0198145 A1 | 8/2009 | Chow |
| 2009/0203658 A1 | 8/2009 | Marx et al. |
| 2009/0221544 A1 | 9/2009 | Stein et al. |
| 2009/0239942 A1 | 9/2009 | Cloyd |
| 2009/0325920 A1 | 12/2009 | Hoffman et al. |
| 2010/0136105 A1 | 6/2010 | Chen et al. |
| 2010/0234335 A1 | 9/2010 | Gravanis et al. |
| 2010/0297181 A1 | 11/2010 | Hanada et al. |
| 2010/0316678 A1 | 12/2010 | Goodchild |
| 2010/0317638 A1 | 12/2010 | Covey et al. |
| 2010/0331762 A1 | 12/2010 | Wingeier et al. |
| 2011/0054038 A1 | 3/2011 | Glozman |
| 2011/0152840 A1 | 6/2011 | Lee et al. |
| 2011/0288059 A1 | 11/2011 | Marx et al. |
| 2011/0306579 A1 | 12/2011 | Stein |
| 2011/0319386 A1 | 12/2011 | Barlow et al. |
| 2012/0142645 A1 | 6/2012 | Marx |
| 2012/0302535 A1 | 11/2012 | Caufriez et al. |
| 2012/0316146 A1 | 12/2012 | Goodchild et al. |
| 2013/0210783 A1 | 8/2013 | Marx et al. |
| 2013/0309306 A1 | 11/2013 | Rogawski et al. |
| 2014/0050789 A1 | 2/2014 | Rogawski et al. |
| 2014/0057885 A1 | 2/2014 | Reddy et al. |
| 2014/0058079 A1 | 2/2014 | Mensah-Nyagan et al. |
| 2014/0148412 A1 | 5/2014 | Hogenkamp |
| 2014/0322198 A1 | 10/2014 | Buchwald-Werner et al. |
| 2014/0343027 A1 | 11/2014 | Rogawski |
| 2015/0018327 A1 | 1/2015 | Reddy |
| 2015/0158903 A1 | 6/2015 | Upasani et al. |
| 2015/0175651 A1 | 6/2015 | Salituro et al. |
| 2015/0265632 A1 | 9/2015 | Goodchild et al. |
| 2015/0290181 A1 | 10/2015 | Lee et al. |
| 2015/0291654 A1 | 10/2015 | Upasani et al. |
| 2015/0313915 A1 | 11/2015 | Rogawski et al. |
| 2016/0068563 A1 | 3/2016 | Martinez Botella et al. |
| 2016/0083418 A1 | 3/2016 | Martinez Botella et al. |
| 2016/0108080 A1 | 4/2016 | Martinez Botella et al. |
| 2018/0050005 A1 | 2/2018 | DiMauro et al. |
| 2018/0050107 A1 | 2/2018 | DiMauro et al. |
| 2018/0064728 A1 | 3/2018 | Chang et al. |
| 2018/0071315 A1 | 3/2018 | Cashman et al. |
| 2018/0133229 A1 | 5/2018 | Rogawski et al. |
| 2018/0153906 A1 | 6/2018 | Rogawski et al. |
| 2018/0193357 A1 | 7/2018 | Rogawski et al. |
| 2018/0235916 A1 | 8/2018 | Kaufman et al. |
| 2018/0256726 A1 | 9/2018 | Rogawski |
| 2018/0296487 A1 | 10/2018 | Saporito et al. |
| 2018/0369171 A1 | 12/2018 | Pinna et al. |
| 2019/0160078 A1 | 5/2019 | Masuoka et al. |
| 2019/0337975 A1 | 11/2019 | Bryson et al. |

FOREIGN PATENT DOCUMENTS

| | | |
|---|---|---|
| CN | 1190404 A | 8/1998 |
| CN | 104136452 A | 11/2014 |
| EP | 0233849 A1 | 8/1987 |
| EP | 0554436 A1 | 8/1993 |
| EP | 0656365 A1 | 6/1995 |
| EP | 0701444 A1 | 3/1996 |
| EP | 0808325 A1 | 11/1997 |
| EP | 1038880 A2 | 9/2000 |
| EP | 1819353 A1 | 8/2007 |
| GB | 1430942 A | 4/1976 |
| GB | 1570394 A | 7/1980 |
| GB | 1581234 A | 12/1980 |
| WO | 1991011172 A1 | 8/1991 |
| WO | 1991016897 A1 | 11/1991 |
| WO | 9303732 A1 | 3/1993 |
| WO | 9305786 A1 | 4/1993 |
| WO | 9318053 A1 | 9/1993 |
| WO | 9427608 A1 | 12/1994 |
| WO | 1995021617 A1 | 8/1995 |
| WO | 9526325 A2 | 10/1995 |
| WO | 1996003421 A1 | 2/1996 |
| WO | 1996016076 A1 | 5/1996 |
| WO | 9640043 A2 | 12/1996 |
| WO | 1997003677 A1 | 2/1997 |
| WO | 9805337 A1 | 2/1998 |
| WO | 1999045931 A1 | 9/1999 |
| WO | 2002030409 A2 | 4/2002 |
| WO | 2004019953 A1 | 3/2004 |
| WO | 2005105822 A2 | 11/2005 |
| WO | 2006102644 A2 | 9/2006 |
| WO | 2007062266 A2 | 5/2007 |
| WO | 2008/128049 A2 | 10/2008 |
| WO | 2008157460 A1 | 12/2008 |
| WO | 2009/088530 A1 | 7/2009 |
| WO | 2010003391 A2 | 1/2010 |
| WO | 2010042925 A2 | 4/2010 |
| WO | 2010063030 A2 | 6/2010 |
| WO | 2010107815 A1 | 9/2010 |
| WO | 2011088503 A1 | 7/2011 |
| WO | 2012059456 A1 | 5/2012 |
| WO | 2012075286 A2 | 6/2012 |
| WO | 2012110010 A1 | 8/2012 |
| WO | 2012116290 A2 | 8/2012 |
| WO | 2013036835 A1 | 3/2013 |
| WO | 2013043985 A1 | 3/2013 |
| WO | 2013056181 A1 | 4/2013 |
| WO | 2013078500 A1 | 6/2013 |
| WO | 2013112605 A2 | 8/2013 |
| WO | 2013188792 A2 | 12/2013 |
| WO | 2014028398 A2 | 2/2014 |
| WO | 2014031792 A2 | 2/2014 |
| WO | 2014085668 A1 | 6/2014 |
| WO | 2014108808 A2 | 7/2014 |
| WO | 2015195962 A1 | 12/2015 |
| WO | 2016040322 A1 | 3/2016 |
| WO | 2016127170 A1 | 8/2016 |
| WO | 2017021325 A1 | 2/2017 |
| WO | 2017066240 A1 | 4/2017 |
| WO | 2017156103 A1 | 9/2017 |
| WO | 2018035095 A1 | 2/2018 |
| WO | 2018048789 A1 | 3/2018 |
| WO | 2018169798 A1 | 9/2018 |
| WO | 2018195186 A1 | 10/2018 |
| WO | 2018236955 A1 | 12/2018 |
| WO | 2018237282 A1 | 12/2018 |
| WO | 2019051477 A1 | 3/2019 |
| WO | 2019055764 A1 | 3/2019 |
| WO | 2019094724 A1 | 5/2019 |
| WO | 2019113494 A1 | 6/2019 |
| WO | 2019126741 A1 | 6/2019 |
| WO | 2019126761 A1 | 6/2019 |
| WO | 2019140272 A1 | 7/2019 |
| WO | 2019241442 A1 | 12/2019 |
| WO | 2020077255 A1 | 4/2020 |
| WO | 2020082065 A1 | 4/2020 |
| WO | 2020118060 A1 | 6/2020 |
| WO | 2020132504 A1 | 6/2020 |
| WO | 2020243027 A1 | 12/2020 |
| WO | 2020243488 A1 | 12/2020 |
| WO | 2021113786 A1 | 6/2021 |
| WO | 2021188778 A2 | 9/2021 |
| WO | 2021195297 A1 | 9/2021 |

(56) References Cited

FOREIGN PATENT DOCUMENTS

| WO | 2021195301 A1 | 9/2021 |
|---|---|---|
| WO | 2022020363 A1 | 1/2022 |

OTHER PUBLICATIONS

Meierkord et al., "EFNS Guideline on the Management of Status Epilepticus in Adults", European Journal of Neurology (2010), vol. 17, pp. 348-355.
Meltzer-Brody et al., "Phase 2 and 3 Studies Evaluating Brexanolone iv, a GABAA Receptor Positive Allosteric Modulator, in Postpartum Depression", Presented at the 56th Annual Meeting of the American College of Neuropsychopharmacology; Dec. 3, 2017, 14 pages.
Melville, "New drug shows rapid, robust effect in postpartum", Medscape, (2017), 2 pages.
Merzlikine et al., "Development of machine learning models of b-cyclodextrin and sulfobutylether-b-cyclodextrin complexation free energies", International Journal of Pharmaceutics (2011), vol. 418, pp. 207-216.
Miller, "Postpartum Depression", Clinician's Corner, vol. 287, No. 6, (2002), pp. 762-765.
Monagle et al., "A Phase 1c Trial Comparing the Efficacy and Safety of a New Aqueous Formulation of Alphaxalone with Propofol", Anesthesia & Analgesia (2015), vol. 121, No. 4, pp. 914-924.
Morgan, et al. "Neuroactive steroids after estrogen exposure in depressed postmenopausal women treated with sertraline and asymptomatic postmenopausal woman", Arch Womens Ment, Health (2010) 13:91-98.
Moses Kolko et al., "Antepartum and Postpartum Depression: Healthy Mom, Healthy Baby", Journal of the American Medical Women's Association, 2004; 59: pp. 181-191.
Munari et al., "The Use of Althesin in Drug-Resistant Status Epilepticus", Epilepsia (1979), vol. 20, pp. 475-484.
Murayama et al., "Effects of neurosteroid 3a-hydroxy-5a-pregnan-20-one on ethanol-mediated paired-pulse depression of population spikes in the CA1 region of rat hippocampal slices", Neuroscience Letters 394 (2006) 28-32.
Murray et al., "Maternal Postnatal Depression and the Development of Depression in Offspring Up to 16 Years of Age", Journal of the American Academy of Child & Adolescent Psychiatry, 2011; 50 (5), pp. 460-470.
Murray et al., "Prediction, detection, and treatment of post natal depression", Archives Of Disease In Childhood, The Journal of the Royal College of Paediatrics and Child Health, 1997, 77: 97-101.
Másson et al., "Cyclodextrins and the liquid-liquid phase distribution of progesterone, estrone and prednicarbate", J Incl Phenom Macrocycl Chem (2007), vol. 57, pp. 481-487.
Naert, et al. "Neuroactive steroids modulate HPA axis actiity and cerebral brain-derived neurotrophic factor (BDNF) protein levels in adult male rats", Psychoneuroendocrinology (2007) 32, 1062-1078.
Nanjwade et al., Pulmonary Drug Delivery: Novel Pharmaceutical Technologies Breathe New Life into the Lungs, PDA JPharm Sci and Tech, (2015), 65: 513-534.
Nappi et al., "Serum Allopregnanolone in women with postpartum blues", Obstetrics & Gynecology, vol. 97, No. 1, 2001: 77-80.
Nin et al. "Neurosteroids reduce social insolation-induced behavioral deficits; a proposed link with neurosteroid-mediated upregulation of BDNF expression", Frontiers in Endocrinology (2011) vol. 2, Article 73.
Nin et al., "The effect of intra-nucleus accumbens administration of allopregnanolone on 6 and y2 GABAA receptor subunit mRNA expression in the hippocampus and on depressive-like and grooming behaviors in rats," Pharmacology, Biochemistry and Behavior, (2012), 103:359-366.
Northdurfter et al., "Recent Developments in Potential Anxiolytic Agents Targeting GABAA/BzR Complex or the Translocator Protein (18kDa) (TSPO)", Current Topics in Medicinal Chemistry, 2012,12; 360-370.

Notification of Transmittal of the International Search Report and the Written Opinion of the International Searching authority, or the Declaration, International Application No. PCT/US13/45933, dated Dec. 3, 2013, 5 Pages.
Novy et al., "Refractory Status Epilepticus: A Prospective Observational Study", Epilepsia (2010), vol. 51, No. 2, pp. 251-256.
Oka et al., "A reliable method for intratracheal instillation of materials to the entire lung in rats," J Toxicol Pathol, (2006), 19:107-109.
Osborne et al.,"Replication of epigenetic postpartum depression biomarkers and variation with hormone levels," Neuropsychopharmacology, Accepted Manuscript (2015), pp. 1-32.
Park et al., "Multiple effects of allopregnanolone on GABAergic responses in single hippocampal CA3 pyramidal neurons", European Journal of Pharmacology (2011), vol. 652, pp. 46-54.
Pearlstein, et al. "Premenstrual dysphoric disorder: burden of illness and treatment update", J Psychiatry Neurosci 2008:33(4):291-301.
Phillipps et al., "A New Series of Steroidal Antidysrhythmic Agents," J. Steroid Biochem. 19(1):759-765 (1983).
Phillipps et al., "Water-soluble Steroidal Anaesthetics", Journal of Steroid Biochemistry 11:79-86 (1979).
Phillipps, "Structure-Activity Relationships in Steroidal Anaesthetics", Journal of Steroid Biochemistry, (1975), vol. 6, pp. 607-613.
Pieribone et al., "Clinical Evaluation of Ganaxolone in Pediatric and Adolescent Patients with Refractory Epilepsy", Epilepsia (2007), vol. 48, No. 10, pp. 1870-1874.
Pinna, et al., "Up-Regulation of Neutrosteriod Biosynthesis as a Pharmacological Strategy to improve behavioural Deficits in a Putative mouse model of Post-traumatic stress disorder", Journal of Neuroendocrinology 24 (2011), p. 102-116.
Pires et al., "Intranasal Drug Delivery: How, Why and What for?" Journal of Pharm, Pharmaceut Sci, (2009), 12 (3):288-311.
Poromaa et al., "GABA receptor, progresteron and premenstrual dysphoric disorder", Arch Womens Ment Health (2003) 6:23-41.
Pubchem, CID 92786.
Puia, et al. "Novel modulatory effects of neurosteriods and benzodiazepines on excitatory and inhibitory neurons excitability: a multi-electrode array recording study", Frontiers in Neutral Circuits, (2012) vol. 6, Article 94.
Ramsay, "Treatment of status epilepticus". Epilepsia, 2013, 34 Suppl.:S71-S81.
Rapkin et al., "Progesterone metabolite allopregnanolone in women with premenstrual syndrome", Obstet. Gynecol 1997; 90:709-714.
Rasheed et al., "Cyclodextrins as Drug Carrier Molecule: A Review", Scientia Pharmaceutica, Review, (2008), pp. 567-598.
Rasmusson, et al. "Decreased Cerebrospinal Fluid Allopregnanolone levels in women with posttraumatic stress disorder", Biol Psychiatry 2006;60:704-713.
Reddy "Role of anticonvulsant and antiepileptogenic neurosteroids in the pathophysiology and treatment of epilepsy," Frontiers in Endocrinology, 2:38, (2011).
Reddy "The clinical potentials of endogenous neurosteroids" Drugs of Today 2002, 38 (7): 465-485.
Reddy et al., "Neurosteroids—Endogenous Regulators of Seizure Susceptibility and Role in Treatment of Epilepsy", Jasper's Basic Mechanisms of the Epilepsies Fourth Edition (2012), pp. 1-23.
Reddy, "Neurosteroids: Endogenous role in the human brain and therapeutic potentials", Progress in Brain Research, (2010) vol. 186, pp. 113-137.
Reddy, "Pharmacology of Endogenous Neuroactive Steroids", Critical Reviews in Neurobiology, 15 (3&4)197-234 (2003).
Reddy, "SGE-102: a novel therapy for refractory status epilepticus". Epilepsia, Abstract 34 Suppl 6: 81-82.
Rogawski et al., "Neuroactive Steroids for the Treatment of Status Epilepticus", Epilepsia (2013), vol. 54, No. 6, pp. 93-98.
Romeo, et al. "Effect of antidepressant treatment on neuroactive steroids in major deprssion" Am. J. Psychiatry 1998; 155:910-913.
"Allopregnanolone for the Treatment of Traumatic Brain Injury" ClinicalTrials.gov, Updated May 22, 2013, pp. 1-4.
"Sage Therapeutics Announces Brexalone Achieves Primary Endpoints in Both Phase 3 Clinical Trials in Postpartum Depression", Press Release, Nov. 9, 2017.

(56) References Cited

OTHER PUBLICATIONS

"Sage Therapeutics Welcome to R&D day 2016", Jan. 1, 2016, pp. 1-143.
"Sage Therapeutics Wins Big in Depression Trial", Press Release, 247Chrislange, Nov. 9, 2017.
Abend et al., "Treatment of refratory status epilepticus: Literature review and a proposed protocol", Pediatric Neurology, vol. 38, No. 6, 2008, pp. 377-390.
Akhondzadeh et al., "Induction of a novel form of hippocampal long-term depression by muscimol: involvement of GABAbut not glutamate receptors", British Journal of Pharmacology (1995) 115, 527-533.
Aladdin et al., "Refractory Status Epilepticus During Pregnancy Secondary to Cavernous Angiona", Epilepsia, vol. 49, No. 9, (2008), pp. 1627-1629.
Allen et al., "Menstrual phase, depressive symptoms, and allopregnanolone during short-term smoking cessation," Experimental and Clinical Psychopharmacology, (2013) 21(6):427-433.
Amin et al., "The interaction of neuroactive steroids and GABA in the development of neuropsychiatric disorders in women", Pharmacology, Biochemistry and Behavior 84 (2006) 635-643.
Anderson et al., "Oxidative/nitrosative stress and immunoinflammatory pathways in depression: Treatment implications," Current Pharmaceutical Design, (2014) 20(25):4126-4161.
Anovadiya et al., "Epilepsy: Novel Therapeutic Targets", Journal of Pharmacology and Pharmacotherapeutics, 2012, pp. 112-117.
Backstrom et al. "Pathogensis in Menstrual cycle-linked CNS disorders", Ann. N.Y. Acad. Sci. 1007: 42-53 (2003).
Baker et al., "Efficacy of progesterone vaginal suppositories in Alleviation of Nervous Symptoms in Patients with Premenstrual Syndrome", Journal of Assisted Reproduction and Genetics, vol. 12, No. 3 1995, pp. 205-209.
Bali, et al. "Multifunctional aspects of allopregnanolone in stress and related disorders", Progress in Neuro-Psychopharmacology & Biological Psychiatry 48 (2014) 64-78.
Bancaud et al., (From the Commission on Classification and Terminology of the International League Against Epilepsy) (Aug. 1981) "Proposal for Revised Clinical and Electroencephalographic Classification of Epileptic Seizures," Epilepsia, 22:489-501.
Bandyopadhyaya et al., "Neurosteroid Analogs. 15. A Comparative Study of the Anesthetic and GABAergic Actions of Alphaxalone, D16-Alphaxalone and Their Corresponding 17-Carbonitrile Analogs, "Bioorganic & Medicinal Chemistry Letters 20:6680-6684 (2010).
Beckley et al., "Progesterone receptor antagonist CDB-4124 increases depression-like behavior in mice without affecting locomotor ability," Psychoneuroendocrinology, (2011) 36:824-833.
Bernardi, et al., "Disadaptive disorders in women: allopregnanolone, a sensitive steroid", Gynecol Endocrinol 2004; 19:344-353.
Biagini et al., "Endogenous neurosteroids modulate epileptogenesis in a model of temporal lobe epilepsy", Experimental Neurology, (2006), vol. 201, pp. 519-524.
Bicikova et al., "Serum concentrations of some neuroactive steroids in women suffering from mixed anxiety-depressive disorder", Neurochemical Research, vol. 25, No. 12, 2000, pp. 1623-1627.
Birzniece et al., "Neuroactive steroid effects of cognitive functions with a focus on the serotonin and GABA systems" Brain Research Reviews 51 (2006) 212-239.
Bleck et al., "Refractory Status Epileptics", Current Opinion in Critical Care, (2005), vol. 11, pp. 117-120.
Bobb et al., "Allopregnanolone to treat refractory status epilepticus," presented at American Clinical Neurophysiology, Society (ACNS) Annual Meeting & Courses, The Westin Peachtree Plaza, Atlanta, Georgia, (Feb. 4-9, 2014) Abstract S26.
Botella et al., "Neuroactive Steroids. 1. Positive Allosteric Modulators of the (g-Aminobutyric Acid)A Receptor: Structure-Activity Relationships of Heterocyclic Substitution at C-21", Journal of Medical Chemistry, 2015, pp. 3500-3511.
Botella et al., "Neuroactive Steroids. 2. 3a-Hydroxy-3b-methyl-21-(4-cyano-1H-pyrazol-1-yl)-19-nor-5b-pregnan-20-one (SAGE-217): A Clinical Next Generation Neuroactive Steroid Positive Allosteric Modulator of the (g-Aminobutyric Acid) A Receptor" Journal of Medical Chemistry, 2017, 10 pp A-J.
Broomall et al., "Pediatric super-refractory status epilipticus treated with allopregnanolone," Ann. Neurol, (2014), 76:911-915.
Brown et al., "A randomized, double-blind, placebo-controlled trial of pregnenolone for bipolar depression," Neuropsychopharmacology, (2014) 39:2867-2873.
Brunn et al., "Combined treatment with diazepam and allopregnanolone reverses tetramethylenedisulfotetramine (TETS)-induced calcium dysregulation in cultured neurons and protects TETS-intoxicated mice against lethal seizures," Neuropharmacology, (2015), 95:332-342.
Burdock, "Encyclopedia of food additives and coloring," Taylor & Francis, 3 Volume Set, (1997), pp. 2410-2413.
Cao et al., "Tetramethylenedisulfotetramine alters Ca2+ dynamics in cultured hippocampal neurons: Mitigation by NMDA receptor blockade and GABAA receptor-positive modulation," Toxicological Sciences, (2012), 130(2):362-372.
Carta, et al. "GABAergic neuroactive steroids: a new frontier in bipolar disorders", Behavioral and Brain Functions 2012, 8:61.
Chen et al., "Ibogaine block of the NMDA receptor: In vitro and in vivo studies," Neuropharmacology, (1996) 35 (4):423-431.
Chiasari et al., "The Influence of Neuroactive Steroid Lipophilicity on GABA Receptor Modulation: Evidence for a Low-Affinity Interaction", Journal of Neurophysiology (2009), vol. 102, pp. 1254-1264.
Claassen et al., "Treatment of Refractory Status Epilepticus with Pentobarbital, Propofol, or Midazolam: A Systematic Review", Epilepsia (2002), vol. 43, No. 2, pp. 146-153.
D'Aquila, et al. ."Dopamine is involved in the anti-depressant-like effect of allopregnanolone in the forced swimming test in female rats", Behavioural Pharmacology 2010, 21:21-28.
Database CAPLUS in STN, Acc. No. 1995:986323, Upasani et al., WO 9521617 A1 (Aug. 17, 1995) (abstract). [Upasani, Ravindra B. "Androstanes and pregnanes for allosteric modulation of GABA receptor, and preparation and therapeutic uses of compounds".].
Database CAPLUS in STN, Acc. No. 1998:112239, Lan, WO 9805337 A1 (Feb. 12, 1998) (abstract). [Lan, Nancy C., "Use of GABA agonists and NMDA receptor antagonists for the treatment of migraine headache".].
De Crescenzo et al., "Selective serotonin reuptake inhibitors (SSRIs) for post-partum depression (PPD): A systematic review of randomized clinical trials", Journal of Affective Disorders, 152-154 (2014) 39-44.
Deligianndis et al., "Peripartum neuroactive steroid and y-aminobutyric acid profiles in women at-risk for postpartum depression," Psychoneuroendocrinology, Accepted Manuscript, (2016), 33p.
Deligiannidis, et al. "GABAergic neuroactive steroids and resting-state functional connectivity in postpartum depression; A preliminary study", Journal of Psychiatric Research 47 (2013) 816-828.
Delorenzo et al., "Epidemiology of Status Epilepticus" Journal of Clinical Neurophysiology (1995), vol. 12, No. 4, pp. 316-325.
Deutsch et al., "Evaluation of In Vivo Interactions in Mice Between Flurazepam and Two Neuroactive Steroids", Pharmacology Biochemistry & Behavior (1996), vol. 55, No. 3, pp. 323-326.
Dhir et al., "Role of neurosteroids in the anticonvulsant activity of midazolam," British Journal of Pharmacology, (2012), 165(8): 2684-2691.
Dhir et al., "Seizure protection by intrapulmonary delivery of midazolam in mice," Neuropharmacology, (2013), 73:425-431.
Dhir et al., "Seizure protection by intrapulmonary delivery of propofol hemisuccinate," The Journal of Pharmacology and Experimental Therapeutics, (2011), 336(1):215-222.
Dorwald, "Side Reactions in Organic Synthesis", 2005, Wiley-VCH, Preface, p. IX.
Drugan et al. "Resilience in shock and swim stress models of depression", Frontiers in Behavorial Neuroscience, Feb. 2013, vol. 7, Article 14.
Dyck et al., "Effects of Deuterium Substitution on the Catabolism of beta-Phenylethylamine: An In Vivo Study". J. Neurochem., vol. 46(2), pp. 399-404 (1986).

(56) References Cited

OTHER PUBLICATIONS

Edgar et al., "CCD-3693: An Orally Bioavailable Analog of the Endogenous Neuroactive Steroid, Pregnanolone, Demonstrates Potent Sedative Hypnotic Actions in the Rat" The Journal of Pharmacology and Experimental Therapeutics (1997) vol. 282, No. 1, pp. 420-429.
Eser et al., "Neuroactive Steroids in Depression and Anxiety Disorders: Clinical Studies", Neuroendocrinology, (2006) 84: pp. 244-254.
Rosenthal et al., "Brexanolone as adjunctive therapy in super-refractory status epilepticus," Annals of Neurology, John Wiley & Sons, (2017), 32pp.
Rossetti et al., "A Randomized Trial for the Treatment of Refractory Status Epilepticus", Neurocritical Care Society (2011), vol. 14, No. 1, pp. 4-10.
Rouge-Pont et al., "The neurosteroid allopregnanolone increases dopamine release and dopaminergic response to morphine in the rat nucleus accumbens", European Journal of Neuroscience, vol. 16, pp. 169-173, 2002.
Runyon et al., "17b-Nitro-5a-androstan-3a-ol and its 3b-methyl derivative: Neurosteroid analogs with potent anticonvulsant and anxiolytic activities", European Journal of Pharmacology 617, (2009), pp. 68-73.
Rupprecht et al.. "Neuroactive steroids; mechanisms of action and neuropsychopharmacological perspectives", Trends Meurosci. (1999) 22, 410-416.
Saady et al., "Case Report: Althesin in Status Epilepticus" Aneasth. Intens. Care (1979), vol. 7, No. 3, pp. 267-270.
Saalmann et al., "Neurosteroids involved in regulating inhibition in the inferior colliculus" J. Neurophysiol 96: 3064-3073, 2006.
Sahin et al., "Outcome of Severe Refractory Status Epilepticus in Children", Epilepsia (2001), vol. 41, No. 11, pp. 1461-1467.
Sanborn et al., "Identifying and managing adverse environmental health effects: 4. Pesticides," CMAJ, (2002) 166 (11):1431-1436.
Santoru et al., "Decreased allopregnanolone induced by hormonal contraceptives is associated with a reduction in social behavior and sexual motivation in female rats," Psychopharmacology, (2014), 14pp.
Saporito et al., "Intravenously Administered Ganaxolone Blocks Diazepam-Resistant Lithium-Pilocarpine-Induced Status Epilepticus in Rats: Comparison with Allopregnanolone", Journal of Pharmacology Exp. Ther. 2019, 368(3), pp. 326-327.
Schiller et al., "Allopregnanolone as a mediator of affective switching in reproductive mood disorders," Psychopharmacology, (2014), 11pp.
Schiller et al., "The role of reproductive hormones in postpartum depression," CNS Spectrums, (2015), 20(1):48-59.
Schule et al., "Neuroactive steroids in Affective Disorders: target for Novel antidepressant or anxiolytic drugs", Neuroscience 191 (2011) p. 55-77.
Schule et al., "The role of allopregnanolone in depression and anxiety", Progress in Neurobiology 113 (2014) 79-87.
Shah et al., "Peripheral WBC Count and Serum Prolactin Level in Various Seizure Types and Nonepileptic Events", Epilepsia (2011), vol. 42, No. 11, pp. 1472-1475.
Shimizu et al., "Allopregnanolone increases mature excitatory synapses along dendrites via protein kinase A signaling ," Neuroscience, (2015), 305:139-145.
Shorvon et al., "The Outcome of Therapies in Refractory and Super-Refractory Convulsive Status Epilepticus and Recommendations for Therapy", Brain (2012), vol. 135, No. 8, pp. 2314-2328.
Shorvon et al., "The Proceedings of the First London Colloquium on Status Epilepticus", University College London, April 12-15 , Epilepsia (2007), vol. 48, No. 8, pp. 1-3.
Shorvon et al., "The Treatment of Super-Refractory Status Epilepticus: A Critical Review of Available Therapies and a Clinical Treatment Protocol", Brain (2011,) vol. 134, No. 10, pp. 2802-2818.
Shu et al., "Characteristics of concatemeric GABM receptors containing alpha4/d subunits expressed in Xenopus pocytes" British Journal of Phannacology (2012) 165, 2228-2243.
Smith et al., "The influence of stress at puberty on mood and learning: Role of the a4136 GABAA receptor," Neuroscience, (2013), 249:192-213.
Stevens et al., "Hormonal Therapy for Epilepsy", Gurr Neurol. Neurosci Rep. 11: 2011, pp. 435-442.
Supplemental European Search Report, European Patent Application No. 14826212.4, dated Feb. 16, 2017.
Timby et al., "Pharmacokinetic and behavioral effects of allopregnanolone in healthy women", Psycopharmacology (2006), vol. 186, pp. 414-424.
Timby et al., "Women with premenstrual dysphoric disorder have altered sensitivity to allopregnanolone over the menstrual cycle compared to controls-a pilot study," Psychopharmacology, (2016), 233:2109-2117.
Tolmacheva et al., "The role of ovarian steroid hormones in the regulation of basal and stress induced absence seizures", Journal of Steroid Biochemistry & Molecular Biology (2007), vol. 104, pp. 281-288.
Tongiani et al., "Sulfobutyl Ether-Alkyl Ether Mixed Cyclodextrin Derivatives With Enhanced Inclusion Ability", Journal of Pharmaceutical Sciences (2009), vol. 98, No. 12, pp. 4769-4780.
Turkmen et al., "Tolerance to Allopregnanolone with Focus on the GABA-A Receptor", British Journal of Pharmacology (2011), vol. 162, pp. 311-327.
Ueda et al., "Evaluation of a Sulfobutyl Ether b-Cyclodextrin as a Aolubilizing/Stabilizing Agent for Several Drugs", Drug Development and Industrial Pharmacy (2008), vol. 24, No. 9, pp. 863-867.
Ungard et al., "Modification of behavioral effects of drugs in mice by neuroactive steroids", Psychopharmacology (2000) 148:336-343.
Upasani et al., "3a-Hydroxy-3B-(phenylethynyl)-5β-pregnan-20-ones: Synthesis and Pharmacological Activity of Neuroactive Steroids with High Affinity for GABAA Receptors", J. Med. Chem. (1997) vol. 40, No. 1, pp. 73-84.
Uzunova et al. "Region-specific dysregulation of allopregnanolone brain contante tin the olfactory bulbectomized rat model of depression", Brain Research 976 (2003) 1-8.
Uzunova et al., "Relevance of endogenous 3a-reduced neurosteroids to depression and antidepressant action", Psycopharmacology (2006) 186: 351-361.
Vaitkevicius et al., "First-in-man allopregnanolone use in super-refractory stats epilepticus". Annals of Clinical and Translational Neurology, vol. 4, No. 6, 2017, pp. 411-414.
Vaitkevicius et al., "Successful allopregnanolone treatment of new onset refractory status epilepticus (Norse) syndrome: First in man experience," Epilepsia, (2013), Abstract p. 114.
Van Broekhoven et al., "Neurosteroids in depression: a review", Psychopharmacology (2003) 165:97-110.
Vanlandingham et al., "Progesterone and its metabolite allopregnanolone differentially regulate hemostatic proteins after traumatic brain injury", Journal of Cerebral Blood Flow & Metabolism (2008), vol. 28, pp. 1786-1794.
Vanover et al., "Behavioral characterization of Co 134444 (3a-hydroxy-21-(1'-imidazolyl)-3b-methoxymethyl-5a-pregnan-20-one), a novel sedative-hypnotic neuroactive steroid", Psychopharmacology (2001), vol. 155, pp. 285-291.
Vanover et al., "Characterization of the Anxiolytic Properties of a Novel Neuroactive Steroid, Co 2-6749 (GMA-839 WAY-141839; 3a, 21-Dihydroxy-3b-trifluoromethyl-19-nor-5b-pregnan-20-one), a Selective Modulator of y-Aminobutyric AcidA Receptors", The Journal of Pharmacology and Experimental Therapeutics, (2000), vol. 295, No. 1, pp. 337-345.
Vanover et al., "Response-Rate Suppression in Operant Paradigm as Predictor of Soporific Potency in Rats and dentification of Three Novel Sedative-Hypnotic Neuroactive Steroids", The Journal of Pharmacology and Experimental Therapeutics, (1999), vol. 291, No. 3, pp. 1317-1323.
Vine et al., "2H-Labelled 3a-Hydroxy-5a-Pregnane-11, 20-Dione and 3a, 21-Dihydroxy-5a-Pregnane-11, 20-Dione 21-Acetate", Journal of Labelled Compounds and Radiopharmaceuticals, vol. IX, No. 4, 1982, pp. 597-604.
Weisberg et al., "Seizure disorders," Essentials of Clinical Neurology, Chapter 11, (1983), pp. 167-175.

(56) References Cited

OTHER PUBLICATIONS

Wirth, "Beyond the HPA axis; progesterone-derived neuroactive steroids in human stress and emotion," Frontiers in Endocrinology (2011) vol. 2, Article 19.
Wolkowitz, et al. "Of Sound Mind and Body; depression, disease, and accelerated aging", Dialogues in Clinical Neuroscience, vol. 13, No. 1, 2011, p. 25-39.
Yunes et al., "Postnatal administration of allopregnanolone modifies glutamate release but not BDNF content in striatum samples of rats prenatally exposed to ethanol", Biomed Research International, vol. 2015, 2015, pp. 1-6.
Zeng et al., "Neurosteroid Analogues. 10. The Effect of Methyl Group Substitution at the C-6 and C-7 Positions on the GABA Modulatory and Anesthetic Actions of (3a,5a) -and (3a, 5b)-3-Hydroxypregnan-20-one", Journal of Medicinal Chemistry, (2005). vol. 48, pp. 3051-3059.
Zhu et al., "Evaluation and comparison of the pharmacokinetic and pharmacodynamic properties of allopregnanolone and pregnanolone at induction of anaesthesia in the male rat", British Journal of Anaesthesia (2001,) vol. 86, No. 3, pp. 403-412.
Zia et al., "Effect of Alkyl Chain and Degree of Substitution on the Complexation of Sulfoalkyl Ether b-Cyclodextrins with Steroids", Journal of Pharmaceutical Sciences (1996), vol. 86, No. 2, pp. 220-224.
Zia et al., "Effect of Cyclodextrin Charge on Complexation of Neutral and Charged Substrates: Comparison of (SBE) 7M-b-CD to HP-b-CD", Pharmaceutical Research (2001) vol. 18, No. 5, pp. 667-673.
Zia et al., "Thermodynamics of Binding of Neutral Molecules to Sulfobutyl Ether b-Cyclodextrins (SBE-b-CDs):The Effect of Total Degree of Substitution", Pharmaceutical Research (2000), vol. 17, No. 8, pp. 936-941.
Zolkowska et al., "Anticonvulsant Activity of Intravenous and Intramuscular Allopregnenalone". 1-25. 26a-30a. 26b-30b American Epilepsy Society: 2012 Annual Meeting Abstracts.
Zolkowska et al., "Anticonvulsant activity of intravenous and intramuscular allopregnenalone," American Epilepsy Society, (Poster), UC Davis, University of California, (2012), 1 page.
Zonana et al.,"The Neurobiology of Postpartum Depression", CNS Spectrums, (2005), pp. 792-799, 805.
Zsuzsa, "Neurological and psychiatric aspects of some endocrine diseases. The role of neurosteroids and neuroactive steroids", Medical Journal (2007), 148(41): pp. 1929-1937, machine translated into English.
International Search Report and Written Opinion for corresponding International Application No. PCT/US2013/22772 dated Mar. 27, 2013.
International Search Report and Written Opinion for corresponding International Application No. PCT/US2013/56062 dated Jan. 29, 2014.
International Search Report and Written Opinion for corresponding International Application No. PCT/US2015/48937 dated Feb. 5, 2016.
International Search Report and Written Opinion for Corresponding International Application No. PCT/US2016/018748 dated Aug. 29, 2016.
International Search Report and Written Opinion for corresponding International Application No. PCT/US2016/026705 dated Aug. 19, 2016.
International Search Report and Written Opinion for corresponding International Application No. PCT/US2016/038195 dated Oct. 20, 2016.
International Search Report and Written Opinion for corresponding International Application No. PCT/US2017/021325 dated May 22, 2017.
International Search Report and Written Opinion for corresponding International Application No. PCT/US2018/050444 dated Dec. 3, 2018.
International Search Report and Written Opinion for International Application No. PCT/CN2013/074312 dated Jan. 23, 2014.
International Search Report and Written Opinion for International Application No. PCT/CN2013/074319 dated Jan. 23, 2014.
International Search Report and Written Opinion for International Application No. PCT/CN2013/074323 dated Jan. 30, 2014.
International Search Report and Written Opinion for International Application No. PCT/CN2013/074325 dated Jan. 23, 2014.
International Search Report and Written Opinion for International Application No. PCT/CN2014/075585 dated Aug. 1, 2014.
International Search Report and Written Opinion for International Application No. PCT/CN2014/075593 dated Jul. 22, 2014.
International Search Report and Written Opinion for International Application No. PCT/CN2014/075594 dated Jul. 16, 2014.
International Search Report and Written Opinion for International Application No. PCT/CN2014/075600 dated Jul. 29, 2014.
International Search Report and Written Opinion for International Application No. PCT/US14/47246, dated Jan. 22, 2015.
International Search Report for International Application No. PCT/US2012/060136 dated Mar. 27, 2013.
Irwin et al., "Allopregnanolone preclinical acute pharmacokinetic and pharmacodynamic studies to predict tolerability and efficacy for alzheimer's disease", Plos One, vol. 10, No. 6, 2015, pp. 1-31.
Jain et al., "Hygroscopicity, phase solubility and dissolution of various substituted sulfobutylether b-cyclodextrins (SBE) and danazol-SBE inclusion complexes", International Journal of Pharmaceutics (2001), vol. 212, pp. 177-186.
Jin et al., "A sensitive and selective LC-differential mobility-mass spectrometric analysis of allopregnanolone and pregnanolone in human plasma", Analytical and Bioanalytical Chemistry, vol. 405, No. 29, 2013, pp. 1-23.
Johnson et al., "Deuterium Labelled Steroid Hormones: Syntheses and Applications in Quantitation and Endocrinology", Journal of Steroid Biochemistry, vol. 14, 1981, pp. 793-800.
Jones, "Post-partum depression-a glimpse of light in the darkness?", Published online Jun. 12, 2017, 2 pages.
Kaminski et al., "Allopregnanolone analogs that positively modulate GABAA receptors protect against partial seizures induced by 6-Hz electrical stimulation in mice," Epilepsia, (2004), 45(7):864-867.
Kanes et al., "Brexanolone (SAGE-547 injection) in post partum depression: a randomised controlled trial", The Lancet, 2017; vol. 390, Issue 10093, pp. 480-489.
Kanes et al., "Open-label, proof-of-concept study of brexanolone in the treatment of severe postpartum depression", Hum Psychopharmacol Clin Exp. (2017).
Kanto, "Midazolam: The first water-soluble benzodiazepine pharmacology, pharmacokinetics and efficacy in insomnia and anesthesia", Pharmacotherapy, (1985), 5(3): 138-155.
Kask et al., "Allopregnanolone has no effect on startle response and prepulse inhibition of startle response in patients with premenstrual dysphoric disorder or healthy controls", Pharmacology, Biochemistry and Behavior (2009), vol. 92, pp. 608-613.
Kask et al., "Allopregnanolone impairs episodic memory in healthy women", Psycopharmacology (2008), vol. 199, pp. 161-168.
Kaura et al., "The Progesterone metabolite allopregnanolone potentiates GABAA rceptor-mediated inhibition of 5-HT neuronal activity", European Neuropsychopharmacology, (2007), 17, pp. 108-115.
Khanna et al., "Nanotoxicity: An interplay of oxidative stress, inflammation and cell death," nanomaterials, (2015), 5:1163-1180.
Khisti et al., "Serotonergic agents modulate anti-depressant-like effect of the neurosteroid 3a-hydroxy-5a-pregnan-20-one in mice" Brain Research 865 (2000) 291-300.
Kim et al., "Modulation of presynaptic GABAA receptors by endogenous neurosteroids", British Journal of Pharmacology (2011), vol. 164, pp. 1698-1710.
Kimmel et al., "Oxytocin receptor DNA methylation inpostpartum depression," Psychoneuroendocrinology, (2016), 69:150-160.
Klatzkin et al. "Associations of histories of depression and PMDD diagnosis with allopregnanolone concentrations following the oral administration of micronized progesterone", Psychoneuroendocrinology (2006) 31, 1208-1219.
Klatzkin et al., "Histories of depression, allopregnanolone responses to stress, and premenstrual symptoms in women:", Biological Psychology 71 (2006) 2-11.

(56) References Cited

OTHER PUBLICATIONS

Kokate et al., "Anticonvulsant Activity of Neurosteroids: Correlation with g-Aminobutyric Acid-Evoked Chloride Current Potentiation", The Journal of Pharmacology and Experimental Therapeutics (1994), vol. 270, No. 3, pp. 1223-1229.
Kokate et al., "Convulsant actions of the neurosteroid pregnenolone sulfate in mice", Brain Research (1999), vol. 831, pp. 119-124.
Kokate et al., "Neuroactive Steroids Protect Against Pilocarpine- and Kainic Acid-induced Limbic Seizures and Status Epilepticus in Mice", Neuropharmacology (1996) vol. 35, No. 8, pp. 1049-1056.
Kramer, "Early Ketamine to Treat Refractory Status Epilepticus" Neurocrit. Care (2012), vol. 16, pp. 299-305.
Kushner et al., "Pharmacological uses and perspectives of heavy water and deuterated compounds". Candian Journal Physiology and Pharmacology, vol. 77, pp. 79-88 (1999).
Lahiani-Skiba et al., "Solubility and Dissolution Rate of Progesterone-Cyclodextrin-Polymer Systems", Drug Development and Industrial Pharmacy (2006), vol. 32, pp. 1043-1058.
Larsen et al., "Phase Solubility and Structure of the Inclusion Complexes of Prednisolone and 6a-Methyl Prednisolone with Various Cyclodextrins", Journal of Pharmaceutical Sciences (2005), vol. 94, No. 3, pp. 507-515.
Leroy et al., "Pharmacological plasticity of GABAA receptors at dentate gyrus synapses in a rat model of temporal lobe epilepsy", J. Physol. (2004), vol. 557, No. 2, pp. 473-487.
Li et al., "Nanoparticle-induced pulmonary toxicity," Experimental Biology and Medicine, (2010), 235:1025-1033.
Lonsdale et al., "The Anticonvulsant effects of allopregnanolone against amygdala-kindled seizures in female rats", Neuroscience Letters (2007), vol. 411, pp. 147-151.
Lossin et al., "Allopregnanolone treatment in a rat pediatric status epilepticus model: Comparison with diazepam", American Epilepsy Society (2012), (Abst. 3.220).
MacKenzie et al., "Neurosteriods and GABAergic signaling in health and disease", BioMol Concepts 2013; 4(1): 29-42.
Madl et al., "Nanoparticles, lung injury, and the role of oxidant stress," Annu Rev Physiol., (2014), 76:447-465.
Maguire et al., "GABAAR plasticity during pregnancy relevance to postpartum Depression," Neuron, (2008), 59:207-213.
Eser et al., "Neuropsychopharmacological properties of neuroactive steroids in depression and anxiety disorders", Psychopharmacolody, (2006) 186: pp. 373-387.
Evans, et al. "Allopregnanolone regulates neurogensis and depressive/ anxiety-like behaviour in social isolation rodent model of chronic stress", Neuropharmacology 63 (2012) 1315-1326.
Extended European Search Report for application PCT/CN2014075593 dated Aug. 26, 2016.
Extended European Search Report for application PCT/CN2014075594 dated Aug. 26, 2016.
Extended European Search Report for European Application No. 13740743.3 dated Jan. 14, 2016.
Extended European Search Report for European Application No. 13830765.7 dated Jan. 12, 2016.
Extended European Search Report for European Application No. 13857993.3 dated May 2, 2016.
Finn et al., "The Estrus Cycle, Sensitivity to Convulsants and the Anticonvulsant Effect of Neuroactive Steroid", The Journal of Pharmacology and Experimental Therapeutics (1994), vol. 271, pp. 164-170.
Fitelson et al., "Treatment of postpartum despression: clinical, psychological and pharmacological options", International Journal of Women's Health, 2011, pp. 1-14.
Foster, "Deuterium isotope effects in studies of drug metablosim". Trends in Pharmacological Sciences, vol. 5, pp. 524-527 (Abstract) (1984).
Frank et al., "Neuroprotective effects of allopregnenolone on hippocampal irreversible neurotoxicity in vitro", Prog. Neuropsychopharmacol. & Biol Psychiat 2000, vol. 24, pp. 1117-1126.

Freeman et al., "Allopregnanolone levels and sympotom improvement in severe premenstrual syndrome", J. Clin. Psychopharmacol 2002; 22:516-520.
Frye et al. "Hippocampal 3a,5a-THP may alter depressive behavior of pregnant an lactating rats", Pharmacology, Biochemistry and Behavior 78 (2004) 531-540.
Frye et al., "Changes in Progesterone metabolites in the hippocampus can modulate open field and forced swim test behavior of proestrous rats", Hormones and Behavior 41, 306-315 (2002).
Frye et al., "Infusion of 3a,5a-THP to the pontine reticular formation attenuates PTZ-induced seizures", Brain Research (2000), vol. 881, pp. 98-102.
Frye, "The neurosteroid 3-a, 5 a-THP has antiseizure and possible neuroprotective effects in an animal model of epilepsy," Brain Research, (1995), 696:113-120.
Frye, et al., "Effects and mechanism of 3a,5a,-THP on emotion, motivation, and reward functions involving pregnane xenobiotic receptor", Frontiers in Neuroscience (2012), vol. 5, Article 136, pp. 1-18.
Galvin et al., "Midazolam: an effective intravenous agent for seizure control," Archives of emergency medicine, (1987), 4:169-172.
Gasior et al., "Anticonvulsant and behaviorial effects of neuroactive steroids alone and in conjunction with diazepam", The Journal of Pharmacology and Experimental Therapeutics (1997), vol. 282, No. 2, pp. 543-553.
Gasior et al., "Neuroactive steroids: potential therapeutic use in neurological and psychiatric disorders", Trends in Pharmacological Science, (1999), vol. 20, No. 3, pp. 107-112.
Gaynes et al., "Perinatal Depression: Prevalence, Screening Accuracy, and Screening Outcomes", Evidence Report/Technology Assessment, (2005), No. 119, pp. 1-8.
Gilbert et al., "3a-reduced neuroactive steroids and their precursors during pregnancy and the postpartum period", Gynecol Endocrinol., (2005), 21(5): pp. 268-279.
Girdler et al. "Neurosteroids in the context of stress: Implications for depressive disorders", Pharmacology & Therapeutics 116 (2007) 125-139.
Griffin et al., "Current perspectives on the role of neurosteroids in PMS and depression", International Review of Neurobiology, vol. 46, 2001, pp. 479-492.
Guidotti et al., "The socially-isolated mouse: a model to study the putative role of allopregnanolone and 5a-dihydroprogesterone in psychiatric disorders", Brain Research Reviews 37 (2001) 110-115.
Gul et al., "Sterols and the phytosterol content in oilseed rape (Brassica napus L.)", Journal of Cell and Molecular Biology (2006), 5: 71-79.
Haas et al., "Ketamine: A Review of Its Pharmacologic Properties and Use in Ambulatory Anesthesia", Anesthesia, Anesthesia Progress, The American Dental Society of Anesthesiology (1992), vol. 39, pp. 61-68.
Hanley et al., "Use of midazolam in the treatment of refractory status epilepticus". Clinical Therapeutics, (1998), 20(6):1093-1105.
Hardoy et al. "The link between neurosteroids and syndromic/ syndromal components of the mood spectrum disorders in women during the premenstrual phase", Clinical Practice and Epidemiology in Mental Health 2008, 4:3.
Hardoy, et al., "Increased neuroactive steroids concentrations in women with bipolar disorder or major depressive disorder", J. Clin Psychopharmacol 2006;26:379-384.
Harrison et al., "Structure-Activity Relationships for Steroid Interaction with the y-Aminobutyric AcidA Receptor Complex" The Journal of Pharmacology and Experimental Therapeutics (1987) vol. 241, No. 1, pp. 346-353.
Haut et al., "Seizure clustering during epilepsy monitoring", Epilepsia, (2002), 43(7): 711-715.
Haut, "Seizure clustering", Epilepsy & Behavior, (2006), 8:50-55.
Haut, "Seizure Clusters: characteristics and treatment," Current Opin. Neurol., (2015), 28(2):143-150, Abstract only.
Hawkinson et al., "3a-Hydroxy-3b-trifluoromethyl-5a-pregnan-20-one (Co Feb. 1970): A Partial Agonist at the Neuroactive Steroid Site of the y-Aminobutyric acidA Receptor" Molecular Pharmacology (1996) vol. 49, pp. 897-906.

(56) References Cited

OTHER PUBLICATIONS

Hawkinson et al., "Correlation of Neuroactive Steroid Modulation of [35S]t-Butylbicyclophosphorothionate and [3H] Flunitrazepam Binding and y-Aminobutyric AcidA Receptor Function", Molecular Pharmacology (1994) vol. 46, pp. 977-985.

Hawkinson et al., "Substituted 3b-Phenylethynyl Derivatives of 3a-Hydroxy-5a-pregnan-20-one: Remarkably Potent Neuroactive Steroid Modulators of y-Aminobutyric AcidA Receptors", The Journal of Pharmacology and Experimental Therapeutics(1998), vol. 287, No. 1, pp. 198-207.

Hay et al., "Pathways to Violence in the Children of Mothers Who Were Depressed Postpartum", Developmental Psychology, 2003, vol. 39, No. 6, pp. 1083-1094.

He J et al., "Allopregnanolone facilitates spatial learning after traumatic brain injury", Abstracts of the Annual Meeting of the Society for Neuroscience (2000) p. 2296.

Hellgren et al., "Low serum allopregnanolone is associated with symptoms of depression in late pregnancy," Neuropsychobiology, (2014), 69:147-153.

Hincal, "Recent advances in drug delivery using amphiphilic cyclodextrin nanoparticles", European Journal of Pharmaceutical Sciences (2005), vol. 23S1, pp S3-S4.

Hogenkamp et al., "Synthesis and in Vitro Activity of 3b-Substituted-3a-hydroxypregnan-20-ones: Allosteric Modulators of the GABAA Receptor", Journal of Medicinal Chemistry, (1997), vol. 40, pp. 61-72.

Hu et al., "Neurosteroid Analogues: Structure-Activity Studies of Benz(e] indene Modulators of GABAA Receptor Function. 1. The Effect of 6-Melhyl Substitution on the Electrophysiological Activity of 7-Substituted Benz[e]indene-3-carbonitriles". Journal of Medicinal Chemistry, (1993), pp. 3956-3967.

Huber, et al. "Effect of an oral contrceptive with chlormadinone Acetate on depressive mood", Clin Drug Invest 2008: 28 (12): 783-791.

Hunter et al., "Status Epilepticus: A Review, With Emphasis on Refractory Cases" Can. J. Neurol. Sci. (2012), vol. 39, pp. 157-169.

International Search Report and Written Opinion (Declaration of non-establishment of International Search Report) for corresponding International Application No. PCT/US2011/062888 dated Jun. 15, 2012.

International Search Report and Written Opinion for corresponding International Application No. PCT/US13/56062 dated Jan. 29, 2014.

International Search Report and Written Opinion for corresponding International Application No. PCT/US2012/056509 dated Dec. 27, 2012.

International Search Report and Written Opinion for corresponding International Application No. PCT/US2013/054562 dated Jan. 13, 2014.

International Search Report and Written Opinion for corresponding International Application No. PCT/US2013/072351 dated Mar. 17, 2014.

Rajewski et al. J Pharm Sci. Aug. 1995;84(8): 927-32 (Year: 1995).

Bengtsson, S.K., et al., "Chronic Allopregnanolone Treatment Accelerates Alzheimer's Disease Development in ABPPSwePSEN111E9 Mice", Journal of Alzheimer's Disease 31 (2012), pp. 71-84, published in Apr. 2012.

Grant, K.A. et al. Neuroactive steroid stereospecificity of ethanol-like discriminative stimulus effects in monkeys. J. Pharmacol, Exp, The: 326, 354-361 ,doi:10.1124/jpet.108.137315 published Apr. 24, 2008.

Irwin et al. "Frontiers in therapeutic development of allopregnanolone for Alzheimer's disease and other neurological disorders." Front. Cell. Neurosci. 8:203. doi: 10.3389/fnce1.2014.00203 published Jul. 30, 2014.

\* cited by examiner

Table 1.

| Time point (hr) | % Difference Plasma IM relative to IV |
|---|---|
| 0.5 | 838.26% |
| 1 | 916.52% |
| 2 | 671.92% |

NEUROACTIVE STEROID FORMULATIONS AND METHODS OF TREATING CNS DISORDERS

CROSS-REFERENCE TO RELATED APPLICATIONS

This application is a divisional of U.S. Ser. No. 15/649,583, filed Jul. 13, 2017, which is a continuation of U.S. Ser. No. 14/374,080, filed Jul. 23, 2014, which is a national stage application under 35 U.S.C. § 371 of International Application No. PCT/US2013/022772, filed Jan. 23, 2013, published as International Publication No. WO2013/112605 on Aug. 1, 2013, which claims priority from U.S. Ser. No. 61/589,740 filed Jan. 23, 2012, the teachings of each of which are incorporated herein.

FIELD OF THE INVENTION

The present invention generally relates to neuroactive steroid formulations, particularly allopregnanolone, for the treatment of CNS injuries and/or diseases.

BACKGROUND OF THE INVENTION

Central nervous system (CNS) related disorders include disorders which affect either or both the brain or spinal cord. CNS related disorders can include, e.g., a traumatic injury, e.g., a traumatic brain injury. A traumatic injury to the CNS is characterized by a physical impact to the central nervous system, e.g., a traumatic brain injury. Status epilepticus (SE) is another example of a CNS related disorder, e.g., generalized status epilepticus, early status epilepticus, established status epilepticus, refractory status epilepticus, super-refractory status epilepticus, non-convulsive status epilepticus, e.g., complex partial status epilepticus.

SUMMARY OF THE INVENTION

The disclosure features, inter alia, compositions comprising a neuroactive steroid, e.g., allopregnanolone, and optionally a cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®. The disclosure also features, inter alia, methods of treating a subject having a CNS disorder, e.g., a traumatic brain injury, status epilepticus, e.g., refractory convulsive status epilepticus, non-convulsive status epilepticus, the methods comprising administering to the subject a composition described herein, e.g., a neuroactive steroid, e.g., allopregnanolone, and optionally a cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®.

In one aspect, the disclosure features a composition, the composition comprising a neuroactive steroid, e.g., allopregnanolone, and cyclodextrin, e.g., a neuroactive steroid, e.g., allopregnanolone, and optionally a cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, complex. a β-cyclodextrin, e.g., a sulfo butyl ether β-cyclodextrin, e.g., a β-cyclodextrin, e.g., a sulfo butyl ether β-cyclodextrin, e.g., CAPTISOL®, complex.

In some embodiments, the neuroactive steroid is a progestin derivative, e.g., allopregnanolone. In an embodiment, the neuroactive steroid is allopregnanolone.

In some embodiments, the cyclodextrin is a β-cyclodextrin. In an embodiment, the cyclodextrin is a sulfo butyl ether β-cyclodextrin. In an embodiment, the cyclodextrin is CAPTISOL®. In some embodiments, the cyclodextrin is a β-cyclodextrin disclosed in U.S. Pat. Nos. 5,874,418; 6,046,177; or 7,635,733, which are herein incorporated by reference.

In some embodiments, the neuroactive steroid is a progestin derivative, e.g., allopregnanolone, and the cyclodextrin is a β-cyclodextrin. In an embodiment, the neuroactive steroid is allopregnanolone and the cyclodextrin is CAPTISOL®.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated for parenteral administration. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 1.5 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 5 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 15 mg/mL.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration between 25-400 mg/mL; 25-300 mg/mL; 25-200 mg/mL; 25-100 mg/mL; 25-50 mg/mL; 50-400 mg/mL; 50-300 mg/mL; 60-400 mg/mL; 60-300 mg/mL; 150-400 mg/mL;

150-300 mg/mL; 200-300 mg/mL; 200-400 mg/mL; 30-100 mg/mL; 300-400 mg/mL; 30-100 mg/mL; 45-75 mg/mL; 50-70 mg/mL; 55-65 mg/mL; or 50-60 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration of 25 mg/mL; 30 mg/mL; 35 mg/mL; 40 mg/mL; 45 mg/mL; 50 mg/mL; 55 mg/mL; 60 mg/mL; 65 mg/mL; 70 mg/mL; 75 mg/mL; 80 mg/mL; 85 mg/mL; 90 mg/mL, 95 mg/mL; 100 mg/mL; 150 mg/mL; 200 mg/mL; 250 mg/mL; 300 mg/mL; 350 mg/mL; or 400 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration of 60 mg/ml. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising between 2.5-40%, 2.5-30%, 2.5-20%, 2.5-10%, 5-40%, 5-30%, 5-20%, 5-10%, 6-40%, 6-30%, 6-20%, 6-10%, 10-40%, 10-30%, 10-20%, 20-40%, 20-30%, 25-40%, 25-30%, 3-10%, 4.5-7.5%, 5-7%, 5.5-6.5% of the cyclodextrin, e.g., CAPTISOL®. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 2.5%, 3%, 4%, 4.5%, 5%, 5.5%, 6%, 6.5%, 7%, 7.5%, 8%, 8.5%, 9%, 9.5%, 10%, 15%, 20%, 25%, 30%, 35% or 40% of the cyclodextrin, e.g., CAPTISOL®. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 6% of the cyclodextrin. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 15% of the cyclodextrin. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 30% of the cyclodextrin.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and the cyclodextrin, e.g., a β-cyclodextrin, e.g., a sulfo butyl ether β-cyclodextrin, e.g., CAPTISOL®, at a concentration between 25-400 mg/mL; 25-300 mg/mL; 25-200 mg/mL; 25-100 mg/mL; 25-50 mg/mL; 50-400 mg/mL; 50-300 mg/mL; 60-400 mg/mL; 60-300 mg/mL; 150-400 mg/mL; 150-300 mg/mL; 200-300 mg/mL; 200-400 mg/mL; 30-100 mg/mL; 300-400 mg/mL; 30-100 mg/mL; 45-75 mg/mL; 50-70 mg/mL; 55-65 mg/mL; or 50-60 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and the cyclodextrin, e.g., a β-cyclodextrin, e.g., a sulfo butyl ether β-cyclodextrin, e.g., CAPTISOL®, at a concentration of 25 mg/mL; 30 mg/mL; 35 mg/mL; 40 mg/mL; 45 mg/mL; 50 mg/mL; 55 mg/mL; 60 mg/mL; 65 mg/mL; 70 mg/mL; 75 mg/mL; 80 mg/mL; 85 mg/mL; 90 mg/mL, 95 mg/mL; 100 mg/mL; 150 mg/mL; 200 mg/mL; 250 mg/mL; 300 mg/mL; 350 mg/mL; or 400 mg/mL.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and between 2.5-40%, 2.5-30%, 2.5-20%, 2.5-10%, 5-40%, 5-30%, 5-20%, 5-10%, 6-40%, 6-30%, 6-20%, 6-10%, 10-40%, 10-30%, 10-20%, 20-40%, 20-30%, 25-40%, 25-30%, 3-10%, 4.5-7.5%, 5-7%, 5.5-6.5% of the cyclodextrin, e.g., CAPTISOL®. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and 2.5%, 3%, 4%, 4.5%, 5%, 5.5%, 6%, 6.5%, 7%, 7.5%, 8%, 8.5%, 9%, 9.5%, 10%, 15%, 20%, 25%, 30%, 35% or 40% of the cyclodextrin, e.g., CAPTISOL®.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and the cyclodextrin, e.g., a β-cyclodextrin, e.g., a sulfo butyl ether β-cyclodextrin, e.g., CAPTISOL®, at a concentration between 25-400 mg/mL; 25-300 mg/mL; 25-200 mg/mL; 25-100 mg/mL; 25-50 mg/mL; 50-400 mg/mL; 50-300 mg/mL; 60-400 mg/mL; 60-300 mg/mL; 150-400 mg/mL; 150-300 mg/mL; 200-300 mg/mL; 200-400 mg/mL; 30-100 mg/mL; 300-400 mg/mL; 30-100 mg/mL; 45-75 mg/mL; 50-70 mg/mL; 55-65 mg/mL; or 50-60 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and the cyclodextrin, e.g., CAPTISOL® at a concentration of 25 mg/mL; 30 mg/mL; 35 mg/mL; 40 mg/mL; 45 mg/mL; 50 mg/mL; 55 mg/mL; 60 mg/mL; 65 mg/mL; 70 mg/mL; 75 mg/mL; 80 mg/mL; 85 mg/mL; 90 mg/mL; 95 mg/mL; 100 mg/mL; 150 mg/mL; 200 mg/mL; 250 mg/mL; 300 mg/mL; 350 mg/mL; or 400 mg/mL.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and between 2.5-40%, 2.5-30%, 2.5-20%, 2.5-10%, 5-40%, 5-30%, 5-20%, 5-10%, 6-40%, 6-30%, 6-20%, 6-10%, 10-40%, 10-30%, 10-20%, 20-40%, 20-30%, 25-40%, 25-30%, 3-10%, 4.5-7.5%, 5-7%, 5.5-6.5% of the cyclodextrin, e.g., CAPTISOL®. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and 2.5%, 3%, 4%, 4.5%, 5%, 5.5%, 6%, 6.5%, 7%, 7.5%, 8%, 8.5%, 9%, 9.5%, 10%, 15%, 20%, 25%, 30%, 35% or 40% of the cyclodextrin, e.g., CAPTISOL®.

In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 1.5 mg/mL, and the cyclodextrin, e.g., a β-cyclodextrin, e.g., a sulfo butyl ether β-cyclodextrin, e.g., CAPTISOL®, at a concentration of 6%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 10 mg/mL, and the cyclodextrin, e.g., a β-cyclodextrin, e.g., a sulfo butyl ether β-cyclodextrin, e.g., CAPTISOL®, at a concentration of 6%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 15 mg/mL, and the cyclodextrin, e.g., a β-cyclodextrin, e.g., a sulfo butyl ether β-cyclodextrin, e.g., CAPTISOL®, at a concentration of 6%.

In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 1.5 mg/mL, and the cyclodextrin, e.g., a β-cyclodextrin, e.g., a sulfo butyl ether β-cyclodextrin, e.g., CAPTISOL®, at a concentration of 15%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 10 mg/mL, and the cyclodextrin, e.g., a β-cyclodextrin, e.g., a sulfo butyl ether β-cyclodextrin, e.g., CAPTISOL®, at a concentration of 15%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 15 mg/mL, and the cyclodextrin, e.g., a β-cyclodextrin, e.g., a sulfo butyl ether β-cyclodextrin, e.g., CAPTISOL®, at a concentration of 15%.

In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 1.5 mg/mL, and the cyclodextrin, e.g., a β-cyclodextrin, e.g., a sulfo butyl ether β-cyclodextrin, e.g., CAPTISOL®, at a concentration of 30%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 10 mg/mL, and the cyclodextrin, e.g., a β-cyclodextrin, e.g., a sulfo butyl ether β-cyclodextrin, e.g., CAPTISOL®, at a concentration of 30%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 15 mg/mL, and the cyclodextrin, e.g., a β-cyclodextrin, e.g., a sulfo butyl ether β-cyclodextrin, e.g., CAPTISOL®, at a concentration of 30%.

In some embodiments, the allopregnanolone and CAPTISOL® complex is formulated as an aqueous composition with a pH between 3-10, 4-9, 4-8, 4-7, 4-6, 4-5, 5-9, 5-8, 5-7, 5-6, 4.5-7.5, or 5.5-7.5. In some embodiments, the allopregnanolone and CAPTISOL® complex is formulated as an aqueous composition with a pH about 3, 3.5, 4, 4.5, 5, 5.5, 6, 6.5, 7, 7.5, 8, 8.5, or 9. In an embodiment, the allopregnanolone and CAPTISOL® complex is formulated as an aqueous composition with a pH about 6.

In one aspect, the disclosure features a composition, the composition comprising a neuroactive steroid, e.g., allopregnanolone, and cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, complex, wherein the composition comprises less than 100 ppm of a phosphate, and the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, has an absorption of less than 0.2 A.U. due to a drug-degrading agent, as determined by UV/vis spectrophotometry at a wavelength of 245 nm to 270 nm for an aqueous solution comprising 300 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, has an absorption of less than 0.2 A.U. due to a color forming agent, as determined by UV/vis spectrophotometry at a wavelength of 320 nm to 350 nm for an aqueous solution comprising 500 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, further comprises: less than 20 ppm of a sulfoalkylating agent; less than 0.5% wt. of an underivatized cyclodextrin; less than 1% wt. of an alkali metal halide salt; and less than 0.25% wt. of a hydrolyzed sulfoalkylating agent.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, has an absorption of less than 0.2 A.U. due to a drug-degrading agent, as determined by UV/vis spectrophotometry at a wavelength of 245 nm to 270 nm for an aqueous solution comprising 500 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, further comprises: less than 50 ppm of a phosphate; less than 10 ppm of a sulfoalkylating agent; less than 0.2% wt. of an underivatized cyclodextrin; less than 0.5% wt. of an alkali metal halide salt; and less than 0.1% wt. of a hydrolyzed sulfoalkylating agent; and wherein the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, has an absorption of less than 0.2 A.U. due to the color-forming agent, as determined by U/vis spectrophotometry at a wavelength of 320 nm to 350 nm for an aqueous solution comprising 500 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, further comprises: less than 10 ppm of a phosphate; less than 2 ppm of a sulfoalkylating agent; less than 0.1% wt. of an underivatized cyclodextrin; less than 0.2% wt. of an alkali metal halide salt; and less than 0.08% wt. of a hydrolyzed sulfoalkylating agent; and wherein the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, has an absorption of less than 0.1 A.U. due to the color-forming agent, as determined by UV/vis spectrophotometry at a wavelength of 320 nm to 350 nm for an aqueous solution comprising 500 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, further comprises: less than 5 ppm of a phosphate; less than 0.1% wt. of an alkali metal halide salt; and less than 0.05% wt. of a hydrolyzed sulfoalkylating agent.

In some embodiments, the neuroactive steroid is a progestin derivative, e.g., allopregnanolone. In an embodiment, the neuroactive steroid is allopregnanolone.

In some embodiments, the cyclodextrin is a β-cyclodextrin. In an embodiment, the cyclodextrin is a sulfo butyl ether β-cyclodextrin. In an embodiment, the cyclodextrin is CAPTISOL®. In some embodiments, the cyclodextrin is a β-cyclodextrin disclosed in U.S. Pat. Nos. 5,874,418; 6,046,177; and 7,635,733, which are herein incorporated by reference.

In some embodiments, the neuroactive steroid is a progestin derivative, e.g., allopregnanolone, and the cyclodextrin is a β-cyclodextrin. In an embodiment, the neuroactive steroid is allopregnanolone and the cyclodextrin is CAPTISOL®.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated for parenteral administration. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 1.5 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 5 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 15 mg/mL.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration between 25-400 mg/mL; 25-300 mg/mL; 25-200 mg/mL; 25-100 mg/mL; 25-50 mg/mL; 50-400 mg/mL; 50-300 mg/mL; 60-400 mg/mL; 60-300 mg/mL; 150-400 mg/mL; 150-300 mg/mL; 200-300 mg/mL; 200-400 mg/mL; 30-100 mg/mL; 300-400 mg/mL; 30-100 mg/mL; 45-75 mg/mL; 50-70 mg/mL; 55-65 mg/mL; or 50-60 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration of 25 mg/mL; 30 mg/mL; 35 mg/mL; 40 mg/mL; 45 mg/mL; 50 mg/mL; 55 mg/mL; 60 mg/mL; 65 mg/mL; 70 mg/mL; 75 mg/mL; 80 mg/mL; 85 mg/mL; 90 mg/mL, 95 mg/mL; 100 mg/mL; 150 mg/mL; 200 mg/mL; 250 mg/mL; 300 mg/mL; 350 mg/mL; or 400 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration of 60 mg/ml. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising between 2.5-40%, 2.5-30%, 2.5-20%, 2.5-10%, 5-40%, 5-30%, 5-20%, 5-10%, 6-40%, 6-30%, 6-20%, 6-10%, 10-40%, 10-30%, 10-20%, 20-40%, 20-30%, 25-40%, 25-30%, 3-10%, 4.5-7.5%, 5-7%, 5.5-6.5% of the cyclodextrin, e.g., CAPTISOL®. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 2.5%, 3%, 4%, 4.5%, 5%, 5.5%, 6%, 6.5%, 7%, 7.5%, 8%, 8.5%, 9%, 9.5%, 10%, 15%, 20%, 25%, 30%, 35% or 40% of the cyclodextrin, e.g., CAPTISOL®. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 6% of the cyclodextrin. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 15% of the cyclodextrin. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 30% of the cyclodextrin.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and the cyclodextrin, e.g., a β-cyclodextrin, e.g., a sulfo butyl ether β-cyclodextrin, e.g., CAPTISOL®, at a concentration between 25-400 mg/mL; 25-300 mg/mL; 25-200 mg/mL; 25-100 mg/mL; 25-50 mg/mL; 50-400 mg/mL; 50-300 mg/mL; 60-400 mg/mL; 60-300 mg/mL; 150-400 mg/mL; 150-300 mg/mL; 200-300 mg/mL; 200-400 mg/mL; 30-100 mg/mL; 300-400 mg/mL; 30-100 mg/mL; 45-75 mg/mL; 50-70 mg/mL; 55-65 mg/mL; or 50-60 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL, 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and the cyclodextrin, e.g., a β-cyclodextrin, e.g., a sulfo butyl ether β-cyclodextrin, e.g., CAPTISOL®, at a concentration of 25 mg/mL; 30 mg/mL; 35 mg/mL; 40 mg/mL; 45 mg/mL; 50 mg/mL; 55 mg/mL; 60 mg/mL; 65 mg/mL; 70 mg/mL; 75 mg/mL; 80 mg/mL; 85 mg/mL; 90 mg/mL, 95 mg/mL; 100 mg/mL; 150 mg/mL; 200 mg/mL; 250 mg/mL; 300 mg/mL; 350 mg/mL; or 400 mg/mL.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and between 2.5-40%, 2.5-30%, 2.5-20%, 2.5-10%, 5-40%, 5-30%, 5-20%, 5-10%, 6-40%, 6-30%, 6-20%, 6-10%, 10-40%, 10-30%, 10-20%, 20-40%, 20-30%, 25-40%, 25-30%, 3-10%, 4.5-7.5%, 5-7%, 5.5-6.5% of the cyclodextrin, e.g., CAPTISOL®. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL; 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and 2.5%, 3%, 4%, 4.5%, 5%, 5.5%, 6%, 6.5%, 7%, 7.5%, 8%, 8.5%, 9%, 9.5%, 10%, 15%, 20%, 25%, 30%, 35% or 40% of the cyclodextrin, e.g., CAPTISOL®.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and the cyclodextrin, e.g., a β-cyclodextrin, e.g., a sulfo butyl ether β-cyclodextrin, e.g., CAPTISOL®, at a concentration between 25-400 mg/mL; 25-300 mg/mL; 25-200 mg/mL; 25-100 mg/mL; 25-50 mg/mL; 50-400 mg/mL; 50-300 mg/mL; 60-400 mg/mL; 60-300 mg/mL; 150-400 mg/mL; 150-300 mg/mL; 200-300 mg/mL; 200-400 mg/mL; 30-100 mg/mL; 300-400 mg/mL; 30-100 mg/mL; 45-75 mg/mL; 50-70 mg/mL; 55-65 mg/mL; or 50-60 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and the cyclodextrin, e.g., CAPTISOL® at a concentration of 25 mg/mL; 30 mg/mL; 35 mg/mL; 40 mg/mL; 45 mg/mL; 50 mg/mL; 55 mg/mL; 60 mg/mL; 65 mg/mL; 70 mg/mL; 75 mg/mL; 80 mg/mL; 85 mg/mL; 90 mg/mL, 95 mg/mL; 100 mg/mL; 150 mg/mL; 200 mg/mL; 250 mg/mL; 300 mg/mL; 350 mg/mL; or 400 mg/mL.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and between 2.5-40%, 2.5-30%, 2.5-20%, 2.5-10%, 5-40%, 5-30%, 5-20%, 5-10%, 6-40%, 6-30%, 6-20%, 6-10%, 10-40%, 10-30%, 10-20%, 20-40%, 20-30%, 25-40%, 25-30%, 3-10%, 4.5-7.5%, 5-7%, 5.5-6.5% of the cyclodextrin, e.g., CAPTISOL®. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and 2.5%, 3%, 4%, 4.5%, 5%, 5.5%, 6%, 6.5%, 7%, 7.5%, 8%, 8.5%, 9%, 9.5%, 10%, 15%, 20%, 25%, 30%, 35% or 40% of the cyclodextrin, e.g., CAPTISOL®.

In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 1.5 mg/mL, and the cyclodextrin, e.g., a β-cyclodextrin, e.g., a sulfo butyl ether β-cyclodextrin, e.g., CAPTISOL®, at a concentration of 6%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 10 mg/mL, and the cyclodextrin, e.g., a β-cyclodextrin, e.g., a sulfo butyl ether β-cyclodextrin, e.g., CAPTISOL®, at a concentration of 6%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 15 mg/mL, and the cyclodextrin, e.g., a β-cyclodextrin, e.g., a sulfo butyl ether β-cyclodextrin, e.g., CAPTISOL®, at a concentration of 6%.

In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 1.5 mg/mL, and the cyclodextrin, e.g., a β-cyclodextrin, e.g., a sulfo butyl ether β-cyclodextrin, e.g., CAPTISOL®, at a concentration of 15%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 10 mg/mL, and the cyclodextrin, e.g., a β-cyclodextrin, e.g., a sulfo butyl ether β-cyclodextrin, e.g., CAPTISOL®, at a concentration of 15%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 15 mg/mL, and the cyclodextrin, e.g., a β-cyclodextrin, e.g., a sulfo butyl ether β-cyclodextrin, e.g., CAPTISOL®, at a concentration of 15%.

In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 1.5 mg/mL, and the cyclodextrin, e.g., a β-cyclodextrin, e.g., a sulfo butyl ether β-cyclodextrin, e.g., CAP- TISOL®, at a concentration of 30%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 10 mg/mL, and the cyclodextrin, e.g., a β-cyclodextrin, e.g., a sulfo butyl ether β-cyclodextrin, e.g., CAPTISOL®, at a concentration of 30%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 15 mg/mL, and the cyclodextrin, e.g., a β-cyclodextrin, e.g., a sulfo butyl ether β-cyclodextrin, e.g., CAPTISOL®, at a concentration of 30%.

In some embodiments, the allopregnanolone and CAPTISOL® complex is formulated as an aqueous composition with a pH between 3-10, 4-9, 4-8, 4-7, 4-6, 4-5, 5-9, 5-8, 5-7, 5-6, 4.5-7.5, or 5.5-7.5. In some embodiments, the allopregnanolone and CAPTISOL® complex is formulated as an aqueous composition with a pH about 3, 3.5, 4, 4.5, 5, 5.5, 6, 6.5, 7, 7.5, 8, 8.5, or 9. In an embodiment, the allopregnanolone and CAPTISOL® complex is formulated as an aqueous composition with a pH about 6.

In one aspect, the disclosure features a method of treating a subject having a CNS disorder, e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; periodic lateralized epileptiform discharges; a seizure, e.g., acute repetitive seizures, cluster seizures, the method comprising administering to the subject a neuroactive steroid.

In some embodiments, the neuroactive steroid is a progestin derivative, e.g., allopregnanolone. In an embodiment, the neuroactive steroid is allopregnanolone.

In some embodiments, the CNS disorder is a traumatic brain injury. In some embodiments, the CNS disorder is status epilepticus, convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; periodic lateralized epileptiform discharges. In some embodiments, the CNS disorder is a traumatic brain injury. In some embodiments, the CNS disorder is a seizure, e.g., acute repetitive seizures, cluster seizures.

In an embodiment, the disclosure features a method of treating a subject having status epilepticus, e.g., refractory convulsive status epilepticus, non-convulsive status epilepticus, the method comprising administering to the subject allopregnanolone. In an embodiment, the disclosure features a method of treating a subject having a traumatic brain injury the method comprising administering to the subject allopregnanolone.

In one aspect, the disclosure features a method of treating a subject having a CNS disorder, e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; periodic lateralized epileptiform discharges; a seizure, e.g., acute repetitive seizures, cluster seizures, the method comprising administering to the subject a neuroactive steroid, e.g., allopregnanolone, and cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, complex.

In some embodiments, the neuroactive steroid is a progestin derivative, e.g., allopregnanolone. In an embodiment, the neuroactive steroid is allopregnanolone.

In some embodiments, the cyclodextrin is a β-cyclodextrin. In an embodiment, the cyclodextrin is a sulfo butyl ether β-cyclodextrin. In an embodiment, the cyclodextrin is CAPTISOL®.

In some embodiments, the neuroactive steroid is a progestin derivative, e.g., allopregnanolone, and the cyclodextrin is a β-cyclodextrin. In an embodiment, the neuroactive steroid is allopregnanolone and the cyclodextrin is CAPTISOL®.

In some embodiments, the CNS disorder is a traumatic brain injury. In some embodiments, the CNS disorder is status epilepticus, convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; periodic lateralized epileptiform discharges. In some embodiments, the CNS disorder is a traumatic brain injury. In some embodiments, the CNS disorder is a seizure, e.g., acute repetitive seizures, cluster seizures.

In an embodiment, the disclosure features a method of treating a subject having a traumatic brain injury, the method comprising administering to the subject an allopregnanolone and CAPTISOL® complex. In an embodiment, the disclosure features a method of treating a subject having status epilepticus, convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus, the method comprising administering to the subject an allopregnanolone and CAPTISOL® complex. In an embodiment, the disclosure features a method of treating a subject having a seizure, e.g., acute repetitive seizures, cluster seizures, the method comprising administering to the subject an allopregnanolone and CAPTISOL® complex.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated for parenteral administration. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 1.5 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 5 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 15 mg/mL.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration between 25-400 mg/mL; 25-300 mg/mL; 25-200 mg/mL; 25-100 mg/mL; 25-50 mg/mL; 50-400 mg/mL; 50-300 mg/mL; 60-400 mg/mL; 60-300 mg/mL; 150-400 mg/mL; 150-300 mg/mL; 200-300 mg/mL; 200-400 mg/mL; 30-100 mg/mL; 300-400 mg/mL; 30-100 mg/mL; 45-75 mg/mL; 50-70 mg/mL; 55-65 mg/mL; or 50-60 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration of 25 mg/mL; 30 mg/mL; 35 mg/mL; 40 mg/mL; 45 mg/mL; 50 mg/mL; 55 mg/mL; 60 mg/mL; 65 mg/mL; 70 mg/mL; 75 mg/mL; 80 mg/mL; 85 mg/mL; 90 mg/mL, 95 mg/mL; 100 mg/mL; 150 mg/mL; 200 mg/mL; 250 mg/mL; 300 mg/mL; 350 mg/mL; or 400 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration of 60 mg/ml. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising between 2.5-40%, 2.5-30%, 2.5-20%, 2.5-10%, 5-40%, 5-30%, 5-20%, 5-10%, 6-40%, 6-30%, 6-20%, 6-10%, 10-40%, 10-30%, 10-20%, 20-40%, 20-30%, 25-40%, 25-30%, 3-10%, 4.5-7.5%, 5-7%, 5.5-6.5% of the cyclodextrin, e.g., CAPTISOL®. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 2.5%, 3%, 4%, 4.5%, 5%, 5.5%, 6%, 6.5%, 7%, 7.5%, 8%, 8.5%, 9%, 9.5%, 10%, 15%, 20%, 25%, 30%, 35% or 40% of the cyclodextrin, e.g., CAPTISOL®. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 6% of the cyclodextrin. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 15% of the cyclodextrin. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 30% of the cyclodextrin.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and the cyclodextrin, e.g., a β-cyclodextrin, e.g., a sulfo butyl ether β-cyclodextrin, e.g., CAPTISOL®, at a concentration between 25-400 mg/mL; 25-300 mg/mL; 25-200 mg/mL; 25-100 mg/mL; 25-50 mg/mL; 50-400 mg/mL; 50-300 mg/mL; 60-400 mg/mL; 60-300 mg/mL; 150-400 mg/mL; 150-300 mg/mL; 200-300 mg/mL; 200-400 mg/mL; 30-100 mg/mL; 300-400 mg/mL; 30-100 mg/mL; 45-75 mg/mL; 50-70 mg/mL; 55-65 mg/mL; or 50-60 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and the cyclodextrin, e.g., a β-cyclodextrin, e.g., a sulfo butyl ether β-cyclodextrin, e.g., CAPTISOL®, at a concentration of 25 mg/mL; 30 mg/mL; 35 mg/mL; 40 mg/mL; 45 mg/mL; 50 mg/mL; 55 mg/mL; 60 mg/mL; 65 mg/mL; 70 mg/mL; 75 mg/mL; 80 mg/mL; 85 mg/mL; 90 mg/mL, 95 mg/mL; 100 mg/mL; 150 mg/mL; 200 mg/mL; 250 mg/mL; 300 mg/mL; 350 mg/mL; or 400 mg/mL.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and between 2.5-40%, 2.5-30%, 2.5-20%, 2.5-10%, 5-40%, 5-30%, 5-20%, 5-10%, 6-40%, 6-30%, 6-20%, 6-10%, 10-40%, 10-30%, 10-20%, 20-40%, 20-30%, 25-40%, 25-30%, 3-10%, 4.5-7.5%, 5-7%, 5.5-6.5% of the cyclodextrin, e.g., CAPTISOL®. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and 2.5%, 3%, 4%, 4.5%, 5%, 5.5%, 6%, 6.5%, 7%, 7.5%, 8%, 8.5%, 9%, 9.5%, 10%, 15%, 20%, 25%, 30%, 35% or 40% of the cyclodextrin, e.g., CAPTISOL®.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and the cyclodextrin, e.g., a β-cyclodextrin, e.g., a sulfo butyl ether β-cyclodextrin, e.g., CAPTISOL®, at a concentration between 25-400 mg/mL; 25-300 mg/mL; 25-200 mg/mL; 25-100 mg/mL; 25-50 mg/mL; 50-400 mg/mL; 50-300 mg/mL; 60-400 mg/mL; 60-300 mg/mL; 150-400 mg/mL; 150-300 mg/mL; 200-300 mg/mL; 200-400 mg/mL; 30-100 mg/mL; 300-400 mg/mL; 30-100 mg/mL; 45-75 mg/mL; 50-70 mg/mL; 55-65 mg/mL; or 50-60 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and the cyclodextrin, e.g., CAPTISOL® at a concentration of 25 mg/mL; 30 mg/mL; 35 mg/mL; 40 mg/mL; 45 mg/mL; 50 mg/mL; 55 mg/mL; 60 mg/mL; 65 mg/mL; 70 mg/mL; 75 mg/mL; 80 mg/mL; 85 mg/mL; 90 mg/mL, 95 mg/mL; 100 mg/mL; 150 mg/mL; 200 mg/mL; 250 mg/mL; 300 mg/mL; 350 mg/mL; or 400 mg/mL.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and between 2.5-40%, 2.5-30%, 2.5-20%, 2.5-10%, 5-40%, 5-30%, 5-20%, 5-10%, 6-40%, 6-30%, 6-20%, 6-10%, 10-40%, 10-30%, 10-20%, 20-40%, 20-30%, 25-40%, 25-30%, 3-10%, 4.5-7.5%, 5-7%, 5.5-6.5% of the cyclodextrin, e.g., CAPTISOL®. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and 2.5%, 3%, 4%, 4.5%, 5%, 5.5%, 6%, 6.5%, 7%, 7.5%, 8%, 8.5%, 9%, 9.5%, 10%, 15%, 20%, 25%, 30%, 35% or 40% of the cyclodextrin, e.g., CAPTISOL®.

In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 1.5 mg/mL, and the cyclodextrin, e.g., a β-cyclodextrin, e.g., a sulfo butyl ether β-cyclodextrin, e.g., CAPTISOL®, at a concentration of 6%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 10 mg/mL, and the cyclodextrin, e.g., a β-cyclodextrin, e.g., a sulfo butyl ether β-cyclodextrin, e.g., CAPTISOL®, at a concentration of 6%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 15 mg/mL, and the cyclodextrin, e.g., a β-cyclodextrin, e.g., a sulfo butyl ether β-cyclodextrin, e.g., CAPTISOL®, at a concentration of 6%.

In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 1.5 mg/mL, and the cyclodextrin, e.g., a β-cyclodextrin, e.g., a sulfo butyl ether β-cyclodextrin, e.g., CAPTISOL®, at a concentration of 15%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 10 mg/mL, and the cyclodextrin, e.g., a β-cyclodextrin, e.g., a sulfo butyl ether β-cyclodextrin, e.g., CAPTISOL®, at a concentration of 15%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 15 mg/mL, and the cyclodextrin, e.g., a β-cyclodextrin, e.g., a sulfo butyl ether β-cyclodextrin, e.g., CAPTISOL®, at a concentration of 15%.

In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 1.5 mg/mL, and the cyclodextrin, e.g., a β-cyclodextrin, e.g., a sulfo butyl ether β-cyclodextrin, e.g., CAPTISOL®, at a concentration of 30%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 10 mg/mL, and the cyclodextrin, e.g., a β-cyclodextrin, e.g., a sulfo butyl ether β-cyclodextrin, e.g., CAPTISOL®, at a concentration of 30%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 15 mg/mL, and the cyclodextrin, e.g., a β-cyclodextrin, e.g., a sulfo butyl ether β-cyclodextrin, e.g., CAPTISOL®, at a concentration of 30%.

In some embodiments, the allopregnanolone and CAPTISOL® complex is formulated as an aqueous composition with a pH between 3-10, 4-9, 4-8, 4-7, 4-6, 4-5, 5-9, 5-8, 5-7, 5-6, 4.5-7.5, or 5.5-7.5. In some embodiments, the allopregnanolone and CAPTISOL® complex is formulated as an aqueous composition with a pH about 3, 3.5, 4, 4.5, 5, 5.5, 6, 6.5, 7, 7.5, 8, 8.5, or 9. In an embodiment, the allopregnanolone and CAPTISOL® complex is formulated as an aqueous composition with a pH about 6.

In some embodiments, the allopregnanolone and CAPTISOL® complex is formulated as an aqueous composition and is administered intravenously. In some embodiments, the allopregnanolone and CAPTISOL® complex is formulated as an aqueous composition and is administered intramuscularly.

In some embodiments, the allopregnanolone and CAPTISOL® complex is formulated as an aqueous composition and is administered for 1, 2, 3, 4, 5, 6, 7, 8, 9, or 10 consecutive days. In some embodiments, the allopregnanolone and CAPTISOL® complex is formulated as an aqueous composition and is administered between 1-10, 1-5, 5-10, 1-6, 2-6, 3-6, 4-5, or 1-9 consecutive days. In an embodiment, the allopregnanolone and CAPTISOL® complex is formulated as an aqueous composition and is administered for 5 consecutive days. In some embodiments, the duration of administration is 1, 2, 3, 4, 5, 6, 7, 8, 9, or 10 days. In some embodiments, the duration of administration is 3-7, 4-6, 4-5, or 5-6 days. In some embodiments, the duration of administration is 5 days.

In some embodiments, the allopregnanolone and CAPTISOL® complex is formulated as an aqueous composition and is administered at the same dose for 1, 2, 3, 4, 5, 6, 7, 8, 9, or 10 consecutive days. In some embodiments, the allopregnanolone and CAPTISOL® complex is formulated as an aqueous composition and is administered at a load, e.g., bolus, dose for 1, 2, 3, 4, 5, 6, 7, 8, 9, or 10 consecutive days and then administered at a maintenance, e.g., infusion, dose for 1, 2, 3, 4, 5, 6, 7, 8, 9, or 10 consecutive days. In an embodiment, the allopregnanolone and CAPTISOL® complex is formulated as an aqueous composition and is administered at a load, e.g., bolus, dose of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL neuroactive steroid, e.g., allopregnanolone, for 1 day and then administered at a maintenance, e.g., infusion, dose for 3 consecutive days of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL neuroactive steroid, e.g., allopregnanolone. In some embodiments, a maintenance, e.g., infusion, dose described herein, is lower than a load, e.g., bolus, dose described herein. In some embodiments, the maintenance, e.g., infusion, dose is less than 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL.

In some embodiments, the allopregnanolone and CAPTISOL® complex is formulated as an aqueous composition and is administered at a load, e.g., bolus, dose for 1, 2, 3, 4, 5, 6, 7, 8, 9, or 10 consecutive days and then administered at a maintenance, e.g., infusion, dose for 1, 2, 3, 4, 5, 6, 7, 8, 9, or 10 consecutive days and then administered at a taper dose for 1, 2, 3, 4, 5, 6, 7, 8, 9, or 10 consecutive days. In some embodiments, the allopregnanolone and CAPTISOL® complex is formulated as an aqueous composition and is administered at a load, e.g., bolus, dose for 1, 2, 3, 4, 5, 6, 7, 8, 9, or 10 consecutive days and then administered at a maintenance, e.g., infusion, dose for 1, 2, 3, 4, 5, 6, 7, 8, 9, or 10 consecutive days and then administered at a first taper dose for 1, 2, 3, 4, 5, 6, 7, 8, 9, or 10 hours.

In some embodiments, the allopregnanolone and CAPTISOL® complex is formulated as an aqueous composition and is administered at a load, e.g., bolus, dose for 1, 2, 3, 4, 5, 6, 7, 8, 9, or 10 consecutive days and then administered at a maintenance, e.g., infusion, dose for 1, 2, 3, 4, 5, 6, 7, 8, 9, or 10 consecutive days and then administered at a first taper dose for 1, 2, 3, 4, 5, 6, 7, 8, 9, or 10 hours and then administered at a second taper dose for 1, 2, 3, 4, 5, 6, 7, 8, 9, or 10 hours. In some embodiments, the allopregnanolone and CAPTISOL® complex is formulated as an aqueous composition and is administered at a load, e.g., bolus, dose for 1, 2, 3, 4, 5, 6, 7, 8, 9, or 10 consecutive days and then administered at a maintenance, e.g., infusion, dose for 1, 2, 3, 4, 5, 6, 7, 8, 9, or 10 consecutive days and then administered at a first taper dose for 1, 2, 3, 4, 5, 6, 7, 8, 9, or 10 hours and then administered at a second taper dose for 1, 2, 3, 4, 5, 6, 7, 8, 9, or 10 hours and then administered at a third taper dose for 1, 2, 3, 4, 5, 6, 7, 8, 9, or 10 hours.

In some embodiments the first, second, or third taper dose is less than the maintenance, e.g., infusion, dose. In some embodiments, the second taper or third taper dose is less than the first taper dose. In some embodiments, the third taper dose is less than the second taper dose. In some embodiments, the first taper dose is 95%, 90%, 85%, 80%, 75%, 70%, 65%, 60%, 55%, 50%, 45%, 40%, 35%, 30%, 25%, 20%, 15%, 10%, or 5% of the maintenance, e.g., infusion, dose. In some embodiments, the first taper dose is between 95-50%, 75-50%, 85-50%, 90-50%, 80-50%, or 75-100% of the maintenance, e.g., infusion, dose. In an embodiment, the first taper dose is 75% of the maintenance, e.g., infusion, dose.

In some embodiments, the second taper dose is 95%, 90%, 85%, 80%, 75%, 70%, 65%, 60%, 55%, 50%, 45%, 40%, 35%, 30%, 25%, 20%, 15%, 10%, or 5% of the maintenance, e.g., infusion, dose. In some embodiments, the second taper dose is between 95-30%, 75-30%, 85-30%, 60-30%, 70-30%, 50-30%, or 50-40% of the maintenance, e.g., infusion, dose. In an embodiment, the second taper dose is 50% of the maintenance, e.g., infusion, dose.

In some embodiments, the third taper dose is 95%, 90%, 85%, 80%, 75%, 70%, 65%, 60%, 55%, 50%, 45%, 40%, 35%, 30%, 25%, 20%, 15%, 10%, or 5% of the maintenance, e.g., infusion, dose. In some embodiments, the third taper dose is between 50-5%, 40-5%, 30-5%, 25-5%, 25-10%, 25-20%, or 25-40% of the maintenance, e.g., infusion, dose. In an embodiment, the second taper dose is 50% of the maintenance, e.g., infusion, dose. In an embodiment, the third taper dose is 25% of the maintenance, e.g., infusion, dose.

In some embodiments, the allopregnanolone and CAPTISOL® complex is formulated as an aqueous composition and is administered at a dose necessary to achieve a predetermined burst suppression pattern, e.g., inter-burst intervals of between 2-30 seconds; as measured by a method of neurophysiological monitoring, e.g., EEG, CFM. In some embodiments, the allopregnanolone and CAPTISOL® complex is formulated as an aqueous composition and is administered at a dose necessary to achieve a predetermined burst suppression pattern, e.g., inter-burst intervals of between 2-30 seconds, 5-30 seconds, 10-30 seconds, 15-30 seconds, 1-30 seconds, 0-30 seconds, 2-20 seconds, 2-10 seconds, 5-20 seconds, 10-20 seconds, 15-25 seconds, 5-15 seconds or 5-10 seconds; as measured by a method of neurophysiological monitoring, e.g., EEG, CFM.

In some embodiments, the allopregnanolone and CAPTISOL® complex is formulated as an aqueous composition and is administered within 48 hours, 24 hours, 20 hours, 18 hours, 16 hours, 10 hours, 8 hours, 5 hours, 3 hours, 1 hour, or 0.5 hour after a traumatic brain injury. In an embodiment, the allopregnanolone and CAPTISOL® complex is formulated as an aqueous composition and is administered within 10 hours after a traumatic brain injury. In an embodiment, the allopregnanolone and CAPTISOL® complex is formulated as an aqueous composition and is administered within 8 hours after a traumatic brain injury.

In some embodiments, the allopregnanolone and CAPTISOL® complex is formulated as an aqueous composition and is administered within 10 hours, 8 hours, 5 hours, 3 hours, 1 hour, or 0.5 hour after a seizure, e.g., a status epileptic seizure, e.g., a refractory status epileptic seizure has started. In some embodiments, the allopregnanolone and CAPTISOL® complex is formulated as an aqueous composition and is administered within 60 minutes, 45 minutes, 30 minutes, 15 minutes, 10 minutes, or 5 minutes after a seizure, e.g., a status epileptic seizure, e.g., a refractory status epileptic seizure has started. In some embodiments, the allopregnanolone and CAPTISOL® complex is formulated as an aqueous composition and is administered after a seizure, e.g., a status epileptic seizure, e.g., a refractory status epileptic seizure has lasted 5 minutes, 10 minutes, 15 minutes, 20 minutes, 30 minutes or 60 minutes.

In some embodiments, the allopregnanolone and CAPTISOL® complex is formulated as an aqueous composition and is administered prior to the onset of a seizure, e.g., a status epileptic seizure, e.g., a refractory status epileptic seizure.

In one aspect, the disclosure features a method of treating a subject having a CNS disorder, e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; periodic lateralized epileptiform discharges; a seizure, e.g., acute repetitive seizures, cluster seizures, the method comprising administering to the subject a neuroactive steroid, e.g., allopregnanolone, and cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, complex wherein the composition comprises less than 100 ppm of a phosphate, and the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, has an absorption of less than 0.2 A.U. due to a drug-degrading agent, as determined by UV/vis spectrophotometry at a wavelength of 245 nm to 270 nm for an aqueous solution comprising 300 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, has an absorption of less than 0.2 A.U. due to a color forming agent, as determined by UV/vis spectrophotometry at a wavelength of 320 nm to 350 nm for an aqueous solution comprising 500 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, further comprises: less than 20 ppm of a sulfoalkylating agent; less than 0.5% wt. of an underivatized cyclodextrin; less than 1% wt. of an alkali metal halide salt; and less than 0.25% wt. of a hydrolyzed sulfoalkylating agent.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, has an absorption of less than 0.2 A.U. due to a drug-degrading agent, as determined by UV/vis spectrophotometry at a wavelength of 245 nm to 270 nm for an aqueous solution comprising 500 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, comprises: less than 50 ppm of a phosphate; less than 10 ppm of a sulfoalkylating agent; less than 0.2% wt. of an underivatized cyclodextrin; less than 0.5% wt. of an alkali metal halide salt; and less than 0.1% wt. of a hydrolyzed sulfoalkylating agent; and wherein the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, has an absorption of less than 0.2 A.U. due to the color-forming agent, as determined by U/vis spectrophotometry at a wavelength of 320 nm to 350 nm for an aqueous solution comprising 500 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, comprises: less than 10 ppm of a phosphate; less than 2 ppm of a sulfoalkylating agent; less than 0.1% wt. of an underivatized cyclodextrin; less than 0.2% wt. of an alkali metal halide salt; and less than 0.08% wt. of a hydrolyzed sulfoalkylating agent; and wherein the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, has an absorption of less than 0.1 A.U. due to the color-forming agent, as determined by UV/vis spectrophotometry at a wavelength of 320 nm to 350 nm for an aqueous solution comprising 500 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, comprises: less than 5 ppm of a phosphate; less than 0.1% wt. of an alkali metal halide salt; and less than 0.05% wt. of a hydrolyzed sulfoalkylating agent.

In some embodiments, the CNS disorder is a traumatic brain injury. In some embodiments, the CNS disorder is status epilepticus, convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; periodic lateralized epileptiform discharges. In some embodiments, the CNS disorder is a traumatic brain injury. In some embodiments, the CNS disorder is a seizure, e.g., acute repetitive seizures, cluster seizures.

In an embodiment, the disclosure features a method of treating a subject having a traumatic brain injury, the method comprising administering to the subject an allopregnanolone and CAPTISOL® complex. In an embodiment, the disclosure features a method of treating a subject having status epilepticus, convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; periodic lateralized epileptiform discharges, the method comprising administering to the subject an allopregnanolone and CAPTISOL® complex. In an embodiment, the disclosure features a method of treating a subject having a seizure, e.g., acute repetitive seizures, cluster seizures, the method comprising administering to the subject an allopregnanolone and CAPTISOL® complex.

In some embodiments, the neuroactive steroid is a progestin derivative, e.g., allopregnanolone. In an embodiment, the neuroactive steroid is allopregnanolone.

In some embodiments, the cyclodextrin is a β-cyclodextrin. In an embodiment, the cyclodextrin is a sulfo butyl ether β-cyclodextrin. In an embodiment, the cyclodextrin is CAPTISOL®. In an embodiment, the cyclodextrin is a β-cyclodextrin disclosed in U.S. Pat. Nos. 5,874,418; 6,046,177; and 7,635,733, which are herein incorporated by reference.

In some embodiments, the neuroactive steroid is a progestin derivative, e.g., allopregnanolone, and the cyclodextrin is a β-cyclodextrin. In an embodiment, the neuroactive steroid is allopregnanolone and the cyclodextrin is CAPTISOL®.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated for parenteral administration. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 1.5 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 5 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 15 mg/mL.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration between 25-400 mg/mL; 25-300 mg/mL; 25-200 mg/mL; 25-100 mg/mL; 25-50 mg/mL; 50-400 mg/mL; 50-300 mg/mL; 60-400 mg/mL; 60-300 mg/mL; 150-400 mg/mL; 150-300 mg/mL; 200-300 mg/mL; 200-400 mg/mL; 30-100 mg/mL; 300-400 mg/mL; 30-100 mg/mL; 45-75 mg/mL; 50-70 mg/mL; 55-65 mg/mL; or 50-60 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration of 25 mg/mL; 30 mg/mL; 35 mg/mL; 40 mg/mL; 45 mg/mL; 50 mg/mL; 55 mg/mL; 60 mg/mL; 65 mg/mL; 70 mg/mL; 75 mg/mL; 80 mg/mL; 85 mg/mL; 90 mg/mL, 95 mg/mL; 100 mg/mL; 150 mg/mL; 200 mg/mL; 250 mg/mL; 300 mg/mL; 350 mg/mL; or 400 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration of 60 mg/ml. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising between 2.5-40%, 2.5-30%, 2.5-20%, 2.5-10%, 5-40%, 5-30%, 5-20%, 5-10%, 6-40%, 6-30%, 6-20%, 6-10%, 10-40%, 10-30%, 10-20%, 20-40%, 20-30%, 25-40%, 25-30%, 3-10%, 4.5-7.5%, 5-7%, 5.5-6.5% of the cyclodextrin, e.g., CAPTISOL®. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 2.5%, 3%, 4%, 4.5%, 5%, 5.5%, 6%, 6.5%, 7%, 7.5%, 8%, 8.5%, 9%, 9.5%, 10%, 15%, 20%, 25%, 30%, 35% or 40% of the cyclodextrin, e.g., CAPTISOL®. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 6% of the cyclodextrin. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 15% of the cyclodextrin. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 30% of the cyclodextrin.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and the cyclodextrin, e.g., a β-cyclodextrin, e.g., a sulfo butyl ether β-cyclodextrin, e.g., CAPTISOL®, at a concentration between 25-400 mg/mL; 25-300 mg/mL; 25-200 mg/mL; 25-100 mg/mL; 25-50 mg/mL; 50-400 mg/mL; 50-300 mg/mL; 60-400 mg/mL; 60-300 mg/mL; 150-400 mg/mL; 150-300 mg/mL; 200-300 mg/mL; 200-400 mg/mL; 30-100 mg/mL; 300-400 mg/mL; 30-100 mg/mL; 45-75 mg/mL; 50-70 mg/mL; 55-65 mg/mL; or 50-60 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and the cyclodextrin, e.g., a β-cyclodextrin, e.g., a sulfo butyl ether β-cyclodextrin, e.g., CAPTISOL®, at a concentration of 25 mg/mL; 30 mg/mL; 35 mg/mL; 40 mg/mL; 45 mg/mL; 50 mg/mL; 55 mg/mL; 60 mg/mL; 65 mg/mL; 70 mg/mL; 75 mg/mL; 80 mg/mL; 85 mg/mL; 90 mg/mL, 95 mg/mL; 100 mg/mL; 150 mg/mL; 200 mg/mL; 250 mg/mL; 300 mg/mL; 350 mg/mL; or 400 mg/mL.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and between 2.5-40%, 2.5-30%, 2.5-20%, 2.5-10%, 5-40%, 5-30%, 5-20%, 5-10%, 6-40%, 6-30%, 6-20%, 6-10%, 10-40%, 10-30%, 10-20%, 20-40%, 20-30%, 25-40%, 25-30%, 3-10%, 4.5-7.5%, 5-7%, 5.5-6.5% of the cyclodextrin, e.g., CAPTISOL®. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and 2.5%, 3%, 4%, 4.5%, 5%, 5.5%, 6%, 6.5%, 7%, 7.5%, 8%, 8.5%, 9%, 9.5%, 10%, 15%, 20%, 25%, 30%, 35% or 40% of the cyclodextrin, e.g., CAPTISOL®.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and the cyclodextrin, e.g., a β-cyclodextrin, e.g., a sulfo butyl ether β-cyclodextrin, e.g., CAPTISOL®, at a concentration between 25-400 mg/mL; 25-300 mg/mL; 25-200 mg/mL; 25-100 mg/mL; 25-50 mg/mL; 50-400 mg/mL; 50-300 mg/mL; 60-400 mg/mL; 60-300 mg/mL; 150-400 mg/mL; 150-300 mg/mL; 200-300 mg/mL; 200-400 mg/mL; 30-100 mg/mL; 300-400 mg/mL; 30-100 mg/mL; 45-75 mg/mL; 50-70 mg/mL; 55-65 mg/mL; or 50-60 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and the cyclodextrin, e.g., CAPTISOL® at a concentration of 25 mg/mL; 30 mg/mL; 35 mg/mL; 40 mg/mL; 45 mg/mL; 50 mg/mL; 55 mg/mL; 60 mg/mL; 65 mg/mL; 70 mg/mL; 75 mg/mL; 80 mg/mL; 85 mg/mL; 90 mg/mL, 95 mg/mL; 100 mg/mL; 150 mg/mL; 200 mg/mL; 250 mg/mL; 300 mg/mL; 350 mg/mL; or 400 mg/mL.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and between 2.5-40%, 2.5-30%, 2.5-20%, 2.5-10%, 5-40%, 5-30%, 5-20%, 5-10%, 6-40%, 6-30%, 6-20%, 6-10%, 10-40%, 10-30%, 10-20%, 20-40%, 20-30%, 25-40%, 25-30%, 3-10%, 4.5-7.5%, 5-7%, 5.5-6.5% of the cyclodextrin, e.g., CAPTISOL®. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and 2.5%, 3%, 4%, 4.5%, 5%, 5.5%, 6%, 6.5%, 7%, 7.5%, 8%, 8.5%, 9%, 9.5%, 10%, 15%, 20%, 25%, 30%, 35% or 40% of the cyclodextrin, e.g., CAPTISOL®.

In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 1.5 mg/mL, and the cyclodextrin, e.g., a β-cyclodextrin, e.g., a sulfo butyl ether β-cyclodextrin, e.g., CAPTISOL®, at a concentration of 6%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 10 mg/mL, and the cyclodextrin, e.g., a β-cyclodextrin, e.g., a sulfo butyl ether β-cyclodextrin, e.g., CAPTISOL®, at a concentration of 6%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 15 mg/mL, and the cyclodextrin, e.g., a β-cyclodextrin, e.g., a sulfo butyl ether β-cyclodextrin, e.g., CAPTISOL®, at a concentration of 6%.

In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 1.5 mg/mL, and the cyclodextrin, e.g., a β-cyclodextrin, e.g., a sulfo butyl ether β-cyclodextrin, e.g., CAPTISOL®, at a concentration of 15%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 10 mg/mL, and the cyclodextrin, e.g., a β-cyclodextrin, e.g., a sulfo butyl ether β-cyclodextrin, e.g., CAPTISOL®, at a concentration of 15%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 15 mg/mL, and the cyclodextrin, e.g., a β-cyclodextrin, e.g., a sulfo butyl ether β-cyclodextrin, e.g., CAPTISOL®, at a concentration of 15%.

In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 1.5 mg/mL, and the cyclodextrin, e.g., a β-cyclodextrin, e.g., a sulfo butyl ether β-cyclodextrin, e.g., CAPTISOL®, at a concentration of 30%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 10 mg/mL, and the cyclodextrin, e.g., a β-cyclodextrin, e.g., a sulfo butyl ether β-cyclodextrin, e.g., CAPTISOL®, at a concentration of 30%. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 15 mg/mL, and the cyclodextrin, e.g., a β-cyclodextrin, e.g., a sulfo butyl ether β-cyclodextrin, e.g., CAPTISOL®, at a concentration of 30%.

In some embodiments, the allopregnanolone and CAPTISOL® complex is formulated as an aqueous composition with a pH between 3-10, 4-9, 4-8, 4-7, 4-6, 4-5, 5-9, 5-8, 5-7, 5-6, 4.5-7.5, or 5.5-7.5. In some embodiments, the allopregnanolone and CAPTISOL® complex is formulated as an aqueous composition with a pH about 3, 3.5, 4, 4.5, 5, 5.5, 6, 6.5, 7, 7.5, 8, 8.5, or 9. In an embodiment, the allopregnanolone and CAPTISOL® complex is formulated as an aqueous composition with a pH about 6.

In some embodiments, the allopregnanolone and CAPTISOL® complex is formulated as an aqueous composition and is administered intravenously. In some embodiments, the allopregnanolone and CAPTISOL® complex is formulated as an aqueous composition and is administered intramuscularly.

In some embodiments, the allopregnanolone and CAPTISOL® complex is formulated as an aqueous composition and is administered for 1, 2, 3, 4, 5, 6, 7, 8, 9, or 10 consecutive days. In some embodiments, the allopregnanolone and CAPTISOL® complex is formulated as an aqueous composition and is administered between 1-10, 1-5, 5-10, 1-6, 2-6, 3-6, 4-5, or 1-9 consecutive days. In an embodiment, the allopregnanolone and CAPTISOL® complex is formulated as an aqueous composition and is administered for 5 consecutive days. In some embodiments, the duration of administration is 1, 2, 3, 4, 5, 6, 7, 8, 9, or 10 days. In some embodiments, the duration of administration is 3-7, 4-6, 4-5, or 5-6 days. In some embodiments, the duration of administration is 5 days.

In some embodiments, the allopregnanolone and CAPTISOL® complex is formulated as an aqueous composition and is administered at the same dose for 1, 2, 3, 4, 5, 6, 7, 8, 9, or 10 consecutive days. In some embodiments, the allopregnanolone and CAPTISOL® complex is formulated as an aqueous composition and is administered at a load, e.g., bolus, dose for 1, 2, 3, 4, 5, 6, 7, 8, 9, or 10 consecutive days and then administered at a maintenance, e.g., infusion, dose for 1, 2, 3, 4, 5, 6, 7, 8, 9, or 10 consecutive days. In an embodiment, the allopregnanolone and CAPTISOL® complex is formulated as an aqueous composition and is administered at a load, e.g., bolus, dose of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL neuroactive steroid, e.g., allopregnanolone, for 1 day and then administered at a maintenance, e.g., infusion, dose for 3 consecutive days of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL neuroactive steroid, e.g., allopregnanolone. In some embodiments, a maintenance, e.g., infusion, dose described herein, is lower than a load, e.g., bolus, dose described herein. In some embodiments, the maintenance, e.g., infusion, dose is less than 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL.

In some embodiments, the allopregnanolone and CAPTISOL® complex is formulated as an aqueous composition and is administered at a load, e.g., bolus, dose for 1, 2, 3, 4, 5, 6, 7, 8, 9, or 10 consecutive days and then administered at a maintenance, e.g., infusion, dose for 1, 2, 3, 4, 5, 6, 7, 8, 9, or 10 consecutive days and then administered at a taper dose for 1, 2, 3, 4, 5, 6, 7, 8, 9, or 10 consecutive days. In some embodiments, the allopregnanolone and CAPTISOL® complex is formulated as an aqueous composition and is administered at a load, e.g., bolus, dose for 1, 2, 3, 4, 5, 6, 7, 8, 9, or 10 consecutive days and then administered at a maintenance, e.g., infusion, dose for 1, 2, 3, 4, 5, 6, 7, 8, 9, or 10 consecutive days and then administered at a first taper dose for 1, 2, 3, 4, 5, 6, 7, 8, 9, or 10 hours.

In some embodiments, the allopregnanolone and CAPTISOL® complex is formulated as an aqueous composition and is administered at a load, e.g., bolus, dose for 1, 2, 3, 4, 5, 6, 7, 8, 9, or 10 consecutive days and then administered at a maintenance, e.g., infusion, dose for 1, 2, 3, 4, 5, 6, 7, 8, 9, or 10 consecutive days and then administered at a first taper dose for 1, 2, 3, 4, 5, 6, 7, 8, 9, or 10 hours and then administered at a second taper dose for 1, 2, 3, 4, 5, 6, 7, 8, 9, or 10 hours. In some embodiments, the allopregnanolone and CAPTISOL® complex is formulated as an aqueous composition and is administered at a load, e.g., bolus, dose for 1, 2, 3, 4, 5, 6, 7, 8, 9, or 10 consecutive days and then administered at a maintenance, e.g., infusion, dose for 1, 2, 3, 4, 5, 6, 7, 8, 9, or 10 consecutive days and then administered at a first taper dose for 1, 2, 3, 4, 5, 6, 7, 8, 9, or 10 hours and then administered at a second taper dose for 1, 2, 3, 4, 5, 6, 7, 8, 9, or 10 hours and then administered at a third taper dose for 1, 2, 3, 4, 5, 6, 7, 8, 9, or 10 hours.

In some embodiments the first, second, or third taper dose is less than the maintenance, e.g., infusion, dose. In some embodiments, the second taper or third taper dose is less than the first taper dose. In some embodiments, the third taper dose is less than the second taper dose. In some embodiments, the first taper dose is 95%, 90%, 85%, 80%, 75%, 70%, 65%, 60%, 55%, 50%, 45%, 40%, 35%, 30%, 25%, 20%, 15%, 10%, or 5% of the maintenance, e.g., infusion, dose. In some embodiments, the first taper dose is between 95-50%, 75-50%, 85-50%, 90-50%, 80-50%, or 75-100% of the maintenance, e.g., infusion, dose. In an embodiment, the first taper dose is 75% of the maintenance, e.g., infusion, dose.

In some embodiments, the second taper dose is 95%, 90%, 85%, 80%, 75%, 70%, 65%, 60%, 55%, 50%, 45%, 40%, 35%, 30%, 25%, 20%, 15%, 10%, or 5% of the maintenance, e.g., infusion, dose. In some embodiments, the second taper dose is between 95-30%, 75-30%, 85-30%, 60-30%, 70-30%, 50-30%, or 50-40% of the maintenance, e.g., infusion, dose. In an embodiment, the second taper dose is 50% of the maintenance, e.g., infusion, dose.

In some embodiments, the third taper dose is 95%, 90%, 85%, 80%, 75%, 70%, 65%, 60%, 55%, 50%, 45%, 40%, 35%, 30%, 25%, 20%, 15%, 10%, or 5% of the maintenance, e.g., infusion, dose. In some embodiments, the third taper dose is between 50-5%, 40-5%, 30-5%, 25-5%, 25-10%, 25-20%, or 25-40% of the maintenance, e.g., infusion, dose. In an embodiment, the second taper dose is 50% of the maintenance, e.g., infusion, dose. In an embodiment, the third taper dose is 25% of the maintenance, e.g., infusion, dose.

In some embodiments, the allopregnanolone and CAPTISOL® complex is formulated as an aqueous composition and is administered at a dose necessary to achieve a predetermined burst suppression pattern, e.g., inter-burst intervals of between 2-30 seconds; as measured by a method of neurophysiological monitoring, e.g., EEG, CFM. In some embodiments, the allopregnanolone and CAPTISOL® complex is formulated as an aqueous composition and is administered at a dose necessary to achieve a predetermined burst suppression pattern, e.g., inter-burst intervals of between 2-30 seconds, 5-30 seconds, 10-30 seconds, 15-30 seconds, 1-30 seconds, 0-30 seconds, 2-20 seconds, 2-10 seconds, 5-20 seconds, 10-20 seconds, 15-25 seconds, 5-15 seconds or 5-10 seconds; as measured by a method of neurophysiological monitoring, e.g., EEG, CFM.

In some embodiments, the allopregnanolone and CAPTISOL® complex is formulated as an aqueous composition and is administered within 48 hours, 24 hours, 20 hours, 18 hours, 16 hours, 10 hours, 8 hours, 5 hours, 3 hours, 1 hour, or 0.5 hour after a traumatic brain injury. In an embodiment, the allopregnanolone and CAPTISOL® complex is formulated as an aqueous composition and is administered within 10 hours after a traumatic brain injury. In an embodiment, the allopregnanolone and CAPTISOL® complex is formulated as an aqueous composition and is administered within 8 hours after a traumatic brain injury.

In some embodiments, the allopregnanolone and CAPTISOL® complex is formulated as an aqueous composition and is administered within 10 hours, 8 hours, 5 hours, 3 hours, 1 hour, or 0.5 hour after a seizure, e.g., a status epileptic seizure, e.g., a refractory status epileptic seizure has started. In some embodiments, the allopregnanolone and CAPTISOL® complex is formulated as an aqueous composition and is administered within 60 minutes, 45 minutes, 30 minutes, 15 minutes, 10 minutes, or 5 minutes after a seizure, e.g., a status epileptic seizure, e.g., a refractory status epileptic seizure has started. In some embodiments, the allopregnanolone and CAPTISOL® complex is formulated as an aqueous composition and is administered after a seizure, e.g., a status epileptic seizure, e.g., a refractory status epileptic seizure has lasted 5 minutes, 10 minutes, 15 minutes, 20 minutes, 30 minutes or 60 minutes.

In some embodiments, the allopregnanolone and CAPTISOL® complex is formulated as an aqueous composition and is administered prior to the onset of a seizure, e.g., a status epileptic seizure, e.g., a refractory status epileptic seizure.

DETAILED DESCRIPTION OF THE INVENTION

Figure 1A:
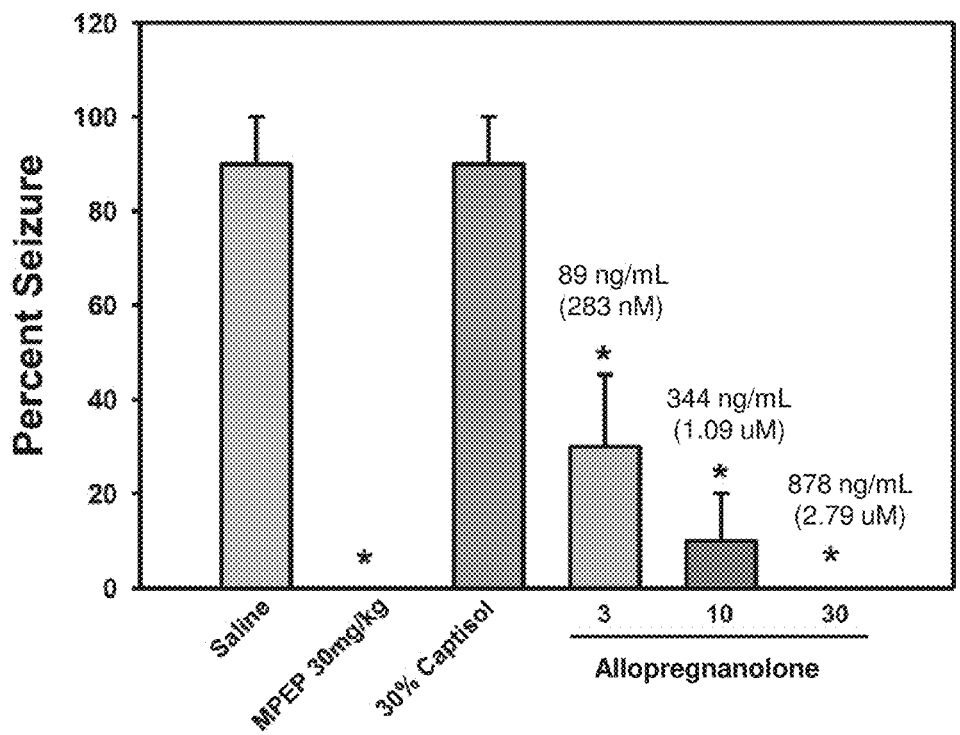
FIG. 1A is a bar graph depicting the percent seizure in fmr1 KO mice intraperitoneally administered 3, 10, 30 mg/kg allopregnanolone in 30% β-Cyclodextrin.

As used herein "allopregnanolone" also encompasses pharmaceutically acceptable, pharmacologically active derivatives including individual enantiomers (dextrogyral and levrogyral enantiomers) and their pharmaceutically acceptable salts, mixtures of enantiomers and their pharmaceutically acceptable salts, and active metabolites and their pharmaceutically acceptable salts, unless otherwise noted. It is understood that in some cases dosages of enantiomers, derivatives, and metabolites may need to be adjusted based on relative activity of the racemic mixture of allopregnanolone.

As used herein, "pharmaceutically acceptable salts" refer to derivatives of the disclosed compounds wherein the parent compound is modified by making the acid-addition or base-addition salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

Delayed release dosage form: A delayed release dosage form is one that releases a drug (or drugs) at a time other than promptly after administration.

Extended release dosage form: An extended release dosage form is one that allows at least a twofold reduction in dosing frequency as compared to the drug presented as a conventional dosage form (e.g. as a solution or prompt drug-releasing, conventional solid dosage form).

Modified release dosage form: A modified release dosage form is one for which the drug release characteristics of time, course and/or location are chosen to accomplish therapeutic or convenience objectives not offered by conventional dosage forms such as solutions, ointments, or promptly dissolving dosage forms. Delayed release and extended release dosage forms and their combinations are types of modified release dosage forms.

Matrix-forming materials: Matrix forming materials are materials which form strong, viscous gels upon hydration and provide control of drug diffusion and release. In hydrophilic matrix systems, matrix forming materials are uniformly incorporated throughout the tablet. Upon contact with water, the outer tablet layer is partially hydrated, forming a gel layer. The rate of diffusion of the drug(s) out of the gel layer and the rate of erosion of the gel layer determine overall tablet dissolution and drug delivery rates. Examples of matrix forming materials include cellulose ethers that are water-soluble such as methylcellulose, ethyl cellulose and hydroxypropyl methylcellulose.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. In certain embodiments, alkyl groups contain between 1 and 6, more preferably between 1 and 4 carbon atoms. Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The alkyl groups may also be substituted with one or more groups including, but not limited to, halogen, hydroxy, amino, thio, ether, ester, carboxy, oxo, and aldehyde groups. The alkyl groups may also contain one or more heteroatoms within the carbon backbone. Preferably the heteroatoms incorporated into the carbon backbone are oxygen, nitrogen, sulfur, and combinations thereof. In certain embodiments, the alkyl group contains between one and four heteroatoms.

"Alkenyl" and "Alkynyl", as used herein, refer to unsaturated aliphatic groups containing or comprising one or more double or triple bonds analogous in length (e.g., $C_2$-$C_{30}$) and possible substitution to the alkyl groups described above.

"Heterocycle" or "heterocyclic", as used herein, refers to a cyclic radical attached via a ring carbon or nitrogen of a monocyclic or bicyclic ring containing or comprising 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_{1-4}$) alkyl, phenyl or benzyl, and optionally containing or comprising one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Halogen", as used herein, refers to fluorine, chlorine, bromine, or iodine.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing or comprising any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

A therapeutically effective treatment is one that results in alleviation of one or more symptoms of the injury, such as improved morphological recovery (i.e., enhanced tissue viability) and/or behavioral recovery. The improvement can be characterized as an increase in either the rate and/or the extent of behavioral and/or anatomical recovery following the traumatic CNS injury. Neurodegeneration is the progressive loss of neurons in the central nervous system. As used herein, "neuroprotection" is the arrest and/or reverse progression of neurodegeneration following a traumatic central nervous system injury. Multiple physiological events lead to the neurodegeneration of the CNS tissues following a traumatic CNS injury. These events include, for example, cerebral edema, destruction of vascular integrity, increase in the immune and inflammatory response, demyelinization, and lipid peroxidation. The formulation may be useful in reducing and/or preventing the physiological events leading to neurodegeneration, including reducing or eliminating neuronal cell death, edema, ischemia, and enhancing tissue viability following a traumatic injury to the central nervous system.

Modified Release Neuroactive Steroid Formulations

A. Neuroactive Steroids

Neuroactive steroids (or neurosteroids) are natural, synthetic, or semi-synthetic steroids that rapidly alter neuronal excitability through interaction with neurotransmitter-gated ion channels. Neuroactive steroids effect binding to membrane-bound receptors such as those for inhibitory and (or) excitatory neurotransmitters including $GABA_A$, NMDA, and sigma receptors.

The steroids that may be classified into functional groups according to chemical structure and physiological activity and include estrogenic hormones, progestational hormones, and androgenic hormones. Of particular interest are progestational hormones, referred to herein as "progestins" or "progestogens", and their derivatives and bioactive metabolites. Members of this broad family include steroid hormones disclosed in Remington's Pharmaceutical Sciences, Gennaro et al., Mack Publishing Co. (18th ed. 1990), 990-993. As with all other classes of steroids, stereoisomerism is of fundamental importance with the sex hormones. As used herein, a variety of progestins (i.e., progesterone) and their derivatives, including both synthetic and natural products, can be used, as well as progestin metabolites such as progesterone.

The term "progesterone" as used herein refers to a member of the progestin family and includes a 21 carbon steroid hormone. Progesterone is also known as D4-pregnene-3,20-dione; Δ4-pregnene-3,20-dione; or pregn-4-ene-3,20-dione. As used herein a "synthetic progestin" is a molecule whose structure is related to that of progesterone, is synthetically derived, and retains the biologically activity of progesterone (i.e., treats a traumatic CNS injury).

Representative synthetic progestins include, but are not limited to, substitutions at the 17-position of the progesterone ring to introduce a hydroxyl, acetyl, hydroxyl acetyl, aliphatic, nitro, or heterocyclic group, modifications to produce 17α-OH esters (i.e., 17 α-hydroxyprogesterone caproate), as well as modifications that introduce 6-methyl, 6-ene, and 6-chloro substituents onto progesterone (i.e., medroxyprogesterone acetate, megestrol acetate, and chlormadinone acetate), and which retains the biologically activity of progesterone (i.e., treats a traumatic CNS injury). Such progestin derivatives include 5-dehydroprogesterone, 6-dehydro-retroprogesterone (dydrogesterone), allopregnanolone (allopregnan-3α, or 3β-ol-20-one), ethynodiol diacetate, hydroxyprogesterone caproate (pregn-4-ene-3,20-dione, 17-(1-oxohexy)oxy); levonorgestrel, norethindrone, norethindrone acetate (19-norpregn-4-en-20-yn-3-one, 17-(acetyloxy)-,(17α)-); norethynodrel, norgestrel, pregnenolone, and megestrol acetate.

Useful progestins also can include allopregnone-3α or 3β, 20α or 20β-diol (see Merck Index 258-261); allopregnane-3β,21-diol-11,20-dione; allopregnane-3β,17α-diol-20-one; 3,20-allopregnanedione, allopregnane, 3β,11β,17α,20β,21-pentol; allopregnane-3β,17α,20β,21-tetrol; allopregnane-3α or 3β,11β,17α,21-tetrol-20-one, allopregnane-3β,17α or 20β-triol; allopregnane-3β,17α,21-triol-11,20-dione; allopregnane-3β,11β,21-triol-20-one; allopregnane-3β,17α,21-triol-20-one; allopregnane-3α or 3β-ol-20-one; pregnane-diol; 3,20-pregnanedione; pregnan-3α-ol-20-one; 4-pregnene-20,21-diol-3,11-dione; 4-pregnene-11β,17α, 20β,21-tetrol-3-one; 4-pregnene-17α,20β,21-triol-3,11-dione; 4-pregnene-17α,20β,21-triol-3-one, and pregnenolone methyl ether. Further progestin derivatives include esters with non-toxic organic acids such as acetic acid, benzoic acid, maleic acid, malic acid, caproic acid, and citric acid and inorganic salts such as hydrochloride, sulfate, nitrate, bicarbonate and carbonate salts. Other suitable progestins include alphaxalone, alphadolone, hydroxydione, and minaxolone.

Additional suitable neuroactive steroids are disclosed in United States Patent Application Publication Nos. US 2011/0092473 and US 2010/0317638, and U.S. Pat. No. 5,232,917, which are incorporated herein by reference for the neuroactive steroids described therein.

In certain embodiments, the neuroactive steroid is defined by Formula I

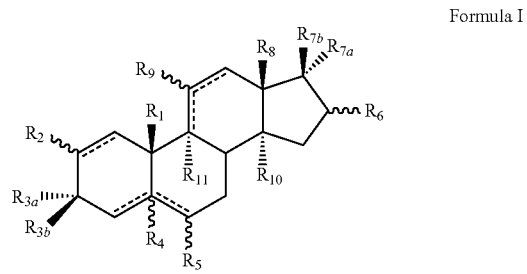

Formula I wherein, $R_1$ is hydrogen or an alkyl group, alkenyl group, or alkynyl group;

$R_2$ is hydrogen, or an amino, thio, sulfinyl, sulfonyl, halogen, trifluoromethyl, nitro, alkoxy, alkyl, alkenyl, or alkynyl group;

$R_{3a}$ is a hydroxyl group and $R_{3b}$ is hydrogen, or $R_{3a}$ and $R_{3b}$ taken together represent a keto group;

$R_4$ is hydrogen when the bonds between C4 and C5 and C5 and C6 are single bonds, or is absent when a double bond is present between C4 and C5 of the steroid ring system or C5 and C6 of the steroid ring system;

$R_5$ is hydrogen, or an alkyl, alkoxy, amino, nitro, hydroxyl, halogen, trifluoromethyl, cyano, alkenyl, or alkynyl group;

$R_6$ is hydrogen, or an alkyl, alkoxy, amino, nitro, hydroxyl, halogen, trifluoromethyl, cyano, alkenyl, or alkynyl group;

$R_{7a}$ is hydrogen, or an acetyl, hydroxyl acetyl, acyl, alkyl, alkoxy, amino, nitro, halogen, trifluoromethyl, cyano, alkenyl, hetercyclic, or alkynyl group;

$R_{7b}$ is hydrogen, or an acetyl, hydroxyl acetyl, acyl, alkyl, alkoxy, amino, nitro, halogen, trifluoromethyl, cyano, alkenyl, hetercyclic, or alkynyl group;

$R_8$ is hydrogen, or an acetyl, hydroxyl acetyl, acyl, alkyl, alkoxy, amino, nitro, halogen, trifluoromethyl, cyano, alkenyl, hetercyclic, or alkynyl group;

or $R_{7b}$ and $R_8$, together with the carbon atoms to which they are attached form a C3-C7 carbocyclic or heterocyclic ring, optionally substituted with one or more substituents selected from is hydrogen, or an acetyl, hydroxyl acetyl, acyl, alkyl, alkoxy, amino, nitro, halogen, trifluoromethyl, cyano, alkenyl, hetercyclic, epoxy, or alkynyl group;

$R_9$ is hydrogen, or an amino, thio, sulfinyl, nitro, sulfonyl, halogen, alkoxy, alkyl, alkenyl, keto, or alkynyl group;

$R_{10}$ is $R_5$ is hydrogen, or an alkyl, alkoxy, amino, nitro, hydroxyl, halogen, trifluoromethyl, cyano, alkenyl, or alkynyl group, preferably hydrogen;

$R_{11}$ is absent or is hydrogen, or an alkyl, alkoxy, amino, nitro, hydroxyl, halogen, trifluoromethyl, cyano, alkenyl, or alkynyl group, preferably hydrogen if $R_{11}$ is present;

and wherein the dotted lines indicate that a single or double bond may be present.

In particular embodiments, the steroids are one or more of a series sedative-hypnotic 3 alpha-hydroxy ring A-reduced pregnane steroids that include the major metabolites of progesterone and deoxycorticosterone, 3 alpha-hydroxy-5 alpha-pregnan-20-one (allopregnanolone) and 3 alpha,21-dihydroxy-5 alpha-pregnan-20-one (allotetrahydroDOC), respectively. These 3 alpha-hydroxysteroids do not interact with classical intracellular steroid receptors but bind stereoselectively and with high affinity to receptors for the major inhibitory neurotransmitter in the brain, gamma-amino-butyric acid (GABA).

In certain embodiments, the neuroactive steroids are progesterone, allopregnanolone or other progesterone analogs. In a particular embodiment, the neuroactive steroid is allopregnanolone or a derivative thereof. Exemplary derivatives include, but are not limited to, (20R)-17beta-(1-hydroxy-2, 3-butadienyl)-5alpha-androstane-3alpha-ol (HBAO). Additional derivatives are described in WO 2012/127176.

The lipophilic nature of allopregnanolone can make it different to formulate for in vivo administration. As discussed above, allopregnanolone can be formulated with a host, such as a cyclodextrin to improve the solubility. Alternatively, or additionally, allopregnanolone can be modified in an attempt to improve the solubility. For example, polar groups can be introduced onto position 16α with the goal of increasing water solubility, brain accessibility, and potency of neuroactive steroids as described in Kasal et al., *J. Med. Chem.*, 52(7), 2119-215 (2009).

As used herein "neuroactive steroid" also encompasses pharmaceutically acceptable, pharmacologically active derivatives of neuroactive steroids including both individual enantiomers of neuroactive steroids (dextrogyral and levrogyral enantiomers) and their pharmaceutically acceptable salts, mixtures of neuroactive steroid enantiomers and their pharmaceutically acceptable salts, and active metabolites of neuroactive steroid and their pharmaceutically acceptable salts, unless otherwise noted. It is understood that in some cases dosages of enantiomers, derivatives, and metabolites may need to be adjusted based on relative activity of the racemic mixture of neuroactive steroid.

As used herein, "pharmaceutically acceptable salts" refer to derivatives of the disclosed compounds wherein the parent compound is modified by making the acid-addition or base-addition salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

Neuroprotective steroids generally contain one or more chiral centers, and thus exist as one or more stereoisomers. Such stereoisomers can be prepared and/or isolated as a single enantiomer, a mixture of diastereomers, or a racemic mixture.

As used herein, the term "stereoisomers" refers to compounds made up of the same atoms having the same bond order but having different three-dimensional arrangements of atoms which are not interchangeable. The three-dimensional structures are called configurations. As used herein, the term "enantiomers" refers to two stereoisomers which are non-superimposable mirror images of one another. As used herein, the term "optical isomer" is equivalent to the term "enantiomer". As used herein the term "diastereomer" refers to two stereoisomers which are not mirror images but also not superimposable. The terms "racemate", "racemic mixture" or "racemic modification" refer to a mixture of equal parts of enantiomers. The term "chiral center" refers to a carbon atom to which four different groups are attached. Choice of the appropriate chiral column, eluent, and conditions necessary to effect separation of the pair of enantiomers is well known to one of ordinary skill in the art using standard techniques (see e.g. Jacques, J. et al., "Enantiomers, Racemates, and Resolutions", John Wiley and Sons, Inc. 1981).

B. Dosage and Pharmacokinetics

The compositions including the therapeutically effective concentration of progesterone, allopregnanolone, or a synthetic progestin may be administered using any acceptable method known in the art. For example, the pharmaceutical composition including progesterone, allopregnanolone, or a synthetic progestin can be administered by any method, including intramuscular (IM) injection, subcutaneous (SC) injection, intrathecal administration, or via the pulmonary, nasal or mucosal routes of administration. The formulation is designed to mimic the intra-CNS levels achieved with progesterone, allopregnanolone, or a synthetic progestin administered by infusion over a period of about 1 to about 120 hours, more preferably over a period of about 24 to about 72 hours, over a period of about 48 to about 96 hours, or over a period of about 24 to about 120 hours.

In one embodiment, progesterone, allopregnanolone, or a synthetic progestin is administered in a dose equivalent to parenteral administration of about 0.1 ng to about 100 g per kg of body weight, about 10 ng to about 50 g per kg of body weight, about 100 ng to about 1 g per kg of body weight, from about 1 μg to about 100 mg per kg of body weight, from about 1 μg to about 50 mg per kg of body weight, from about 1 mg to about 500 mg per kg of body weight; and from about 1 mg to about 50 mg per kg of body weight. Alternatively, the amount of progesterone, allopregnanolone, or a synthetic progestin administered to achieve a therapeutic effective dose is about 0.1 ng, 1 ng, 10 ng, 100 ng, 1 μg, 10 μg, 100 μg, 1 mg, 1.5 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

Although the progesterone, allopregnanolone, or a synthetic progestin may be administered once or several times a day, and the duration of the treatment may be once per day for a period of about 1, 2, 3, 4, 5, 6, 7 days or more, it is more preferably to administer either a single dose in the form of an individual dosage unit or several smaller dosage units or by multiple administration of subdivided dosages at certain intervals. For instance, a dosage unit can be administered from about 0 hours to about 1 hr, about 1 hr to about 24 hr, about 1 to about 72 hours, about 1 to about 120 hours, or about 24 hours to at least about 120 hours post injury. Alternatively, the dosage unit can be administered from about 0.5, 1, 1.5, 2, 3, 4, 5, 6, 7, 8, 9, 10, 11, 12, 13, 14, 15, 16, 17, 18, 19, 20, 21, 22, 23, 24, 30, 40, 48, 72, 96, 120 hours or longer post injury. Subsequent dosage units can be administered any time following the initial administration such that a therapeutic effect is achieved. For instance, additional dosage units can be administered to protect the subject from the secondary wave of edema that may occur over the first several days post-injury. The therapy with the progesterone, allopregnanolone, or a synthetic progestin can instead include a multi-level progesterone, allopregnanolone, or a synthetic progestin dosing regimen wherein the progesterone, allopregnanolone, or a synthetic progestin is administered during two or more time periods, preferably having a combined duration of about 12 hours to about 7 days, including, 1, 2, 3, 4, or 5 days or about 15, 15, 30, 35, 40, 45, 50, 55, 60, 65, 70, 75, 80, 85, 90, 95, 100, 105, 110, 115, 120, 125, 130, 135, 140, or 144 hours or about 1 to 24 hours, about 12 to 36 hours, about 24 to 48 hours, about 36 to 60 hours, about 48 to 72 hours, about 60 to 96 hours, about 72 to 108 hours, about 96 to 120 hours, or about 108 to 136 hours. In one embodiment, the two-level progesterone, allopregnanolone, or a synthetic progestin dosing regimen has a combined duration of about 1 day to about 5 days; in other embodiments, the two-level progesterone, allopregnanolone, or a synthetic progestin dosing regimen has a combined duration of about 1 day to about 3 days.

In one embodiment, the total hourly dose of progesterone, allopregnanolone, or a synthetic progestin that is to be administered during the first and second time periods of the two-level progesterone, allopregnanolone, or a synthetic progestin dosing regimen is chosen such that a higher total dose of progesterone, allopregnanolone, or a synthetic progestin per hour is given during the first time period and a lower dose of progesterone, allopregnanolone, or a synthetic progestin per hour is given during the second time period. The duration of the individual first and second time periods of the two-level progesterone, allopregnanolone, or a synthetic progestin dosing regimen can vary, depending upon the health of the individual and history of the traumatic injury. Generally, the subject is administered higher total dose of progesterone, allopregnanolone, or a synthetic progestin per hour for at least 1, 2, 3, 4, 5, 6, 12 or 24 hours out of the 1 day to 5 day two-level progesterone, allopregnanolone, or a synthetic progestin dosing regimen. The length of the second time period can be adjusted accordingly, and range for example, from about 12 hrs, 24 hrs, 36 hrs, 48 hrs, 60 hrs, 72 hrs, 84 hrs, 96 hrs, 108 hrs, 120 hrs or about 12 to about 36 hrs, about 24 to about 36 hrs, about 24 to about 48 hrs, about 36 hrs to about 60 hours, about 48 hrs to about 72 hrs, about 60 hrs to about 84 hours, about 72 hrs to about 96 hrs, or about 108 hrs to about 120 hrs. Thus, for example, where the two-level progesterone, allopregnanolone, or a synthetic progestin dosing regimen has a combined duration of 3 days, the higher total doses of progesterone, allopregnanolone, or a synthetic progestin could be administered for the first hour, and the lower total hourly dose of progesterone, allopregnanolone, or a synthetic progestin could be administered for hours 2 to 72.

Area under the curve (AUC) refers to the area under the curve that tracks the serum concentration (nmol/L) of progesterone, allopregnanolone, or a synthetic progestin over a give time following the IV administration of the reference progesterone, allopregnanolone, or a synthetic progestin standard. By "reference progesterone, allopregnanolone, or a synthetic progestin standard" is intended the formulation of progesterone, allopregnanolone, or a synthetic progestin that serves as the basis for determination of the total hourly progesterone, allopregnanolone, or a synthetic progestin dose to be administered to a human subject with a traumatic central nervous system injury to achieve the desired positive effect, i.e., a positive therapeutic response that is improved with respect to that observed without administration of progesterone, allopregnanolone, or a synthetic progestin. In an embodiment, the dose of progesterone, allopregnanolone, or a synthetic progestin to be administered provides a final serum level of progesterone, allopregnanolone, or a synthetic progestin of about 100 ng/ml to about 1000 ng/ml, about 1100 ng/ml to about 1450 ng/ml, 100 ng/ml to about 250 ng/ml, about 200 ng/ml to about 350 ng/ml, about 300 ng/ml to about 450 ng/ml, about 350 ng/ml to about 450 ng/ml, about 400 ng/ml to about 550 ng/ml, about 500 ng/ml to about 650 ng/ml, about 600 ng/ml to about 750 ng/ml, about 700 ng/ml to about 850 ng/ml, about 800 ng/ml to about 950 ng/ml, about 900 ng/ml to about 1050 ng/ml, about 1000 ng/ml to about 1150 ng/ml, about 100 ng/ml to about 1250 ng/ml, about 1200 ng/ml to about 1350 ng/ml, about 1300 ng/ml to about 1500 ng/m. In specific embodiments, the serum level of progesterone, allopregnanolone, or a synthetic progestin is about 100 ng/ml, 250 ng/ml, 300 ng/ml, 350 ng/ml, 360 ng/ml, 370 ng/ml, 380 ng/ml, 390 ng/ml, 400 ng/ml, 410 ng/ml, 420 ng/ml, 430 ng/ml, 440 ng/ml, 450 ng/ml, 500 ng/ml, 750 ng/ml, 900 ng/ml, 1200 ng/ml, 1400 ng/ml, or 1600 ng/ml.

In other embodiments, the constant progesterone, allopregnanolone, or a synthetic progestin therapy or the two-level progesterone, allopregnanolone, or a synthetic progestin therapy includes a final time period in which the administration of progesterone, allopregnanolone, or a synthetic progestin is tapered. By "tapered administration" is meant an administration protocol which reduces the dose of administration to the patient and thereby produces a gradual reduction and eventual elimination of progesterone, allopregnanolone, or a synthetic progestin, either over a fixed period of time or a time determined empirically by a physician's assessment based on regular monitoring of a therapeutic response of a subject to a traumatic CNS injury. The period of the tapered progesterone, allopregnanolone, or a synthetic progestin administration can be about 12, 24, 36, 48 hours or longer. Alternatively, the period of the tapered progesterone, allopregnanolone, or a synthetic progestin administration can range from about 1 to 12 hours, about 12 to about 48 hours, or about 24 to about 36 hours.

The drug taper employed could be a "linear" taper. For example, a "10%" linear taper from 500 mg would go 500, 450, 400, 350, 300, 250, 200, 150, 100, 50. Alternatively, an exponential taper could be employed which, if the program outlined above is used as an example, the exponential taper would be, e.g., 500, 450, 405, 365, 329, 296, 266, 239, etc. Accordingly, about a 5%, 10%, 20%,30%, or 40% linear or exponential taper could be employed in the methods of the invention. In addition, a linear or exponential taper of about 1% to 5%, about 6% to 10%, about 11% to 15%, about 16% to 20%, about 21% to 25%, about 26% to 30%, about 31% to 35%, about 36% to 40% could be employed.

Where a subject undergoing therapy exhibits a partial response, or a relapse following completion of the first cycle of the therapy, subsequent courses of progesterone, allopregnanolone, or a synthetic progestin therapy may be needed to achieve a partial or complete therapeutic response. Thus, subsequent to a period of time off from a first treatment period, which may have included a constant progesterone, allopregnanolone, or a synthetic progestin dosing regimen or a two-level progesterone, allopregnanolone, or a synthetic progestin dosing regimen, a subject may receive one or more additional treatment periods including either constant or two-level progesterone, allopregnanolone, or a synthetic progestin dosing regimens. Such a period of time off between treatment periods is referred to herein as a time period of discontinuance. It is recognized that the length of the time period of discontinuance is dependent upon the degree of subject response (i.e., complete versus partial) achieved with any prior treatment periods of the progesterone, allopregnanolone, or a synthetic progestin therapy.

These multiple treatment sessions are referred to herein as maintenance cycles, where each maintenance cycle includes a completed constant or two-level progesterone, allopregnanolone, or a synthetic progestin dosing regimen. By "completed two-level progesterone, allopregnanolone, or a synthetic progestin dosing regimen" is intended the subject has been administered both the first period and the second period of progesterone, allopregnanolone, or a synthetic progestin dosing. The necessity for multiple maintenance cycles can be assessed by monitoring the physiological and behavioral improvement of the patient. The duration between maintenance cycles can be about 1 hr, 15 hr, 1 day, 2 day, 3 day, 4 day, 5 day, 6 day or other such time periods falling within the range of about 1 day to about 14 days.

As used herein, "about" means approximately plus or minus ten percent.

C. Formulations

Formulations of neuroactive steroids contain one or more neuroactive steroids in combination with one or more pharmaceutically acceptable excipients. In some cases, formulations contain just one neuroactive steroid. In other cases, the formulations include a mixture of two or more neuroactive steroids. The neuroactive steroids can be incorporated in the formulations described below as neutral compounds, pharmaceutically acceptable salts, and/or prodrugs or metabolites.

Pharmaceutical formulations can be designed for immediate release, sustained release, delayed release and/or burst release of one or more neuroactive steroids in a therapeutically effective amount. In an embodiment, the formulation provides an initial burst release of a "loading dosage", followed by a sustained release to maintain the therapeutically effective dosage. This can be accomplished using a delayed and/or extended release formulation.

1. Solubilization of Neuroactive Steroids

Many neuroactive steroids possess limited aqueous solubility. In order to provide formulations capable of delivering therapeutically effective dosages, a variety of methods can be employed to enhance the solubility and bioavailability of neuroactive steroids. See, for example, "Water-Insoluble Drug Formulation", 2nd Edition, edited by Rong Liu (CRC Press, Boca Raton, Fla., 2008). Using the techniques described below, a solubilized formulation of one or more neuroactive steroids can be prepared. These solubilized formulations can be further incorporated into the parenteral and non-parenteral formulations described in sections 2 and 3 a. Inclusion Complexes

The solubility of neuroactive steroids can be improved by inclusion complexation (i.e., host-guest formulations). Inclusion complexes are formed when a nonpolar molecule (i.e., the guest, such as a drug with poor aqueous stability) or portion of a molecule inserts into a nonpolar cavity of another molecule or group of molecules (i.e., the host). If the host molecule or molecules exhibit water good solubility, the solubility of the host-guest complex will be greater than the solubility of the guest alone.

Inclusion complexes containing or comprising one or more neuroactive steroids can be formed using any suitable host molecule or molecules. For example, the water solubility of neuroactive steroids can be increased by inclusion complexation with cyclodextrins. Steroid-cyclodextrin complexes are known in the art. See, for example, U.S. Pat. No. 7,569,557 to Backensfeld, et al., and U.S. Patent Application Publication No. US 2006/0058262 to Zoppetti, et al.

Dextrans are soluble polysaccharides produced by bacteria and yeasts. They are characterized by a predominance (>95%) of α (1-6) backbone linkages and varying proportions of α(1-2), α(1-3) and α(1-4) linkages typically at branch points 1, 2. Dextrins are partially hydrolyzed glucose homopolymers composed exclusively of α(1-4) backbone linkages.

Cyclodextrins are cyclic oligosaccharides containing or comprising six (α-cyclodextrin), seven (β-cyclodextrin), eight (γ-cyclodextrin), or more α-(1,4)-linked glucose residues. The hydroxyl groups of the cyclodextrins are oriented to the outside of the ring while the glucosidic oxygen and two rings of the non-exchangeable hydrogen atoms are directed towards the interior of the cavity. As a result, cyclodextrins possess a hydrophobic inner cavity combined with a hydrophilic exterior which conveys water solubility. Upon combination with a hydrophobic drug, such as a neuroactive steroid, the neuroactive steroid (i.e., the guest) inserts into the hydrophobic interior of the cyclodextrin (i.e., the host). The host-guest complex retains water solubility as a consequence of the hydrophobic exterior of the cyclodextrin ring.

Figure 6:
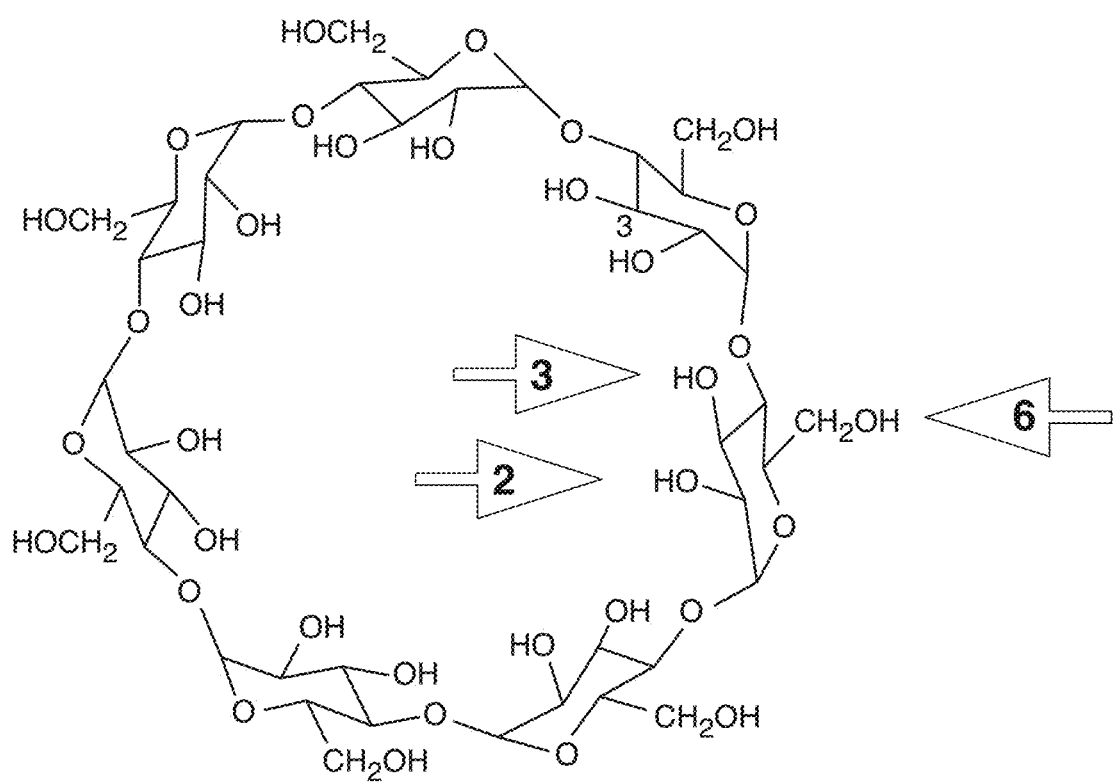
FIG. 6 is an exemplary depiction of a cyclodextrin.

Neuroactive steroid-cyclodextrin complexes, as shown in FIG. 6, can, as solubility permits, be incorporated into any of the parenteral and non-parenteral formulations described below. If desired, the aqueous solubility of solid neuroactive steroid-cyclodextrin complexes can be further enhanced by isolating the neuroactive steroid-cyclodextrin complex as a solid via lyophilization and/or via micronizing the solid neuroactive steroid-cyclodextrin complex.

This cyclic orientation provides a truncated cone structure that is hydrophilic on the exterior and lipophilic on the interior. Cyclodextrin complexes are formed when a guest molecule is partially or fully contained in the interior of the cavity. The parent α-, β-, and γ-cyclodextrins (particularly β) have limited aqueous solubility and show toxicity when given parenterally. Therefore, the parent cyclodextrin structure can be chemically modified to generate a parenterally safe CD-derivative. The modifications are typically made at one or more of the 2, 3, or 6 position hydroxyls.

Neuroactive steroid-cyclodextrin complexes are preferably formed from a cyclodextrin selected from the group consisting of α-cyclodextrin, β-cyclodextrin, γ-cyclodextrin, and derivatives thereof. The cyclodextrin may be chemically modified such that some or all of the primary or secondary hydroxyl groups of the macrocycle, or both, are functionalized with a pendant group. Suitable pendant groups include, but are not limited to, sulfinyl, sulfonyl, phosphate, acyl, and $C_1$-$C_{12}$ alkyl groups optionally substituted with one or more (e.g., 1, 2, 3, or 4) hydroxy, carboxy, carbonyl, acyl, oxy, oxo; or a combination thereof. Methods of modifying these alcohol residues are known in the art, and many cyclodextrin derivatives are commercially available, including sulfo butyl ether β-cyclodextrins available under the trade name CAPTISOL® from Ligand Pharmaceuticals (La Jolla, Calif.).

Examples of suitable cyclodextrins for use in neuroactive steroid, e.g., allopregnanolone formulations, can include cyclodextrins disclosed in U.S. Pat. Nos. 5,874,418; 6,046,177; and 7,635,733, which are herein incorporated by reference. Other examples of suitable cyclodextrins for use in neuroactive steroid formulations non-exclusively include α-cyclodextrin; β-cyclodextrin; γ-cyclodextrin; methyl α-cyclodextrin; methyl β-cyclodextrin; methyl γ-cyclodextrin; ethyl β-cyclodextrin; butyl α-cyclodextrin; butyl β-cyclodextrin; butyl γ-cyclodextrin; pentyl γ-cyclodextrin; hydroxyethyl β-cyclodextrin; hydroxyethyl γ-cyclodextrin; 2-hydroxypropyl α-cyclodextrin; 2-hydroxypropyl β-cyclodextrin; 2-hydroxypropyl γ-cyclodextrin; 2-hydroxybutyl β-cyclodextrin; acetyl α-cyclodextrin; acetyl β-cyclodextrin; acetyl γ-cyclodextrin; propionyl β-cyclodextrin; butyryl β-cyclodextrin; succinyl α-cyclodextrin; succinyl β-cyclodextrin; succinyl γ-cyclodextrin; benzoyl β-cyclodextrin; palmityl β-cyclodextrin; toluenesulfonyl β-cyclodextrin; acetyl methyl β-cyclodextrin; acetyl butyl β-cyclodextrin; glucosyl α-cyclodextrin; glucosyl β-cyclodextrin; glucosyl γ-cyclodextrin; maltosyl α-cyclodextrin; maltosyl β-cyclodextrin; maltosyl γ-cyclodextrin; α-cyclodextrin carboxymethylether; β-cyclodextrin carboxymethylether; γ-cyclodextrin carboxymethylether; carboxymethylethyl β-cyclodextrin; phosphate ester α-cyclodextrin; phosphate ester β-cyclodextrin; phosphate ester γ-cyclodextrin; 3-trimethylammonium-2-hydroxypropyl β-cyclodextrin; sulfobutyl ether β-cyclodextrin; carboxymethyl α-cyclodextrin; carboxymethyl β-cyclodextrin; carboxymethyl γ-cyclodextrin, and combinations thereof.

Preferred cyclodextrins include, but are not limited to, alkyl cyclodextrins, hydroxy alkyl cyclodextrins, such as hydroxy propyl β-cyclodextrin, carboxy alkyl cyclodextrins and sulfoalkyl ether cyclodextrins, such as sulfo butyl ether β-cyclodextrin.

In particular embodiments, the cyclodextrin is a alpha, beta, or gamma cyclodextrin having a plurality of charges (e.g., negative or positive) on the surface. In more particular embodiments, the cyclodextrin is a β-cyclodextrin containing or comprising a plurality of functional groups that are negatively charged at physiological pH. Examples of such functional groups include, but are not limited to, carboxylic acid (carboxylate) groups, sulfonate ($RSO_3^-$), phosphonate groups, phosphinate groups, and amino acids that are negatively charged at physiological pH. The charged functional groups can be bound directly to the cyclodextrins or can be linked by a space, such as an alkylene chain. The number of carbon atoms in the alkylene chain can be varied, but is generally between about 1 and 10 carbons, preferably 1-6 carbons, more preferably 1-4 carbons. Highly sulfated cyclodextrins are described in U.S. Pat. No. 6,316,613.

In one embodiment, the cyclodextrins is a β-cyclodextrin functionalized with a plurality of sulfobutyl ether groups. Such a cyclodextrins is sold under the tradename CAPTISOL®.

CAPTISOL® is a polyanionic beta-cyclodextrin derivative with a sodium sulfonate salt separated from the lipophilic cavity by a butyl ether spacer group, or sulfobutylether (SBE). CAPTISOL® is not a single chemical species, but comprised of a multitude of polymeric structures of varying degrees of substitution and positional/regional isomers dictated and controlled to a uniform pattern by a patented manufacturing process consistently practiced and improved to control impurities.

CAPTISOL® contains six to seven sulfobutyl ether groups per cyclodextrin molecule. Because of the very low pKa of the sulfonic acid groups, CAPTISOL® carries multiple negative charges at physiologically compatible pH values. The four-carbon butyl chain coupled with repulsion of the end group negative charges allows for an "extension" of the cyclodextrin cavity. This often results in stronger binding to drug candidates than can be achieved using other modified cyclodextrins. It also provides a potential for ionic charge interactions between the cyclodextrin and a positively charged drug molecule. In addition, these derivatives impart exceptional solubility and parenteral safety to the molecule. Relative to beta-cyclodextrin, CAPTISOL® provides higher interaction characteristics and superior water solubility in excess of 100 grams/100 ml, a 50-fold improvement.

In other embodiments, the cyclodextrins has plurality of functional groups that are negatively charged at physiological pH. Suitable positively charged groups include, but are not limited to, quaternary ammonium groups. Exemplary cyclodextrins include, but are not limited to, mono-6(A)-butylammonium-6(A)-deoxy-beta-cyclodextrin tosylate (BuAM-beta-CD) and Amine- and guanidine-derivatised β-cyclodextrin (βCD).

Preferably, the cyclodextrin is present in an amount of from about 0.1% to about 40% w/w of the overall formulation, preferably from about 5% to about 40% w/w, more preferably about 10% to about 40% w/w, most preferably about 10% to about 35% w/w. In certain embodiments, the concentration of the cyclodextrins is from about 15% to about 35% w/w, preferably from about 20% to about 35% w/w, more preferably about 30% to about 35% w/w. In one embodiment, the formulation contains about 1 to about 2, preferably about 1.5 mg neuroactive steroid (e.g., allopregnanolone) per ml of cyclodextrin, e.g., CAPTISOL®.

b. Ion Exchange Resins

Ion exchange resins (IER) are high molecular weight water insoluble polymers containing or comprising fixed positively or negatively charged functional groups in their matrix, which have an affinity for oppositely charged counter ions. IER are solid insoluble high molecular weight poly electrolytes that can exchange with surrounding medium reversibly and stoichiometrically. IER are Styrene (Di Vinyl Benzene) copolymer containing or comprising Acidic groups: Carboxylic or sulphonic for Cation E.R.
Basic groups: Quaternary Ammonium for Anion E.R Based on the nature of the ionic species being interchanged, the IE process is known as either cation exchange (CE) or anion exchange (AE). The IE process is competitive in nature. In practice, drug in an ionic form (usually solution) is mixed with the appropriate IER form a complex, known as 'resinate'.

The performance of resinates are governed by several factors, such as:
1. The pH and temperature of the drug solution;
2. The molecular weight and charge intensity of the drug and IER;
3. Geometry;
4. Mixing speed;
5. Ionic strength of the drug solution;
6. Degree of cross linking and particle size of the IER;
7. The nature of solvent; and
8. Contact time between the drug species and the IER.

In general, IER consist of spherical beads of approximately 0.5-1.2 mm in diameter. The most common type is an opaque yellow in color, although other colors are also reported. The constitution of each spherical particle of IER is similar to that of a homogeneous gel. The shrinkage or expansion of the spherical volume that takes place is based on the ionic environment in which the IER is present.

A major drawback of controlled or sustained release systems is dose dumping, resulting in increased risk of toxicity. Ion exchange resins offers better drug retaining properties and prevention of dose dumping. The polymeric (physical) and ionic (chemical) properties of ion exchange resin will release the drugs more uniformly than that of simple matrices (because of physical properties only). Drug loaded onto the strong IER resinates provides simplest form of controlled or sustained release delivery system. Resinates can be filled directly in a capsule, suspended in liquids, suspended in matrices or compressed into tablets. Drug will be slowly released by ion exchange phenomenon and absorbed.

Microencapsulation of resinates provides better control over the drug release for oral or depo release. The absorption of the drug from coated resinates is a consequence of the entry of the counter ions into the coated resinates and release of drug ions from drug resin complex by the ion exchange process and diffusion of drug ions through the membrane into the dissolution medium. Designed release rate at the desired level can be obtained by optimization of coating thickness. Microencapsulation of resinates can be achieved by air suspension coating (Wurster process), interfacial polymerization, solvent evaporation or pan coating.

Modification of the coating of resinates for example, by pretreatment with polyethylene glycol 400, can be used to maintain the geometry and improve coating process. The pretreated resinates are then coated with ethyl cellulose or any other water insoluble polymer. The polyethylene glycol helps in controlling the swelling rate of matrix in water, while an outer ethyl cellulose coating modifies the diffusion pattern of ions in and out of system. A major drawback of controlled or sustained release systems is dose dumping, resulting in increased risk of toxicity. Ion exchange resins offers better drug retaining properties and prevention of dose dumping. The polymeric (physical) and ionic (chemical) properties of ion exchange resin release the drugs more uniformly than that of simple matrices.

Drug loaded onto the strong IER resinates provides simplest form of controlled or sustained release delivery system. Resinates can be filled directly in a capsule, suspended in liquids, suspended in matrices or compressed into tablets. Drug will be slowly released by ion exchange phenomenon and absorbed.

There are a few ion exchange resins suitable for intravenous administration of drug. For example, Shimada, et al., in Jpn J. Antibiot. 1985 September; 38(9):2496-502, describes a clinical study on unmodified intravenous dried ion-exchange resin treated human normal immunoglobulin, SM-4300 that showed efficacy with no obvious antipyretic effect, opsonic effect or healing impairment.

c. Lipid Carriers

To facilitate the administration of neuroactive steroids possessing poor aqueous solubility, a variety of lipid carriers may be used.

Lipid Emulsions

Neuroactive steroids can be combined suspended or dissolved using a lipid emulsion. Lipid emulsions are known in the art. See, for example, U.S. Pat. No. 6,361,792 to Long, et. al.; U.S. Pat. No. 7,550,155 to Zhang, et al., and U.S. Patent Application Publication No. US 2006/0067952. Lipid emulsions formulations typically include one or more neuroactive steroids, an oil component, an emulsifier, and water.

The oil component can be a monoglyceride, a diglyceride, a triglyceride, or combinations thereof. In some cases, the oil component includes an ester formed between one or more fatty acids and an alcohol other than glycerol. The oil component can be, for example, a vegetable oil such as almond oil, borage oil, black currant seed oil, corn oil, safflower oil, soybean oil, sesame oil, cottonseed oil, peanut oil, olive oil, rapeseed oil, coconut oil, palm oil, canola oil, or combinations thereof. Vegetable oils are typically long-chain triglycerides formed from $C_{14}$-$C_{22}$ fatty acids. The oil component can also include medium chain triglycerides formed from C8-C12 fatty acids, such as Miglyol 812, Crodamol® GTCC-PN, or Neobees M-5 oil.

The emulsifier serves to stabilize the lipid emulsion by preventing separation of the emulsion into individual oil and aqueous phases. Suitable emulsifiers include, but are not limited to, propylene glycol mono- and di-fatty acid esters, polyoxyethylene sorbitan fatty acid esters, polyoxyethylene fatty acid esters, polyoxyethylene-polyoxypropylene co-polymers and block co-polymers, salts of fatty alcohol sulphates, sorbitan fatty acid esters, esters of polyethylene-glycol glycerol ethers, oil and wax based emulsifiers, glycerol monostearate, glycerine sorbitan fatty acid esters and phospholipids. In some cases the emulsifier is a phospholipid.

In some cases, the emulsifier is a vitamin E derivative. Suitable vitamin E derivatives include, but are not limited to, α-tocopheryl oxalate, α-tocopheryl malonate, α-tocopheryl succinate, α-tocopheryl glutarate, α-tocopheryl adipate, α-tocopheryl pimelate, α-tocopheryl suberate, α-tocopheryl azelate, and D-α-tocopheryl polyethylene glycol 1000 succinate (vitamin E TPGS).

Exemplary phospholipids include, phosphatidyl chlorine, lecithin (a mixture of choline ester of phosphorylated diacylglyceride), phosphatidylethanolamine, phosphatidylglycerol, phosphatidic acid with about 4 to about 22 carbon atoms, and more generally from about 10 to about 18 carbon atoms and varying degrees of saturation. Preferably, the phospholipid is of natural origin. Naturally occurring phospholipids include soy lecithin, egg lecithin, hydrogenated soy lecithin, hydrogenated egg lecithin, sphingosine, gangliosides, and phytosphingosine, and combinations thereof.

Suitable lipid emulsions generally contain between about 1% and 40% w/v oil component and between about 0.1% and 7.5% w/v emulsifier. Suitable commercially available lipid emulsions include lipid emulsions containing or comprising soybean oil, such as Intralipid® 10%, Intralipid® 20%, and Intralipid® 30%, as well as lipid emulsions containing or comprising a mixture of soybean and safflower oils, such as Liposyn® II 10% and Liposyn® II 20%.

Lipid emulsions can optionally contain one or more additional components. For example, lipid formulations can contain one or more non-aqueous miscible co-solvents, such as an alcohol or glycol. In some preferred formulations, glycerol and/or propylene glycol is present as a co-solvent.

Many lipid emulsions are capable of supporting bacterial growth. Accordingly, in some cases, one or more components may be added to the lipid emulsion formulation to prevent or retard bacterial growth, for example disodium edatate, citric acid, metabisulfate, benzyl alcohol, one or more parabens, chlorobutanol, phenol, sorbic acid, or thimerosal.

Additionally, lipid emulsions can contain one or more agents used to modify or stabilize the pH of the solution, including phosphate buffers, acetate buffers, and citrate buffers.

In one embodiment, the formulation is an oil-in-water emulsion containing or comprising a therapeutically effective amount of one or more neuroactive steroids dissolved in a solution containing or comprising between about 1% w/v and about 25% w/v soybean oil, between about 0.5% and about 7.5% w/v egg yolk phospholipid, and between about 0.5% w/v and about 5% w/v of a miscible co-solvent.

In another embodiment, the formulation is an oil-in-water emulsion containing or comprising a therapeutically effective amount of one or more neuroactive steroids dissolved in a solution containing or comprising between about 1% w/v and about 15% w/v soybean oil, between about 1% w/v and about 15% w/v safflower oil, between about 0.5% and about 7.5% w/v egg phosphatides, and between 0.5% w/v and about 5% w/v of a miscible co-solvent.

Lipid emulsions can be administered as described above, or incorporated into the parenteral formulations described below.

Liposomes

One or more neuroactive steroids can be incorporated into liposomes. As is known in the art, liposomes are generally derived from phospholipids or other lipid substances. See, for example, "Remington—The science and practice of pharmacy", 20th Edition, Jennaro et. al., (Phila, Lippencott, Williams, and Wilkens, 2000).

Liposomes are generally derived from phospholipids or other lipid substances. Liposomes are formed by mono- or multi-lamellar hydrated liquid crystals that are dispersed in an aqueous medium. Any nontoxic, physiologically acceptable and metabolizable lipid capable of forming liposomes can be used. The disclosed compositions in liposome form can contain, in addition to one or more neuroactive steroids, stabilizers, preservatives, excipients, and other suitable excipients.

Examples of suitable lipids are the phospholipids and the phosphatidylcholines (lecithins), both natural and synthetic. Methods of forming liposomes are known in the art. See, e.g., Prescott, Ed., Methods in Cell Biology, Volume XIV, Academic Press, New York p. 33 et seq., 1976. The liposomes can be cationic liposomes (e.g., based on DOTMA, DOPE, DC cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract.

One or more neuroactive steroids can formulated using commercially available liposome preparations such as LIPOFECTIN®, LIPOFECTAMIE® (GIBCO-BRL, Inc., Gaithersburg, Md.), SUPERFECT® (Qiagen, Inc. Hilden, Germany) and TRANSFECTAM® (Promega Biotec, Inc., Madison, Wis.), as well as other liposomes developed according to procedures standard in the art. Liposomes where the diffusion of the compound or delivery of the compound from the liposome is designed for a specific rate or dosage can also be used.

One or more neuroactive steroids can also be formulated using noisomes. Noisomes are multilamellar or unilamellar vesicles involving non-ionic surfactants. An aqueous solution of solute is enclosed by a bilayer resulting from the organization of surfactant macromolecules. Similar to liposomes, noisomes are used in targeted delivery of, for example, anticancer drugs, including methotrexate, doxorubicin, and immunoadjuvants. They are generally understood to be different from transfersomes, vesicles prepared from amphiphilic carbohydrate and amino group containing or comprising polymers, e.g., chitosan.

One or more neuroactive steroids can also be delivered using nanoerythrosomes. Nanoerythrosomes are nanovesicles made of red blood cells via dialysis through filters of defined pore size. These vesicles can be loaded with one or more neuroactive steroids.

Lipid Nanoemulsions

Lipid nanoemulsions can also be used. Lipid nanoemulsions are known in the art. See, for example, U.S. Patent Application Publication No. US 2007/0207173 to Chen, et al, and U.S. Patent Application Publication No. US 2001/0045050 to Elbayoumi, et al. Lipid nanoemulsions can be prepared by microemulsification of any of the lipid emulsions described above using for example, a high pressure homogenizer, or via a phase inversion temperature method (PIT).

In preferred lipid nanoemulsions containing or comprising neuroactive steroids, vitamin E succinate and/or Vitamin E TPGS are included as emulsifiers.

The lipid nanoemulsion can further be lyophilized if desired. See, for example, U.S. Patent Publication No. US 2011/0015266.

Lipid and emulsions can be administered as described above, or incorporated into the parenteral or non-parenteral formulations described below.

The pre-concentrate includes an oil phase which has at least one fatty acid oil. Fatty acid oils of the present invention include at least one polyunsaturated fatty acid. The term "polyunsaturated fatty acid" include those fatty acids having at least 50 weight percent or more of polyunsaturated fatty acids. Polyunsaturated fat can be found in grain products, fish and sea food (herring, salmon, mackerel, halibut), soybeans, and fish oil. Polyunsaturated fatty acids include omega-3 fatty acids and omega-6 fatty acids. Polyunsaturated fatty acids include linolic acid and linolenic acid. Preferable polyunsaturated fatty acids include eicosapentaenoic acid, salts of eicosapentaenoic acid, docosahexaenoic acid, salts of docosahexaenoic acid, triglycerides of eicosapentaenoic acid, triglycerides of docosahexaenoic acid, ethyl esters of eicosapentaenoic acid, or ethyl esters of docosahexaenoic acid.

Polyunsaturated fatty acids include omega-3 fatty acid oils and medium chain triglycerides (MCT). A medium chain triglyceride contains about 6 to 14 carbon atoms, preferably about 8 to 12 carbon atoms are suitable for use in the oil phase. Preferable medium chain glyceride includes, for example, caprylic/capric triglyceride such as "Migriol 810", "Migriol 812" (both trade names, manufactured by Huls Co., Ltd., available from Mitsuba Trading Co., Ltd.), a glyceryl tricaprylate (tricaprylin) such as "Panasate 800" (trade name, manufactured by NOF Corporation, Japan).

The pre-concentrate includes an emulsifier component. The emulsifier component has one or more surfactants. Surfactants include any molecule having both a polar head group, which energetically prefers solvation by water, and a hydrophobic tail that is not well solvated by water. The ratio of the oil phase to the emulsifier component is important for the toxicity of the nanoemulsion prepared from the pre-concentrate. Surfactants suitable for use with the pre-concentrate and emulsion include a variety of anionic and nonionic surfactants, as well as other emulsifying compounds that are capable of promoting the formation of oil-in-water emulsions; so long as they are on the GRAS (Generally Recognized as Safe) list and are approved for human consumption such as lecithin, solutol HS-15 (polyoxyethylene esters of 12-hydroxystearic acid), polysorbate 80 or Cremophore EL (polyethoxylated castor oil). See McCutcheon's Volume 1: Emulsifiers and Detergents North American Edition, 1996 (incorporated herein by reference).

2. Formulations for Parenteral Administration

The compounds described herein can be formulated for parenteral administration. "Parenteral administration", as used herein, refers to intravenous or intraarterial administration.

Particle Size Reduction

The solubility of one or more neuroactive steroids can be improved by decreasing drug particle size. By decreasing particle size, the surface area to volume ratio of the drug particles is increased, resulting in increased solvation of the drug particle.

Particle size reduction can be achieved using a variety of micronization techniques including, but not limited to, grinding, milling (e.g., air-attrition milling (jet milling), ball milling), coacervation, high pressure homogenization, spray drying, and/or supercritical fluid crystallization. In some instances, particles are sized by mechanical impact (e.g., by hammer mills, ball mill and/or pin mills). In some instances, particles are sized via fluid energy (e.g., by spiral jet mills, loop jet mills, and/or fluidized bed jet mills). After micronization, the drug particles can be further processed. For example, the micronized drug particles may be coated to further influence solubility and/or drug release.

Depending on the micronization process and active agent involved, the micronized drug particles can be crystalline or amorphous. Using micronization techniques, drug particles ranging from 10 nm to 100 microns can be formed. The average particle size and distribution of the drug particles can be controlled through the selection of micronization technique as well as by variation of process conditions. Accordingly, formulations of drug particles can be prepared which contain nanoparticles of drug, microparticles of drug, and combinations thereof. Appropriate micronization techniques can be selected to produce populations of drug particles with monodisperse or polydisperse particle size distributions. Methods of producing monodisperse drug particles are known in the art. Alternatively, populations of drug particles can be separated following micronization to obtain drug particle populations with the desired size range and distribution.

In addition to improving solubility, micronization can also be used to control drug release profiles. As different sized drug particles will dissolve at different rates and over different periods of time, micronization can be used to prepare controlled release, sustained release, pulsatile release, and delayed release formulations. For example, populations of micronized drug particles with different average particle sizes and/or different particle size distributions can be mixed. The resulting mixtures will exhibit a drug release profile which is the combination of the drug release profile of component populations of drug particles. In some embodiments, micronized drug particles containing or comprising different neuroactive steroids can be mixed to effect combination therapy.

Micronized drug particles can be incorporated into any of the parenteral and non-parenteral formulations described below as a suspension or dispersion in a solid or fluid carrier. Micronized drug particles can also be used to form solutions for parenteral or non-parenteral administration. Micronized drug particles can also be provided, for example, in a kit used to prepare solutions or suspensions for injection.

Aqueous Compositions

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing or comprising, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof.

The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing or comprising carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-□-alanine, sodium N-lauryl-□-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

a. Controlled Release Formulations

The parenteral formulations described herein can be formulated for controlled release including immediate release, delayed release, extended release, pulsatile release, and combinations thereof.

Nano- and Microparticles

For parenteral administration, the compounds, and optionally one or more additional active agents, can be incorporated into microparticles, nanoparticles, or combinations thereof that provide controlled release. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into polymeric microparticles which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers which are slowly soluble and form a gel in an aqueous environment, such as hydroxypropyl methylcellulose or polyethylene oxide may also be suitable as materials for drug containing or comprising microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

In some cases, it may be desirable to alter the rate of water penetration into the microparticles. To this end, rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethylcellulose, hydroxypropylcellulose, methylcellulose, and carboxymethylcellulose), alginic acid, lactose and talc. Additionally, a pharmaceutically acceptable surfactant (for example, lecithin) may be added to facilitate the degradation of such microparticles.

Proteins which are water insoluble, such as zein, can also be used as materials for the formation of drug containing or comprising microparticles. Additionally, proteins, polysaccharides and combinations thereof which are water soluble can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug containing or comprising microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. Detailed descriptions of these processes can be found in "Remington—The science and practice of pharmacy", 20th Edition, Jennaro et. al., (Phila, Lippencott, Williams, and Wilkens, 2000).

For some carrier materials it may be desirable to use a solvent evaporation technique to produce drug containing or comprising microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing or comprising microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin (Cortesi, R., et al., *Biomaterials* 19 (1998) 1641-1649). Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing or comprising microparticles or drug particles, a water soluble protein can be spray coated onto the microparticles and subsequently cross-linked by the one of the methods described above. Alternatively, drug containing or comprising microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

3. Formulations for Non-Parenteral Administration

Neuroactive steroids can be formulated for non-parenteral administration. Non-parenteral formulations may be useful for oral, subcutaneous, intra-peritoneal, intramuscular, transdermal, nasal, pulmonary, or mucosal delivery.

a. Depot Formulations

Neuroactive steroids, including progesterone and progesterone analogues such as decanoate salts or esters of progesterone, can be formulated for depot injection. In a depot injection, the active agent is formulated with one or more pharmaceutically acceptable carriers that provide for the gradual release of active agent over a period of hours or days after injection. The depot formulation can be administered by any suitable means; however, the depot formulation is typically administered via subcutaneous or intramuscular injection.

A variety of carriers may be incorporated into the depot formulation to provide for the controlled release of the active agent. In some cases, depot formulations contain one or more biodegradable polymeric or oligomeric carriers. Suitable polymeric carriers include, but are not limited to poly(lactic acid) (PLA), poly(lactic-co-glycolic acid) (PLGA), poly(lactic acid)-polyethyleneglycol (PLA-PEG) block copolymers, polyanhydrides, poly(ester anhydrides), polyglycolide (PGA), poly-3-hydroxybutyrate (PHB) and copolymers thereof, poly-4-hydroxybutyrate (P4HB), polycaprolactone, cellulose, hydroxypropyl methylcellulose, ethylcellulose, as well as blends, derivatives, copolymers, and combinations thereof.

In depot formulations containing or comprising a polymeric or oligomeric carrier, the carrier and active agent can be formulated as a solution, an emulsion, or suspension. One or more neuroactive steroids, and optionally one or more additional active agents, can also be incorporated into polymeric or oligomeric microparticles, nanoparticles, or combinations thereof.

In some cases, the formulation is fluid and designed to solidify or gel (i.e., forming a hydrogel or organogel) upon injection. This can result from a change in solubility of the composition upon injection, or for example, by injecting a pre-polymer mixed with an initiator and/or crosslinking agent. The polymer matrix, polymer solution, or polymeric particles entrap the active agent at the injection site. As the polymeric carrier is gradually degraded, the active agent is released, either by diffusion of the agent out of the matrix and/or dissipation of the matrix as it is absorbed. The release rate of the active agent from the injection site can be controlled by varying, for example, the chemical composition, molecular weight, crosslink density, and concentration of the polymeric carrier. Examples of such systems include those described in U.S. Pat. Nos. 4,938,763, 5,480,656 and 6,113,943.

Depot formulations can also be prepared by using other rate-controlling excipients, including hydrophobic materials, including acceptable oils (e.g., peanut oil, corn oil, sesame oil, cottonseed oil, etc.) and phospholipids, ion-exchange resins, and sparingly soluble carriers.

The depot formulation can further contain a solvent or dispersion medium containing or comprising, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the neuroactive compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing or comprising carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

b. Gels

Formulations may be in the form of an organogel (assuming the neuroactive steroid is relatively water insoluble) or a hydrogel. Numerous gel formulations are known. See, for example, U.S. Pat. No. 5,411,737 by Hsu, et al. Hydrogels, especially those further including nanoparticles microparticles for sustained, immediate and/or delayed release, can also be used. See, for example, U.S. Pat. No. 6,589,549 to Shih, et al.

U.S. patent application No. 20100295113 by Hoffman, et al., describes a composite hydrogel including a blend of an aqueous solution of an anionic polysaccharide or a derivative thereof, such as or a derivative thereof and an aqueous solution of methylcellulose or another water soluble cellulose derivative thereof, having dispersed polymeric particles, such as polymeric micro particles and nanoparticles, and wherein the stability of the hydrogel is enhanced relative to the stability of the hydrogel alone. The polymeric particles may contain at least one therapeutic agent, in which case each therapeutic agent exhibits a linear sustained release rate that can be tuned or altered by selecting the appropriate polymer formulation of the micro particles and/or nanoparticles. The composite may be injectable, and in the absence of a therapeutic agent may be used as a bulking agent for reconstructive and cosmetic surgery or may act as a platform for subsequent delivery of therapeutic agents.

See also, Salem, *Int J Nanomedicine*. 2010 Nov. 10; 5:943-54, describing a sustained release form of natural progesterone to be given as IM injection. A progesterone nanosuspension (PNS) was first developed and then dispersed in a thermosensitive gel matrix. The selected nanoparticles showed an average particle size of 267 nm and a zeta potential approaching-41 mV. The in vitro release profile of PNS from Pluronic F127 plus methyl cellulose gel followed zero order kinetics and correlated linearly with the weight percentage of gel dissolved, demonstrating that the overall rate of release of PNS is controlled by dissolution of the pluronic F127/methyl cellulose (MC) gel.

Gels can also be administered in combination with oral or subcutaneously administered drug. See, for example, Tomic, et al., Gynecol Endocrinol. 2011 Apr. 19.

c. Oral Formulations

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes but is not limited to diluents, binders, lubricants, disintegrators, fillers, matrix-forming compositions and coating compositions.

"Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", $6^{th}$ Edition, Ansel et. al., (Media, Pa.: Williams and Wilkins, 1995) which provides information on carriers, materials, equipment and processes for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing or comprising tablets, beads, granules or particles include, but are not limited to, diluents, binders, lubricants, disintegrants, colorants, stabilizers, and surfactants. Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pre-gelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pre-gelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Some of the materials which are suitable as binders can also be used as matrix-forming materials such as hydroxypropyl methyl cellulose, ethyl cellulose, and microcrystalline cellulose.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pre-gelatinized starch, clays, cellulose, alginine, gums or cross linked polymers, such as cross-linked PVP (Polyplasdone® XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing or comprising carboxylate, sulfonate and sulfate ions. Examples of anionic surfactants include sodium, potassium, ammonium salts of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads, granules or particles may also contain minor amount of nontoxic auxiliary substances such as wetting or emulsifying agents, dyes, pH buffering agents, and preservatives.

The delayed-release portion is designed to prevent drug release after a defined period of time. Although oral is not a preferred route of administration, in the case of an orally delivered formulation, this would be in the upper part of the gastrointestinal (GI) tract. Delayed release in an oral formulation can be achieved using enteric coatings. The enteric coated formulation remains intact or substantially intact in the stomach but dissolves and releases the contents of the dosage form once it reaches the small intestine. Other types of coatings can be used to provide delayed release following injection subcutaneously, intra-tissue or intramuscularly at a site near or at the area to be treated.

Extended Release Dosage Forms

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkyl-celluloses such as hydroxypropylcellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is included of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer includes a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit®

RS30D. The mean molecular weight is about 150,000. Eudragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form including single or multiple units. Examples of multiple units include, but are not limited to, multilayer tablets and capsules containing or comprising tablets, beads, or granules.

An immediate release portion can be added to the extended release system by means of either applying an immediate release layer on top of the extended release core using a coating or compression process or in a multiple unit system such as a capsule containing or comprising extended and immediate release beads.

Extended release tablets containing or comprising hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing or comprising wax materials are generally prepared using methods known in the art such as a direct blend method, a congealing method, and an aqueous dispersion method. In the congealing method, the drug is mixed with a wax material and either spray-congealed or congealed and screened and processed.

Delayed Release Dosage Forms

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing or comprising composition with a selected coating material. The drug-containing or comprising composition may be, e.g., a tablet for incorporation into a capsule, a tablet for use as an inner core in a "coated core" dosage form, or a plurality of drug-containing or comprising beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion.

Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Methods of Manufacturing

As will be appreciated by those skilled in the art and as described in the pertinent texts and literature, a number of methods are available for preparing drug-containing or comprising tablets, beads, granules or particles that provide a variety of drug release profiles. Such methods include, but are not limited to, the following: coating a drug or drug-containing or comprising composition with an appropriate coating material, typically although not necessarily, incorporating a polymeric material, increasing drug particle size, placing the drug within a matrix, and forming complexes of the drug with a suitable complexing agent.

The delayed release dosage units may be coated with the delayed release polymer coating using conventional techniques, e.g., using a conventional coating pan, an airless spray technique, fluidized bed coating equipment (with or without a Wurster insert), or the like. For detailed information concerning materials, equipment and processes for preparing tablets and delayed release dosage forms, see Pharmaceutical Dosage Forms: Tablets, eds. Lieberman et al. (New York: Marcel Dekker, Inc., 1989), and Ansel et al., Pharmaceutical Dosage Forms and Drug Delivery Systems, 6.sup.th Ed. (Media, Pa.: Williams & Wilkins, 1995).

Alternatively, a delayed release tablet may be formulated by dispersing the drug within a matrix of a suitable material such as a hydrophilic polymer or a fatty compound. The hydrophilic polymers may be included of polymers or copolymers of cellulose, cellulose ester, acrylic acid, methacrylic acid, methyl acrylate, ethyl acrylate, and vinyl or enzymatically degradable polymers or copolymers as described above. These hydrophilic polymers are particularly useful for providing a delayed release matrix. Fatty compounds for use as a matrix material include, but are not limited to, waxes (e.g. carnauba wax) and glycerol tristearate. Once the active ingredient is mixed with the matrix material, the mixture can be compressed into tablets.

A preferred method for preparing extended release tablets is compressing a drug-containing or comprising blend, e.g., blend of granules, prepared using a direct blend, wet-granulation, or dry-granulation process. Extended release tablets may also be molded rather than compressed, starting with a moist material containing or comprising a suitable water-soluble lubricant. However, tablets are preferably manufactured using compression rather than molding. A preferred method for forming an extended release drug-containing or comprising blend is to mix drug particles directly with one or more excipients such as diluents (or fillers), binders, disintegrants, lubricants, glidants, and colorants. As an alternative to direct blending, a drug-containing or comprising blend may be prepared by using wet-granulation or dry-granulation processes. Beads containing or comprising the active agent may also be prepared by any one of a number of conventional techniques, typically starting from a fluid dispersion. For example, a typical method for preparing drug-containing or comprising beads involves dispersing or dissolving the active agent in a coating suspension or solution containing or comprising pharmaceutical excipients such as polyvinylpyrrolidone, methylcellulose, talc, metallic stearates, silicone dioxide, plasticizers or the like. The admixture is used to coat a bead core such as a sugar sphere (or so-called "non-pareil") having a size of approximately 60 to 20 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

d. Implants

Neuroactive steroid can also be administered by insertion of an implant such as the silastic tube used for delivery of contraceptive hormones. See, for example, Levonorgestrel and Norplant, both of which delivery long term release of hormone for contraception, following subdermal implantation. The effective dosage is increased by increasing the size of the hole by which drug exits the reservoir to the individual to be treated.

e. Transdermal Patches

Neuroactive steroid can also be administered by a transdermal patch, similar to those used for contraception, although in a significantly higher dosage. See, for example, the Transdermal CombiPatch (estradiol/norethindrone) and the Testogen™ TDS®-enhanced testosterone. Dosage can be increased by increasing the release mechanisms and/or increasing the concentration in the patch.

D. Combinations with Other Active Compounds

Neuroactive steroid can be administered adjunctively with other active compounds such as analgesics, anti-inflammatory drugs, antipyretics, antiepileptics, antihistamines, antimigraine drugs, antimuscarinics, anxioltyics, sedatives, hypnotics, antipsychotics, bronchodilators, anti asthma drugs, cardiovascular drugs, corticosteroids, dopaminergics, electrolytes, parasympathomimetics, stimulants, anorectics and anti-narcoleptics.

All publications cited are incorporated by reference.

III. Administration of Neuroactive steroid Formulations

A composition described herein, can be administered to a subject in need thereof, to treat a disorder, e.g., a CNS related disorder, e.g., a traumatic brain injury; e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; a seizure, e.g., acute repetitive seizures, cluster seizures. Although preferred patients are human, typically any mammal including domestic animals such as dogs, cats and horses, may also be treated.

Traumatic Brain Injury

The amount of the active ingredients to be administered is chosen based on the amount which provides the desired dose to the patient in need of such treatment to alleviate symptoms or treat a condition. Behavioral assays can be used to determine the rate and extent of behavior recovery in response to the treatment. Improved patient motor skills, spatial learning performance, cognitive function, sensory perception, speech and/or a decrease in the propensity to seizure may also be used to measure the neuroprotective effect. Such functional/behavioral tests used to assess sensorimotor and reflex function are described in, for example, Bederson et al. (1986) Stroke 17:472-476, DeRyck et al. (1992) Brain Res. 573:44-60, Markgraf et al. (1992) Brain Res. 575:238-246, Alexis et al. (1995) Stroke 26:2336-2346.

Enhancement of neuronal survival may also be measured using the Scandinavian Stroke Scale (SSS) or the Barthl Index.

The treatment of a traumatic brain injury can be monitored by employing a variety of neurological measurements. For example, a partial therapeutic responses can be monitored by determining if, for example, there is an improvement in the subjects a) maximum daily Glasgow Coma Score; b) duration of coma; 3) daily intracranial pressure-therapeutic intensity levels; 4) extent of cerebral edema/mass effect measured on serial CT scans; and, 5) duration of ventilator support. A brief description of each of these assays is provided below.

The Glasgow Coma Score (index GCS) is a reflection of the depth of impaired consciousness and is best obtained following initial resuscitation (oxygenation, rehydration and support of blood pressure) but prior to use of sedating drugs, neuromuscular blocking agents, or endotracheal intubation.

The duration of coma is defined as the number of hours from the time of injury that the subject is unable to purposefully respond to commands or mechanical stimulation. For non-intubated subjects, this equates to a GCS score of >8. For intubated patients, this correlates with a GCS motor score of .gtoreq.5. Duration of coma has been found to be predictive of functional outcome (Uhler et al. (1994) Neurosurgery 34(1): 122-8; Jiang et al. (1996) Brain Res 735(1): 101-7; and Gonzalez-Vidal et al. (1998) Arch Med Res 29(2): 117-24). Time spent in a coma induced pharmacologically for reasons other than brain injury should be subtracted in the final analysis.

The intracranial pressure (ICP) of patients with severe TBI is often monitored with an intracranial pressure device. Monitoring ICP can provide a measure of cerebral edema. However, inherent variability and analysis complexities due to therapeutic interventions intended on lowering the ICP mire using ICP measurements. To adjust for these interventions a therapeutic intensity scale was developed. This scale, known as the Therapeutic Intensity Level (TIL), measures treatment aggressiveness for elevated ICPs (Allolio et al. (1995) European Journal of Endocrinology 133(6): 696-700; Adashi et al. (1996) Reproductive endocrinology, surgery, and technology Philadelphia: Lippincott-Raven; and, Beers et al. eds. (1999) The Merck manual of diagnosis and therapy. 17th ed., Merck Sharp & Dohme Research Laboratories, Rahway, N.J.).

The extent of cerebral edema and mass effect can be determined by CT scans. For example, the volume of focal lesions can be measured. Mass lesions, either high-density or mixed-density abnormalities, will be evaluated by measuring the area of the abnormality as a region of interest, multiplying the area by the slice thickness, and summing these volumes for contiguous slices showing the same lesion. Each lesion will be measured three times, and the mean volume will be entered. This technique has been shown to be reliable (Garcia-Estrada et al. (1993) Brain Res 628(1-2): 271-8).

Intracerebral lesions can be further characterized by location (frontal, temporal, parietal, occipital, basal ganglia, or any combination). When an edematous zone is present, its volume (the hypodense perimeter) can be measured and analyzed separately. Midline shift will be measured using the septum pellucidum as the midline structure. The ventricle-brain ratio (VBR) will be calculated to quantify the degree of cerebral atrophy. Levin et al. ((1981) Archives of Neurology 38(10):623-9) found that the VBR had satisfactory reliability across different examiners, and was related both to the severity of acute injury and neurobehavioral sequelae (Hoffman et al. (1994) J Neurotrauma 11(4): 417-31).

The duration of ventilator support will be defined as the number of hours the patient receives positive pressure mechanical ventilation (Uhler et al. (1994) Veurosurgery 34(1): 122-8; Jiang et al. (1996) Brain Res 735(1): 101-7; and Gonzalez-Vidal et al. (1998) Arch Med Res 29(2): 117-24). Time spent under ventilator support for reasons other than brain injury will be subtracted in the final analysis.

In addition to the neurological measurements discussed above, a partial therapeutic response can also be assayed through various functional and neuropsychological outcomes. Several standardized measures of neuropsychological and functional performance are known. For instance subjects may display an improvement in the Glasgow Outcome Scale (GOS)/Glasgow Outcome Scale Extender (GOSE) and/or in the Disability Rating Scale (DRS). The Glasgow Outcome Score is one of the most widely used measures of brain injury recovery in the world (Garcia-Estrada et al. (1999) Int J Dev Neurosci 17(2): p. 145-51). Patients are classified into one of five categories: death, persistent vegetative state, severe disability, moderate disability, and good recovery. It is easy to administer and score, and has a high degree of reliability and validity.

The Disability Rating Scale (DRS) offers more precision than the GOS for measuring outcomes of moderate brain injury (Goodman et al. (1996) J Neurochem 66(5): 1836-44). The DRS consists of an eight-item rating of arousal and awareness, daily living activities, physical dependence, and employability (Vedder et al. (1999) J Neurochem 72(6): 2531-8). Inter-rater reliability for the entire DRS is high (0.97 to 0.98).

The Functional Independence Measure (FIM) can be used to assess physical and cognitive disability. It contains 18 items in the following domains: self-care, sphincter control, mobility, locomotion, communication, and social cognition (Baulieu (1997) Mult Scler 3(2): 105-12). The FIM has demonstrated reliability and validity as an outcome measure following moderate and severe TBI (Jung-Testas et al. (1994) J Steroid Biochem Mol Biol 48(1): 145-54).

The Sickness Impact Profile is one method for measuring self-perceived health status (Schumacher et al. (1995) Ciba Found Symp 191: p. 90-112 and Koenig et al. (1995) Science 268(5216):1500-3). It consists of 136 questions divided into 12 categories: sleep and rest, eating, work, home management, recreation and pastimes, ambulation, mobility, body care and movement, social interaction, alertness, behavior, emotional behavior, and communication. It has been widely used across a variety of diseases and injuries, including head injury (Thomas et al. (1999) Spine 24:2134-8). Baseline SIP scores will reflect pre-injury health status, while follow-up scores will examine post-injury functioning.

Ischemia

Global ischemia, as used herein in reference to the CNS, refers to a condition which results from a general diminution of blood flow to the entire brain, forebrain, or spinal cord, which causes the delayed death of neurons, particularly those in metabolically active loci, throughout these tissues.

Focal ischemia, as used herein in reference to the CNS, refers to a condition that results from the blockage of a single artery that supplies blood to the brain or spinal cord, resulting in the death of all cellular elements (pan-necrosis) in the territory supplied by that artery.

Epilepsy

Epilepsy is a brain disorder characterized by repeated seizures overtime. Types of epilepsy can include, but are not limited to generalized epilepsy, e.g., childhood absence epilepsy, juvenile nyoclonic epilepsy, epilepsy with grand-mal seizures on awakening, West syndrome, Lennox-Gastaut syndrome, partial epilepsy, e.g., temporal lobe epilepsy, frontal lobe epilepsy, benign focal epilepsy of childhood.

Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

Compositions described herein can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

Seizures

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures.

The present invention will be further understood by reference to the following non-limiting examples.

Example 1. Stability Studies of Formulations Comprising Allopregnanolone and CAPTISOL®

Materials and Methods

Formulations of allopregnanolone (1.5 mg/ml) and CAPTISOL® (6%) were evaluated for stability after storage at different temperatures and relative humidities over a 12 week period. The formulations were stored in an IntraVia flexible bag [multilayer polyolefin plastic, (PL 2408), non-latex, non-PVC, non-DEHP] or a vial (Type 1 glass vial with a 20 mm stopper, FluroTec, 4432/50 Westar). The samples were prepared from a stock solution of 250 ml of 6 mg/ml allopregnanolone in CAPTISOL®. The formulations were evaluated based on clarity/color, assay (potency), impurities (known, unknown, and total), osmolality, pH, bacterial endotoxins, and particulate matter.

Results

The studies demonstrated that the formulation was stable under all conditions that were tested for twelve weeks: refrigerated 2-5° C.; refrigerated 25° C./50% RH; refrigerated 40° C./75% RH; refrigerated 60° C.; refrigerated 2-5° C.; refrigerated 25° C./60% RH; refrigerated 40° C./75% RH; and refrigerated 60° C.

Example 2. Allopregnanolone Rescue of AGS SE in Fmr1 Knockout Mice

Figure 1B:
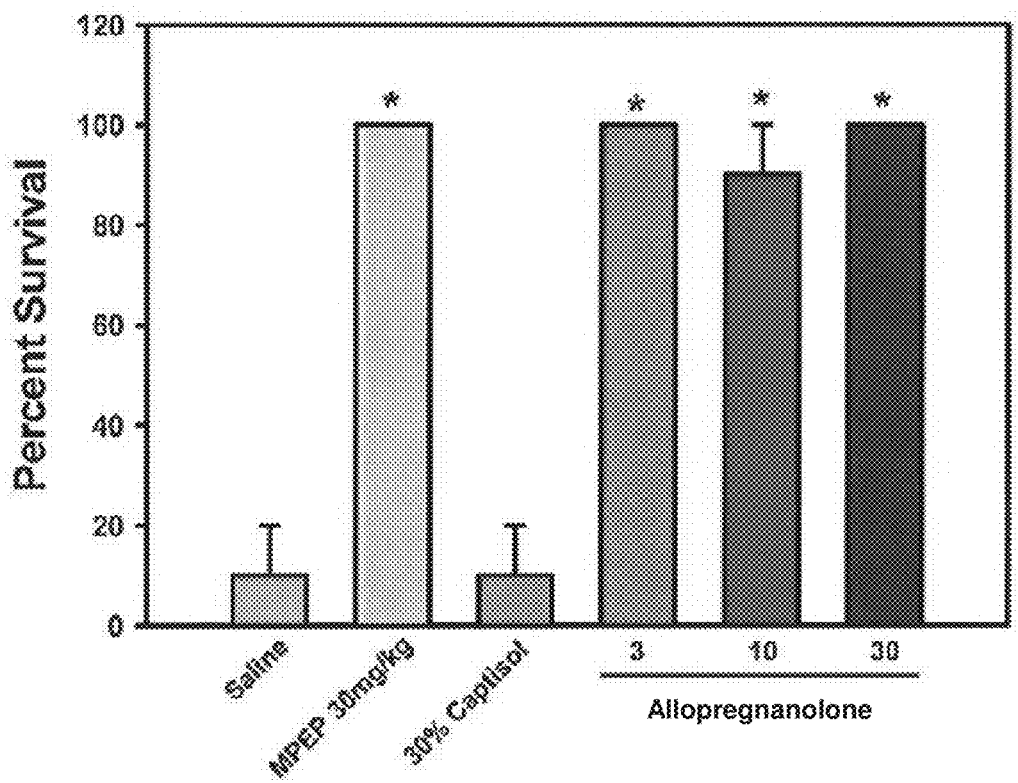
FIG. 1B is a bar graph depicting the percent survival in fmr1 KO mice intraperitoneally administered 3, 10, 30 mg/kg allopregnanolone in 30% β-Cyclodextrin.

Allopregnanolone reversed the sensitization to audiogenic seizure (AGS)—a form of status epilepticus (SE)—in Fmr1 KO mice at 3, 10, 30 mg/kg dosed intraperitoneal (IP) in 30% b-Cyclodextrin, as indicated by the significant decrease in Percent Seizure (FIG. 1A), and increase Percent Survival (FIG. 1B) relative to vehicle treated control. Plasma levels of six animals in each Allopregnanolone treatment group were collected randomly at completion of study and analyzed by LC-MS/MS. Bioanalytical measures are indicated in ng/mL (FIG. 1A). Data are presented as mean+/−SEM. *P<0.05 indicate a statistically significant difference relative to vehicle control by Fisher's PLSD. MPEP 30 mg/kg was used as a positive control in the study.

Figure 2A:
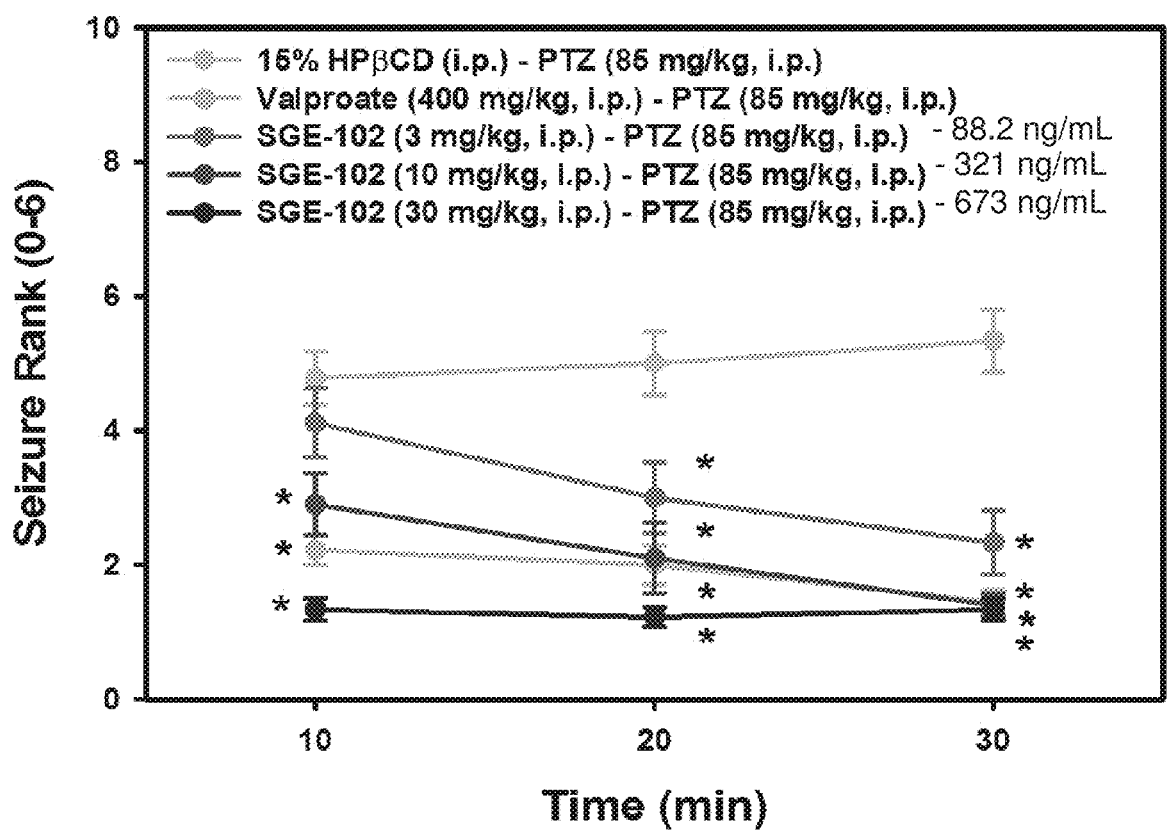
FIG. 2A is a graph depicting the seizure rank in PZT treated C57BL6/J mice intraperitoneally administered 3, 10, 30 mg/kg allopregnanolone in 15% β-Cyclodextrin.
Figure 2B:
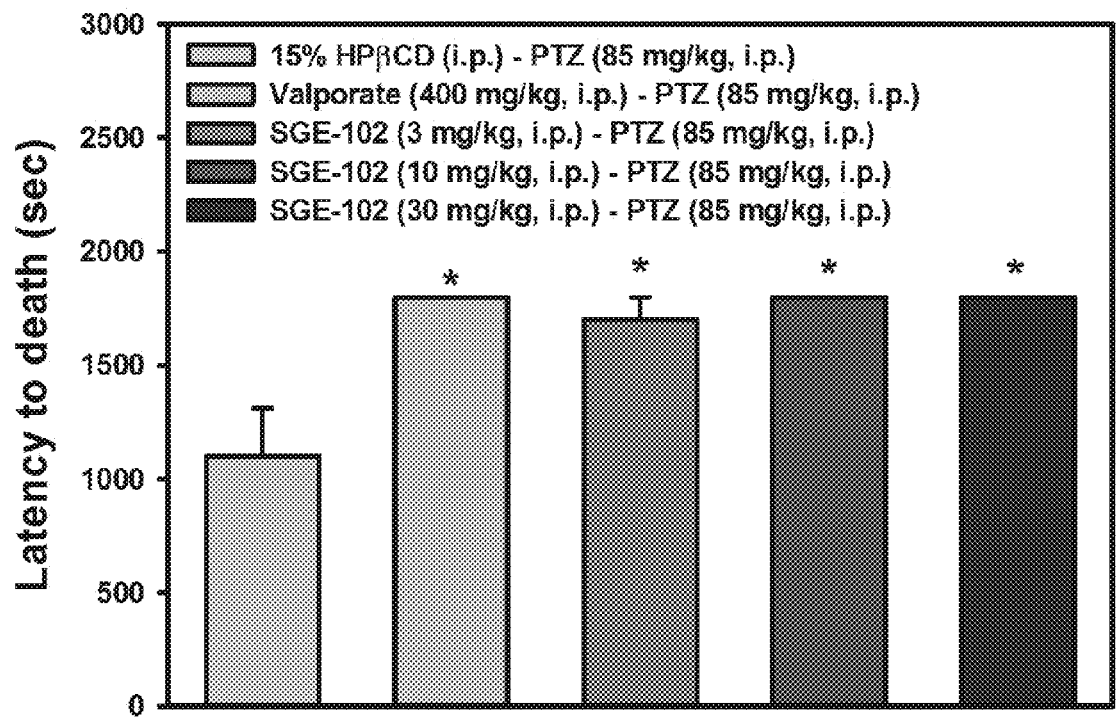
FIG. 2B is graph depicting the latency to death period in PZT treated C57BL65 mice intraperitoneally administered 3, 10, 30 mg/kg allopregnanolone in 15% β-Cyclodextrin.

Example 3. Allopregnanolone Prevention of Status Epilepticus in PZT-Seizure Model Allopregnanolone at 3, 10, 30 mg/kg dosed intraperitoneal (IP) in 15% β-Cyclodextrin prevented status epilepticus in PTZ (pentylenetetrazol) (85 mg/kg IP)-treated C57BL6/J mice, as indicated by the significant decrease in Seizure rank (FIG. 2A), and increase Latency to Death (FIG. 2B) relative to vehicle-treated control. Plasma levels of three animals in each Allopregnanolone treatment group were collected randomly at completion of study and analyzed by LC-MS/MS. Bioanalytical measures are indicated in ng/mL (FIG. 2A). Data are presented as mean+/−SEM. *P<0.05 indicate a statistically significant difference relative to vehicle control by Fisher's PLSD. Valproate 400 mg/kg was used as a positive control in the study.

Figure 3:
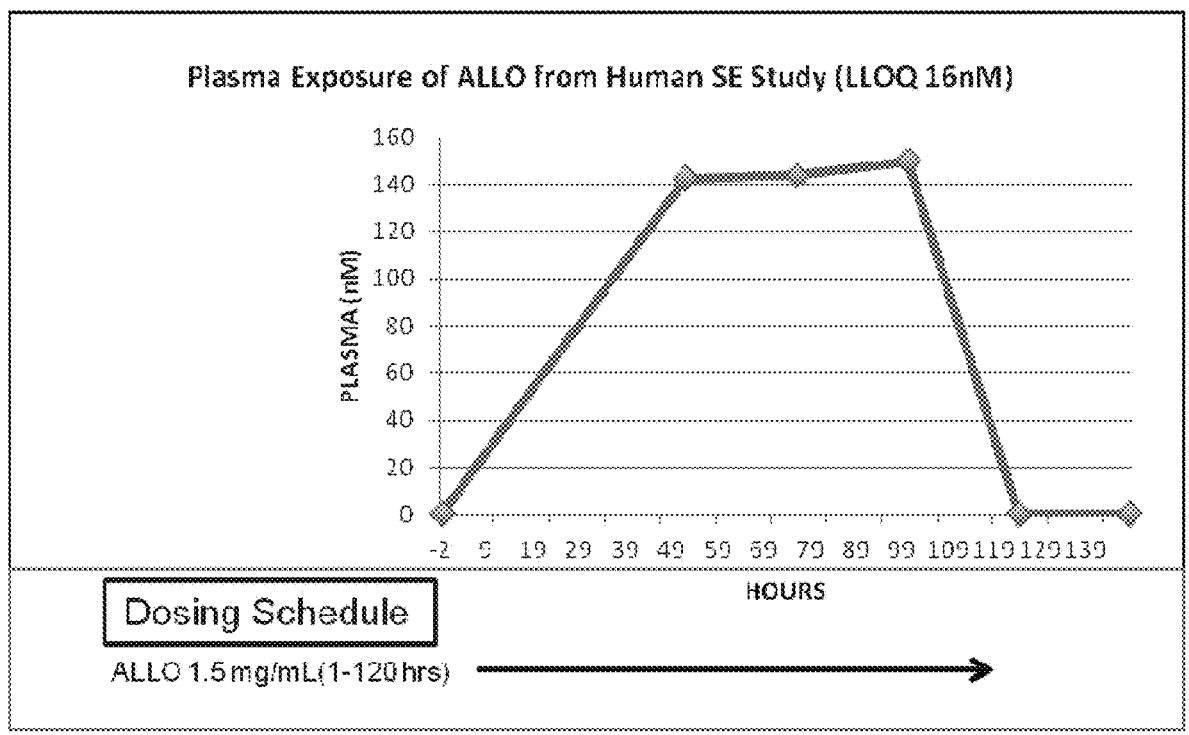
FIG. 3 is a graph depicting the plasma concentration profile of a patient intravenously administered 1.5 mg/ml allopregnanolone in 6% hydroxypropyl-3-cyclodextrin in 0.9% sodium chloride for 5 days.

Example 4. Plasma Concentration of Allopregnanolone in Refractory Status Epilepticus The plasma concentration profile over time of allopregnanolone in male patient diagnosed with refractory status epilepticus was evaluated as shown in FIG. 3. The patient was dosed Allopregnanolone 1.5 mg/ml in 6% hydroxypropyl-β-cyclodextrin in 0.9% sodium chloride intravenously for 5 days. Infusion rate 86 µg/kg/h. Dosing schedule included 5.6 mg/h of Allopregnanolone at 3.8 mL/h. Plasma concentrations was analyzed 2 hours prior to start of infusion then 52, 76, 100, 124, and 148 hours.

Figure 4A:
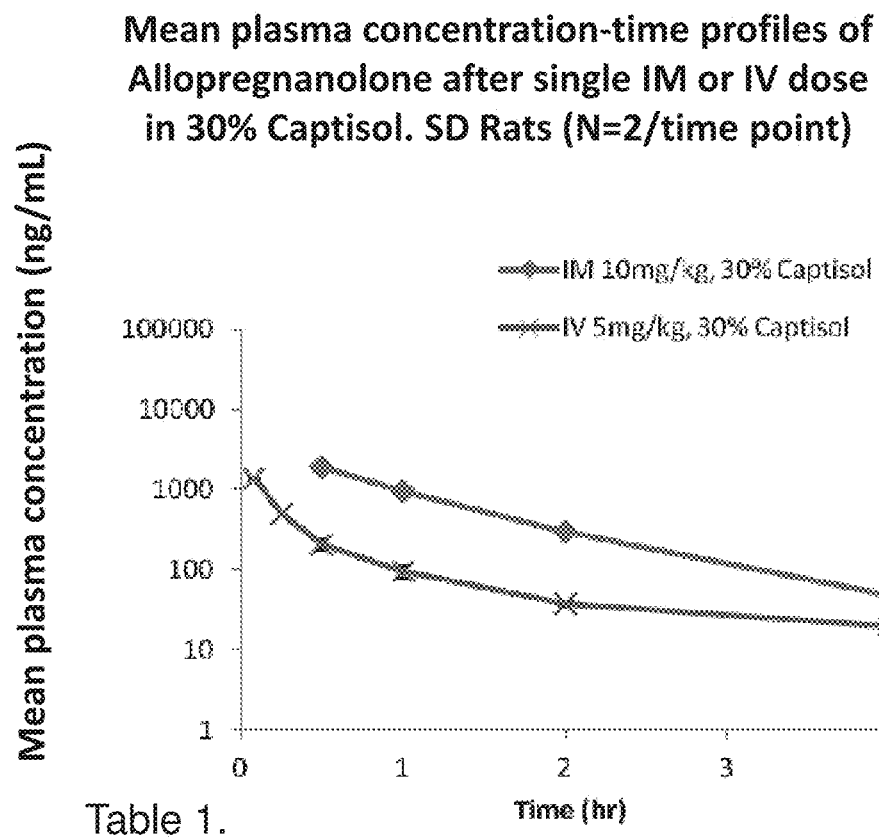
FIG. 4A depicts the plasma exposure profiles of allopregnanolone measured by LC/MS-MS after single intramuscular (10 mg/kg) or intravenous (5 mg/kg) allopregnanolone dose in 30% CAPTISOL® in SD rats.
Figure 4B:
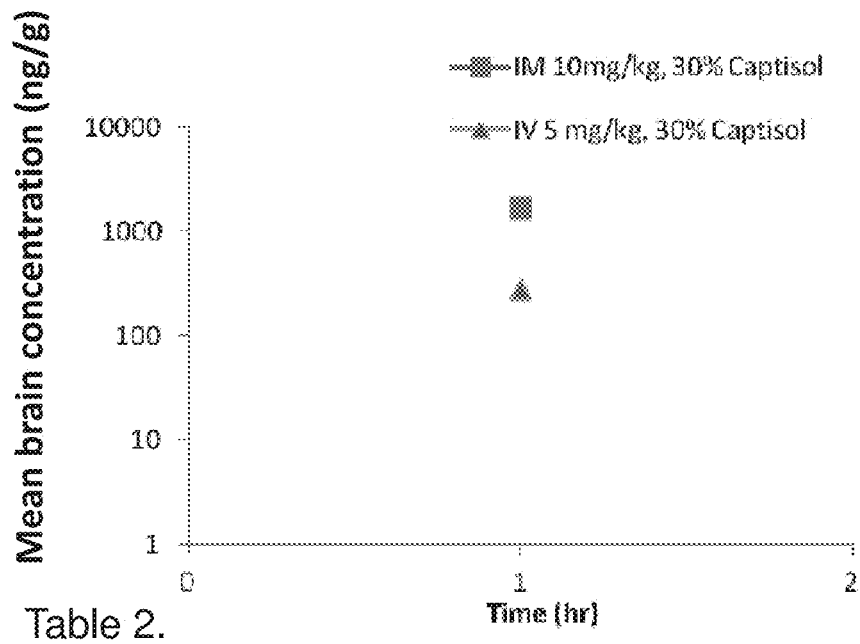
FIG. 4B depicts the brain exposure profiles of allopregnanolone measured by LC/MS-MS after single intramuscular (10 mg/kg) or intravenous (5 mg/kg) allopregnanolone dose in 30% CAPTISOL® in SD rats.

Example 5. Allopregnanolone In Vivo Plasma Concentration Post Intramuscular and Intravenous Administration The plasma and brain exposure profiles of Allopregnanolone were measured by LC/MS-MS after single intramuscular (IM) (10 mg/kg) or intravenous (IV) (5 mg/kg) dose in 30% CAPTISOL® in SD rats. Analysis shows that Allopregnanolone dosed IM (10 mg/kg) has an unexpectedly substantially greater exposure in plasma (671-916%, 0.5-2 hr) and brain (506%, 1 hr) relative to IV (5 mg/kg) dose as indicated in Table 1 and 2. N=2/time point. Error bars, SEM (FIGS. 4A and 4B).

Example 6. Progesterone in 6% CAPTISOL® Rescue of Injury in TBI Rodent Model

Figure 5A:
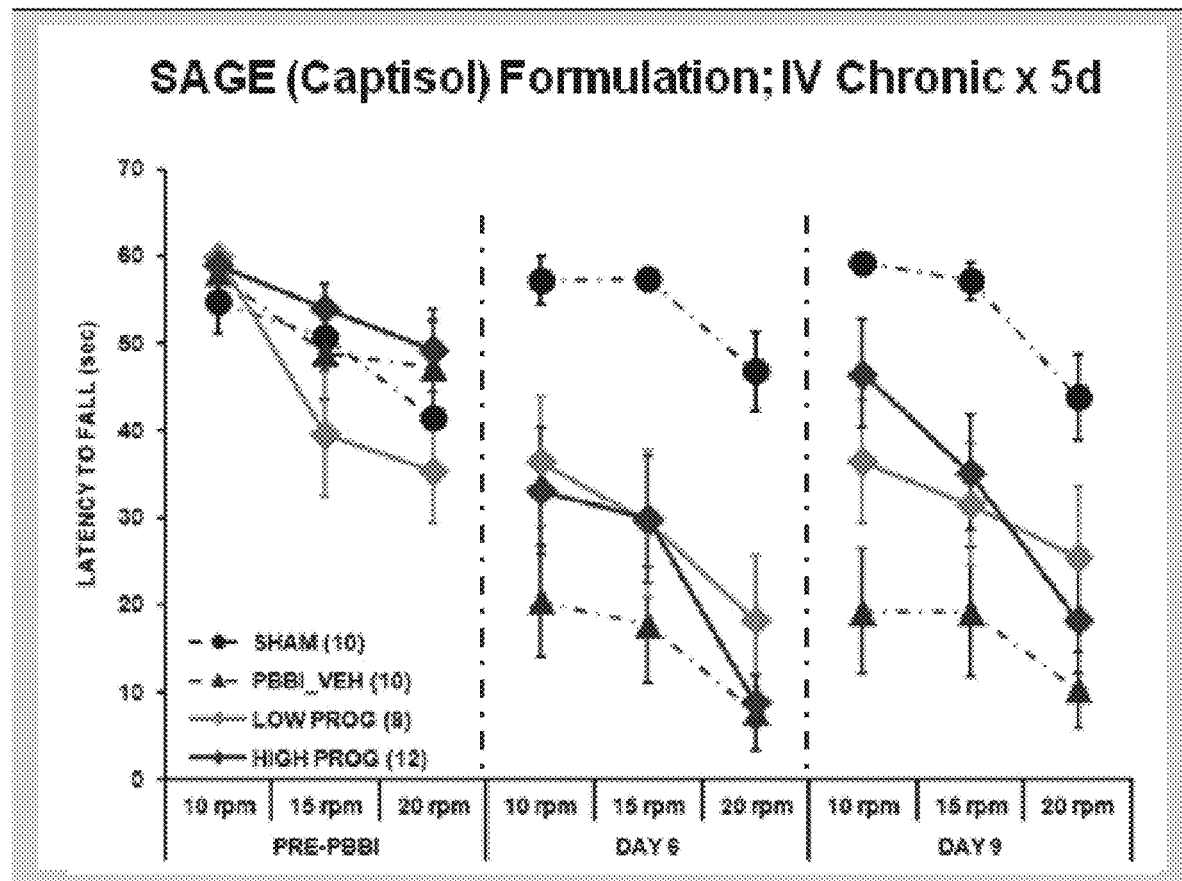
FIG. 5A depicts the latency to fall period (seconds) in a penetrating ballistic brain injury rodent model of traumatic brain injury in both the low and high dose groups progesterone in 6% CAPTISOL®.
Figure 5B:
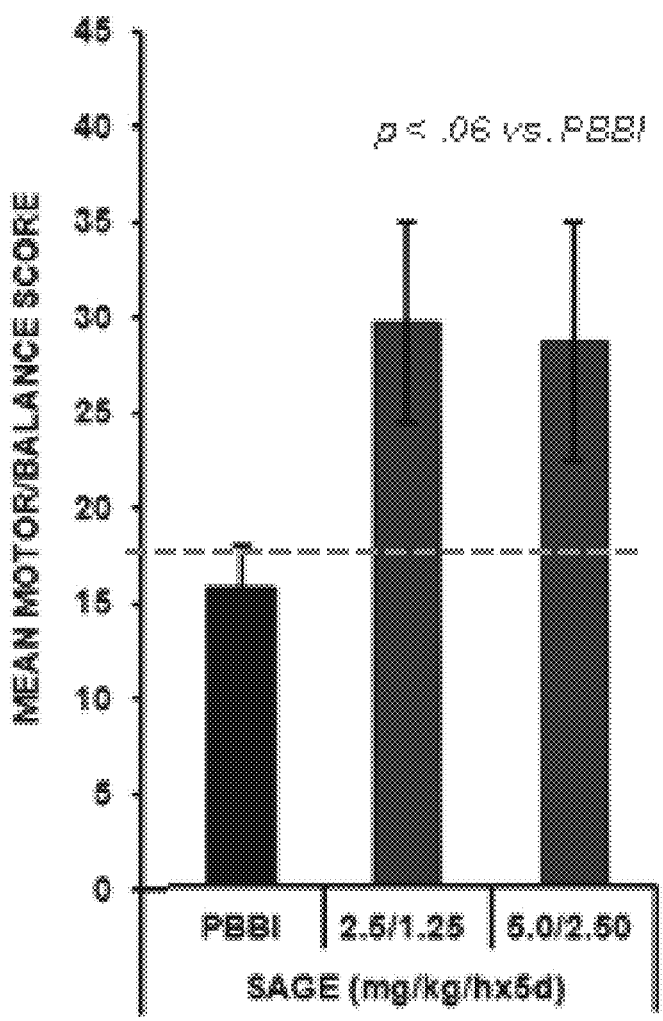
FIG. 5B depicts the mean motor score in a penetrating ballistic brain injury rodent model of traumatic brain injury in both the low and high dose groups progesterone in 6% CAPTISOL®.

Progesterone in 6% CAPTISOL® rescued motor impairment in a penetrating ballistic brain injury rodent model of traumatic brain injury in both the low and high dose groups (FIG. 5A and FIG. 5B). Progesterone was administered via a bolus loading dose followed by a 5 day continuous infusion where progesterone was tapered over the last 24 hours every 8 hrs by 25%. The low dose group received 2.5 mg/kg/hr for a 1 hr bolus infusion followed by a maintenance dose of 1.25 mg/kg/hr over 5 days with the last 24 hours being a taper. The high dose group received 5.0 mg/kg/hr for a 1 hr bolus infusion followed by a maintenance dose of 2.50 mg/kg/hr over 5 days with the last 24 hours being a taper.

It is understood that the disclosed invention is not limited to the particular methodology, protocols, and reagents described as these may vary. It is also to be understood that the terminology used herein is for the purpose of describing particular embodiments only, and is not intended to limit the scope which will be limited only by the appended claims.

Although any methods and materials similar or equivalent to those described herein can be used in the practice or testing, the preferred methods, devices, and materials are as described. Publications cited herein and the materials for which they are cited are specifically incorporated by reference

I claim:

1. A method of treating a traumatic brain injury in a subject in need thereof, comprising administering to the subject an effective amount of an aqueous pharmaceutical composition formulated for parenteral administration comprising allopregnanolone at a concentration of 5 mg/mL, sulfo butyl ether β-cyclodextrin at a concentration of about 250 mg/mL, and a citrate buffer, wherein the pH of the composition is from 5 to 9.

2. The method of claim 1, wherein the composition is formulated for intravenous administration.

3. The method of claim 1, wherein the composition further comprises an antioxidant.

4. The method of claim 1, wherein the composition has a pH of about 6.

5. The method of claim 1, wherein the composition is formulated for subcutaneous administration.

6. The method of claim 1, wherein the composition is contained within a glass vial.

* * * * *